US012171941B2

(12) United States Patent
Kiljanek

(10) Patent No.: US 12,171,941 B2
(45) Date of Patent: *Dec. 24, 2024

(54) VENTILATOR SYSTEM WITH GAS FLOW CONTROL

(71) Applicant: Lukasz R. Kiljanek, Chesapeake Beach, MD (US)

(72) Inventor: Lukasz R. Kiljanek, Chesapeake Beach, MD (US)

(*) Notice: Subject to any disclaimer, the term of this patent is extended or adjusted under 35 U.S.C. 154(b) by 116 days.

This patent is subject to a terminal disclaimer.

(21) Appl. No.: 17/705,539

(22) Filed: Mar. 28, 2022

(65) Prior Publication Data

US 2023/0011630 A1    Jan. 12, 2023

Related U.S. Application Data

(63) Continuation of application No. 17/345,994, filed on Jun. 11, 2021, now Pat. No. 11,285,286.
(Continued)

(51) Int. Cl.
*A61M 16/04* (2006.01)
*A61M 16/00* (2006.01)
(Continued)

(52) U.S. Cl.
CPC ........ *A61M 16/042* (2014.02); *A61M 16/024* (2017.08); *A61M 16/0404* (2014.02);
(Continued)

(58) Field of Classification Search
CPC ............ A61M 16/0057; A61M 16/024; A61M 16/04; A61M 16/0402; A61M 16/0404;
(Continued)

(56) References Cited

U.S. PATENT DOCUMENTS 4,265,237 A * 5/1981 Schwanbom ......... A61M 16/00
128/205.24
4,819,664 A    4/1989 Nazari
(Continued)

FOREIGN PATENT DOCUMENTS

DE    102013100991    8/2014
DE    102018113154    12/2019
(Continued)

OTHER PUBLICATIONS

Anantham et al., Devanand "Clinical review: Independent lung ventilation in critical care", Critical Care, Dec. 2005, vol. 9, No. 6. (Published online: Oct. 10, 2005) 7 pages.
(Continued)

*Primary Examiner* — Joseph D. Boecker
(74) *Attorney, Agent, or Firm* — Polsinelli LLP

(57) ABSTRACT

Ventilator system with multiple inspiratory lumens is provided. The inspiratory lumens are configured so that separate inspiratory lumens provide inspiratory gas mixtures to separate portions of a patient's airways, for instance to separate lungs and/or bronchi. The ventilator system can include one or more expiratory lumens to evacuate expiratory gases from airways. The use of separate inspiratory lumen(s), with expiratory lumen(s), allows for functional separation of structural portions of the lungs, and maintenance of continuous or almost continuous flow through at least part of respiratory cycle via inspiratory and expiratory lumens. This can further reduce dead space and clear suspended therein diseases causative agents with improvement in outcomes, reduce risk of cross-contamination or cross-infection between different parts of airways, for example such as cross-infection from one lung lobe to another lobe or. The ventilator system allows for independent titration of PEEP, $pCO_2$ and $pO_2$ with no need for permissive hypercapnia.

110 Claims, 24 Drawing Sheets

Related U.S. Application Data

(60) Provisional application No. 63/077,037, filed on Sep. 11, 2020, provisional application No. 63/075,327, filed on Sep. 8, 2020, provisional application No. 63/075,555, filed on Sep. 8, 2020.

(51) Int. Cl.
    *A61M 16/08*     (2006.01)
    *A61M 16/10*     (2006.01)
    *A61M 16/12*     (2006.01)
    *A61M 16/20*     (2006.01)

(52) U.S. Cl.
    CPC .... *A61M 16/0463* (2013.01); *A61M 16/0486* (2014.02); *A61M 16/0883* (2014.02); *A61M 16/106* (2014.02); *A61M 16/107* (2014.02); *A61M 16/12* (2013.01); *A61M 16/208* (2013.01); *A61M 16/0009* (2014.02); *A61M 2016/0027* (2013.01); *A61M 2016/0039* (2013.01); *A61M 16/0057* (2013.01); *A61M 2016/103* (2013.01); *A61M 16/1065* (2014.02); *A61M 2202/0225* (2013.01); *A61M 2205/3344* (2013.01)

(58) Field of Classification Search
    CPC ............ A61M 16/042; A61M 16/0427; A61M 16/0434; A61M 16/0463; A61M 16/0486; A61M 16/0883; A61M 16/106; A61M 16/1065; A61M 16/107; A61M 16/12; A61M 2210/1035; A61M 2210/1039; A61M 2016/0027; A61M 2016/0039; A61M 2016/103; A61M 2205/3344
    See application file for complete search history.

(56) References Cited

U.S. PATENT DOCUMENTS

| | | | | |
|---|---|---|---|---|
| 5,309,906 | A * | 5/1994 | LaBombard | A61M 16/0495 128/207.14 |
| 5,359,999 | A * | 11/1994 | Kinsman | A61M 16/0486 128/204.23 |
| 5,706,830 | A | 1/1998 | Parker | |
| 6,254,591 | B1 | 7/2001 | Roberson | |
| 6,390,988 | B1 | 5/2002 | Robinson | |
| 7,121,280 | B2 | 10/2006 | Kyle | |
| 7,481,222 | B2 | 1/2009 | Reissmann | |
| 7,588,033 | B2 | 9/2009 | Wondka | |
| D654,586 | S | 2/2012 | Hogerwerf et al. | |
| 8,950,400 | B2 | 2/2015 | Enk | |
| 8,978,657 | B2 | 3/2015 | Sandmore et al. | |
| 10,118,007 | B2 | 11/2018 | Enk | |
| 10,293,130 | B2 | 5/2019 | van Asseldonk et al. | |
| 10,406,308 | B2 | 9/2019 | Enk | |
| 10,543,335 | B2 | 1/2020 | Enk | |
| 10,857,318 | B2 | 12/2020 | Enk et al. | |
| 10,960,166 | B2 | 3/2021 | Enk | |
| 10,980,954 | B1 * | 4/2021 | Bell | A61M 16/0402 |
| 11,285,286 | B1 * | 3/2022 | Kiljanek | A61M 16/0486 |
| 2004/0000314 | A1 | 1/2004 | Angel | |
| 2004/0231673 | A1 * | 11/2004 | Reissmann | A61M 16/042 128/207.14 |
| 2007/0017519 | A1 | 1/2007 | Kuo | |
| 2009/0038621 | A1 | 2/2009 | Miller et al. | |
| 2009/0156953 | A1 | 6/2009 | Wondka et al. | |
| 2011/0265799 | A1 * | 11/2011 | Lisogurski | A61M 16/042 128/207.15 |
| 2013/0014754 | A1 | 1/2013 | Guerra et al. | |
| 2014/0276178 | A1 | 9/2014 | Simon | |
| 2014/0305434 | A1 * | 10/2014 | Beck | A61M 16/042 128/203.14 |
| 2016/0303340 | A1 * | 10/2016 | Sinderby | A61M 16/16 |
| 2018/0272089 | A1 | 9/2018 | Maracaja | |
| 2019/0022342 | A1 | 1/2019 | Enk | |
| 2019/0388634 | A1 | 12/2019 | Enk et al. | |
| 2020/0282164 | A1 | 9/2020 | Thomas | |
| 2021/0069435 | A1 | 3/2021 | Enk et al. | |
| 2021/0299390 | A1 * | 9/2021 | Kremeier | A61M 16/0875 |
| 2024/0050678 | A1 * | 2/2024 | Kiljanek | A61M 16/024 |

FOREIGN PATENT DOCUMENTS

| | | |
|---|---|---|
| GB | 2515478 | 12/2014 |
| WO | WO 2001/024861 | 4/2001 |
| WO | WO 2002/047748 | 6/2002 |
| WO | WO 2022/055749 | 3/2022 |

OTHER PUBLICATIONS

Bora et al., Vaibhav; "Double Lumen Endobronchial Tubes", NCBI Bookshelf. A service of National Library of Medicine, National Institutes of Health. StatPearls Publishing: Jan. 2021. Last updated: May 4, 2021. 8 pages.

G.L. Zeitlin, D.H. Short, G.H. Ryder "An Assessment of The Robertshaw Double-Lumen Tube", by The London Chest Hospital and the Middlesex Hospital, London. British Journal of Anesthesia, (1965), 37, 858-860, 3 pages.

Hess et al., Dean R.; "Tracheal Gas Insufflation and Related Techniques to Introduce Gas Flow into the Trachea", Respiratory Care, Feb. 2001, vol. 46, No. 2. 12 pages.

PCT Application No. PCT/US2021/048373 International Search Report and Written Opinion dated Oct. 12, 2021.

U.S. Appl. No. 17/345,994 Office Action mailed Oct. 1, 2021.

Https://www.ventinovamedical.com/tritube/: [Downloaded from the internet: Jan. 25, 2023].

Tribute The Ultrathin Ventilation Tube, Ventinova Medical [Downloaded on Jan. 18, 2023].

\* cited by examiner

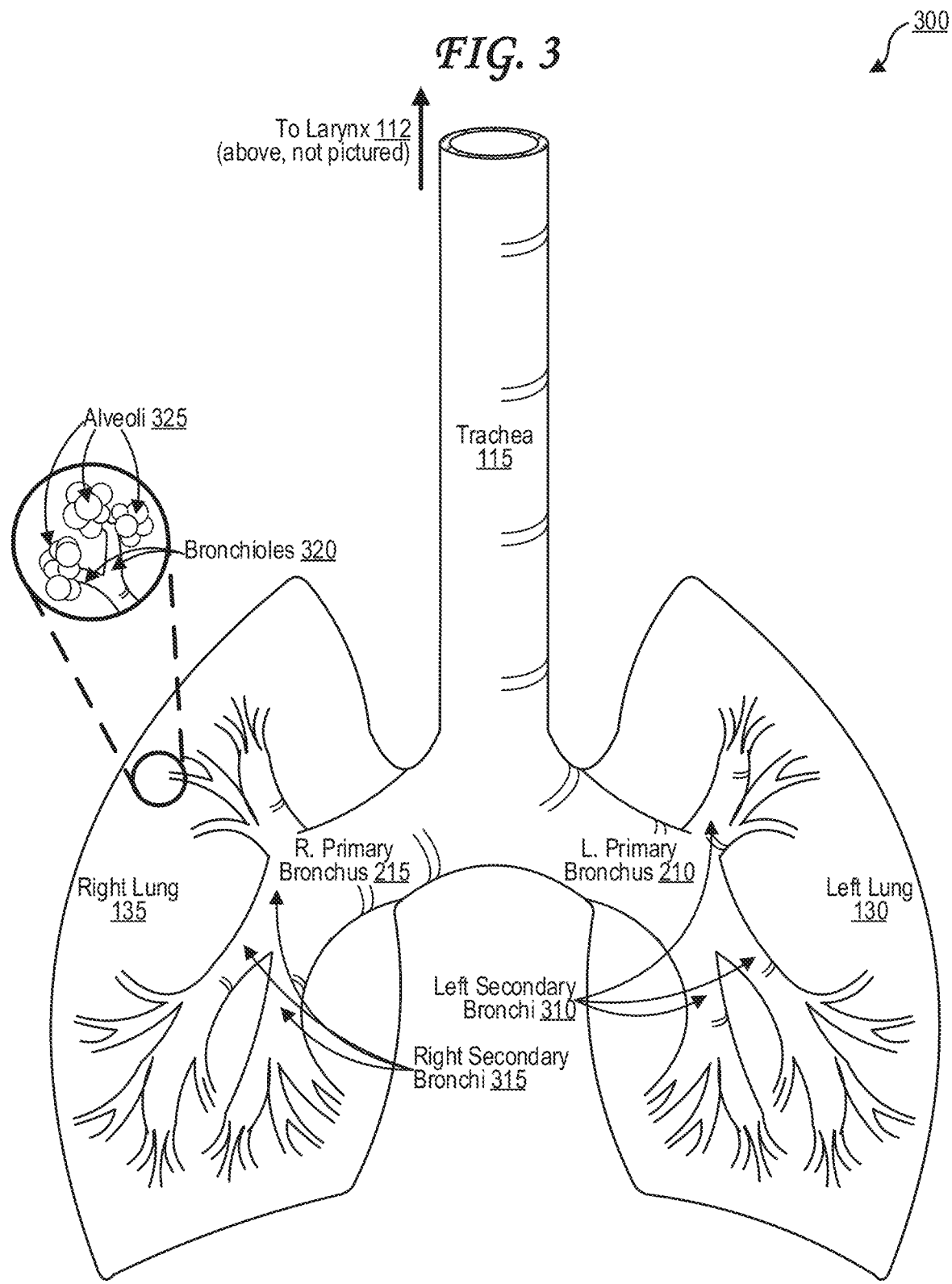

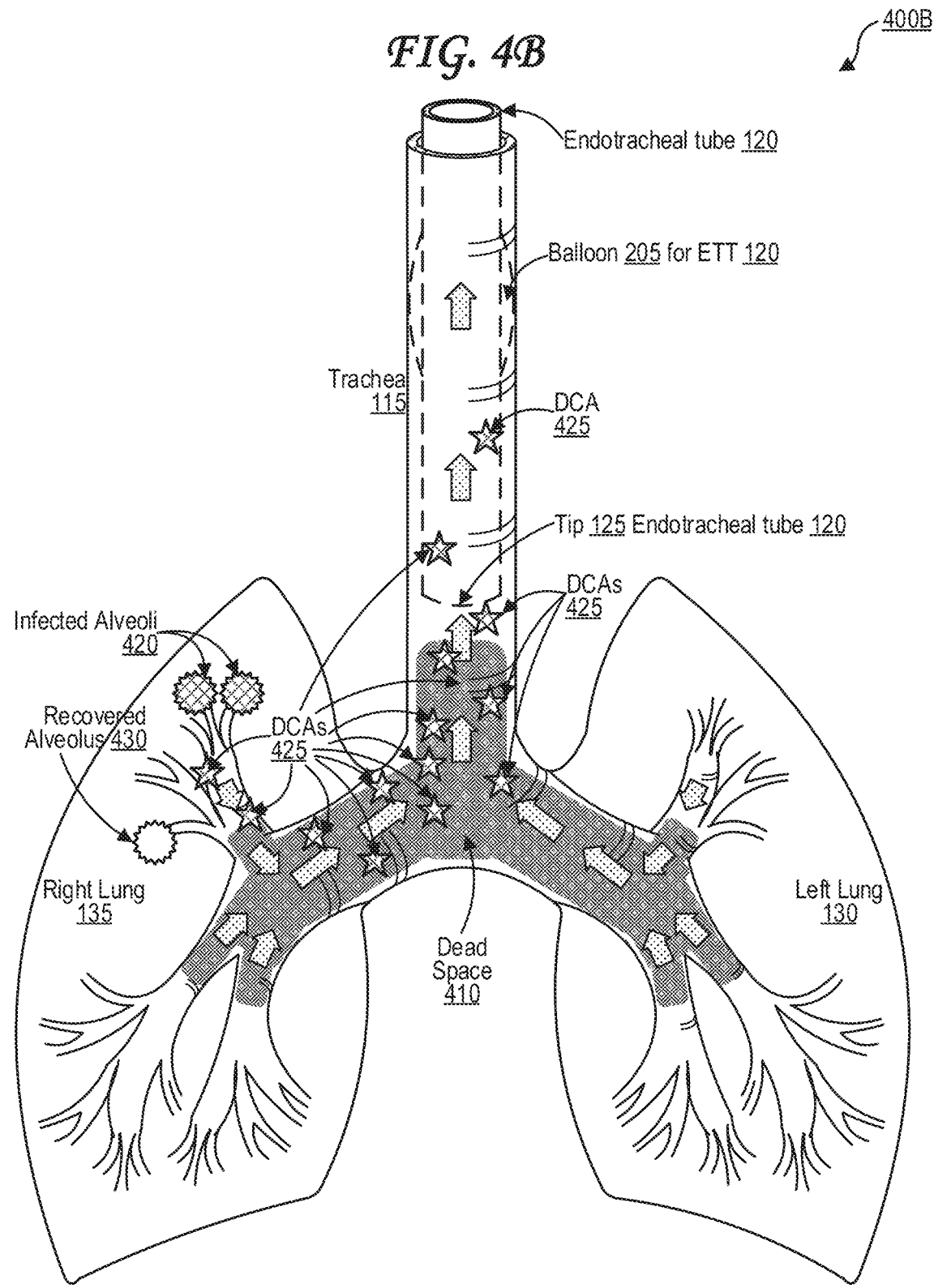

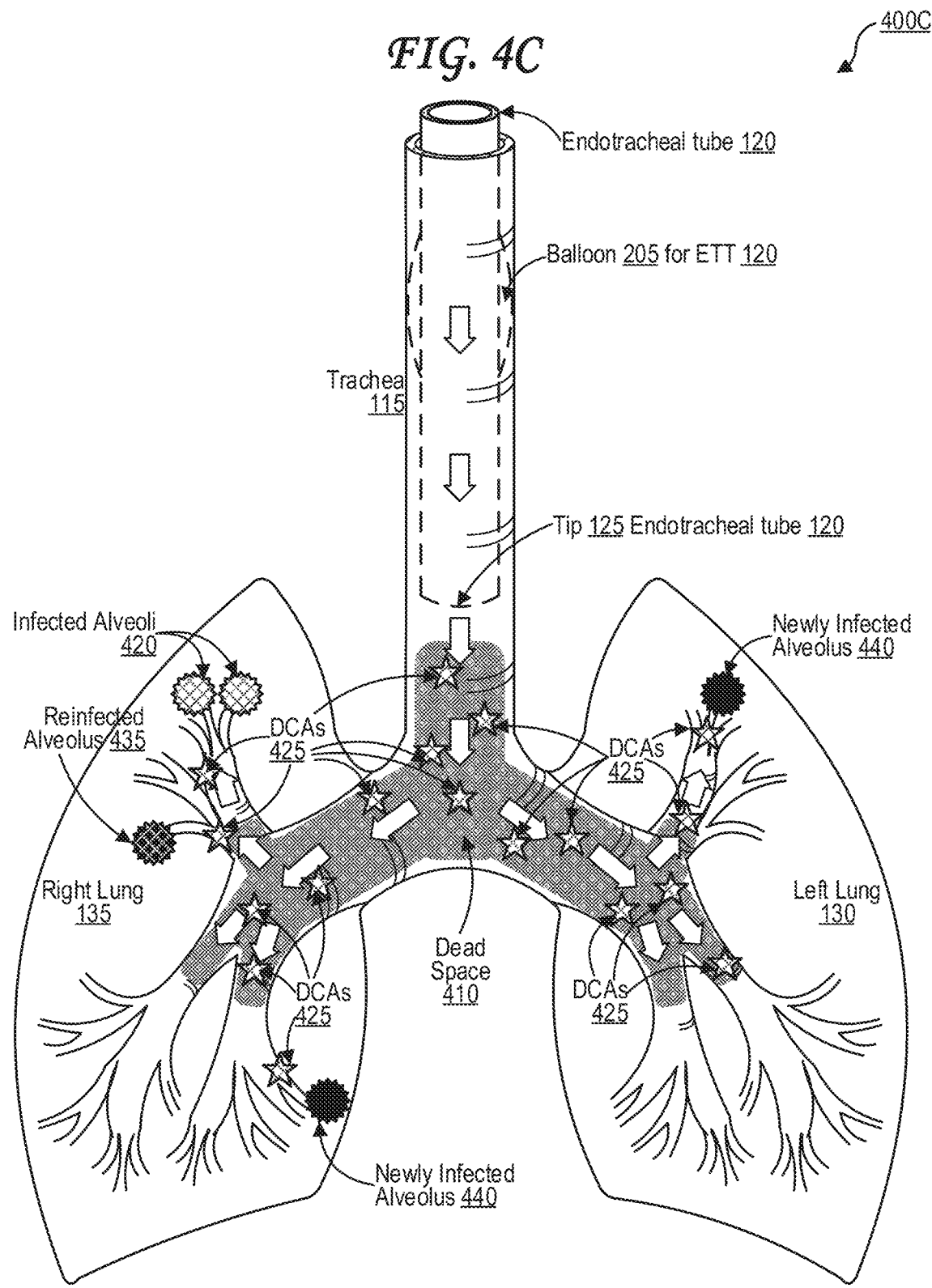

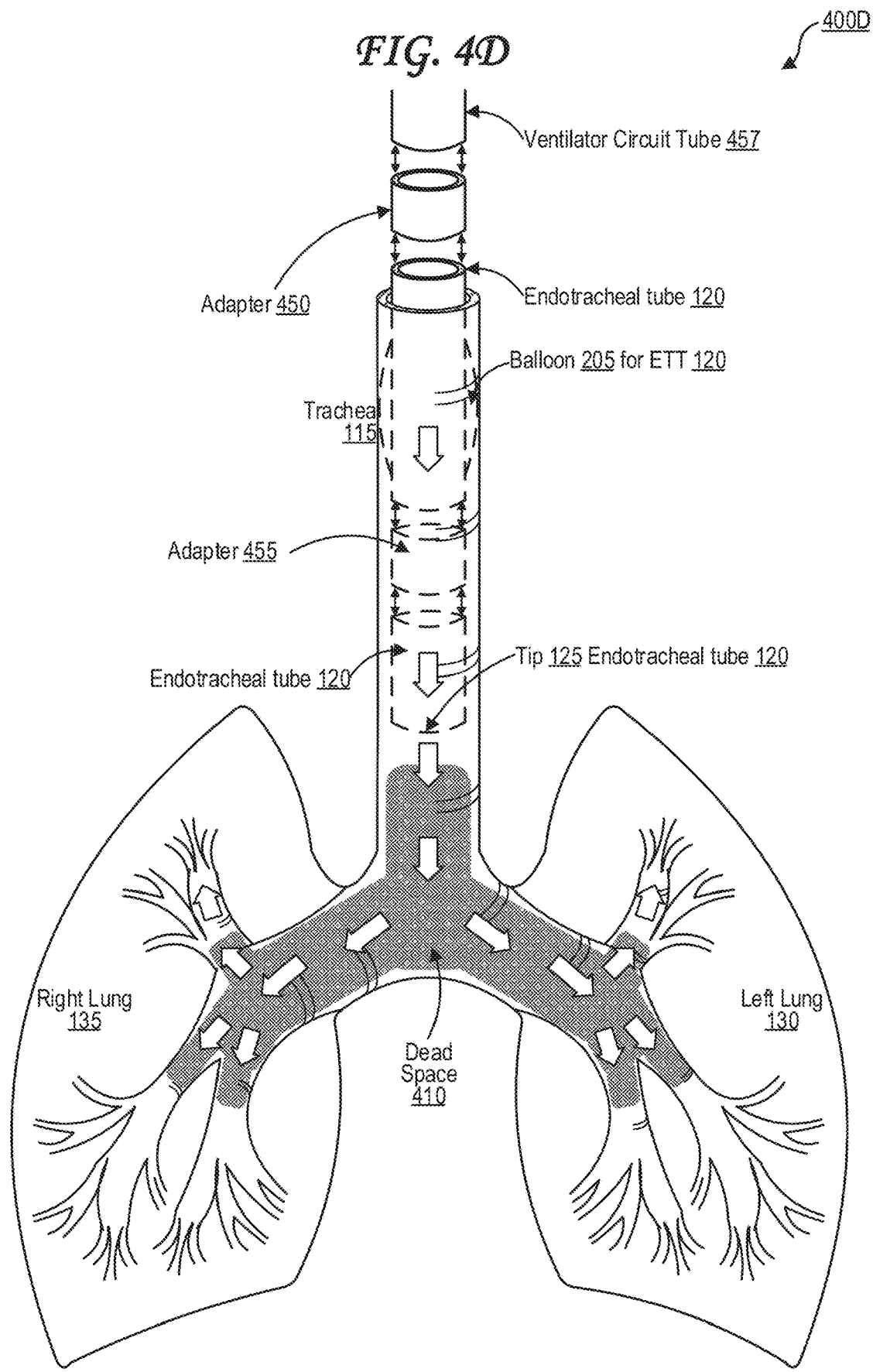

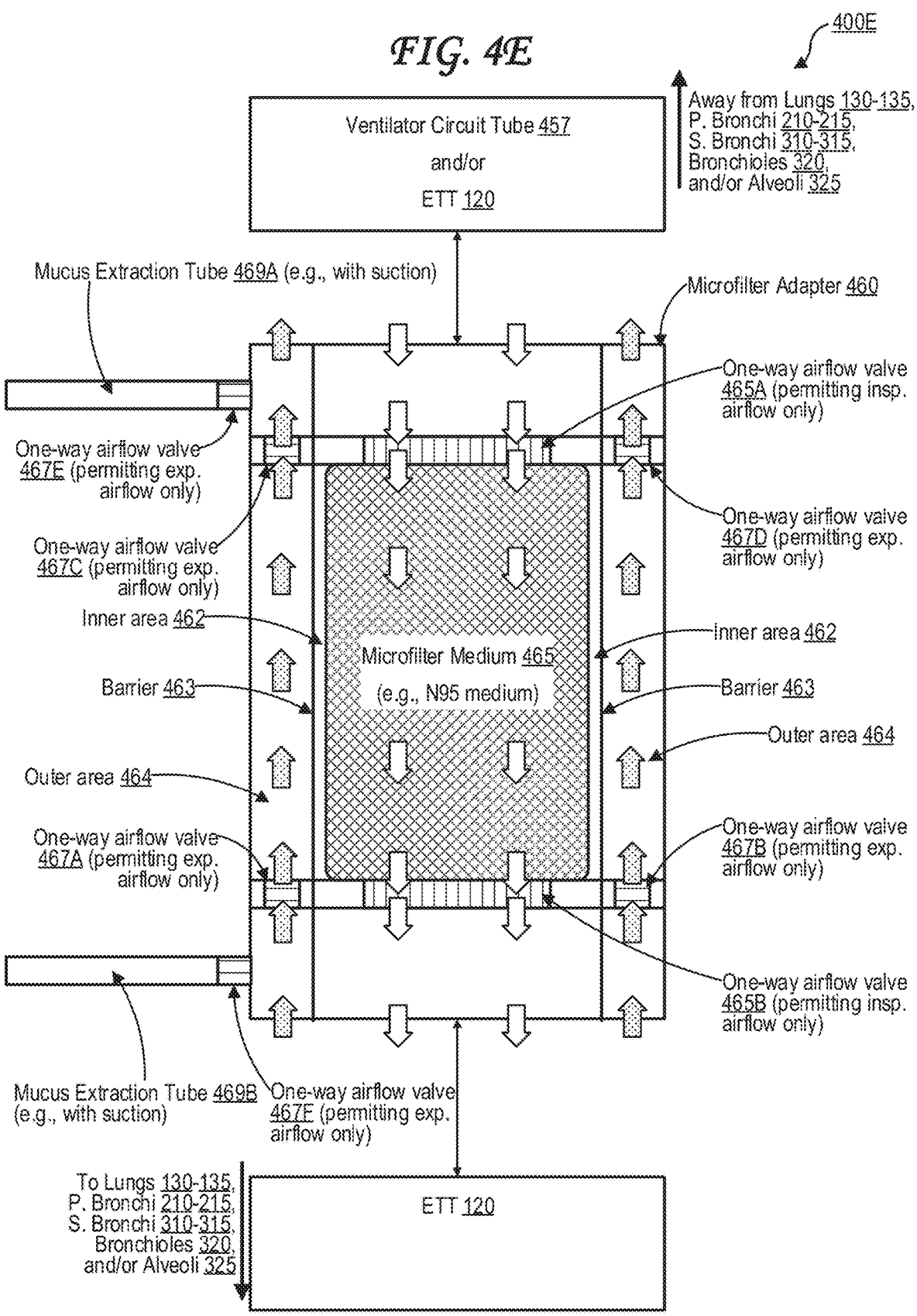

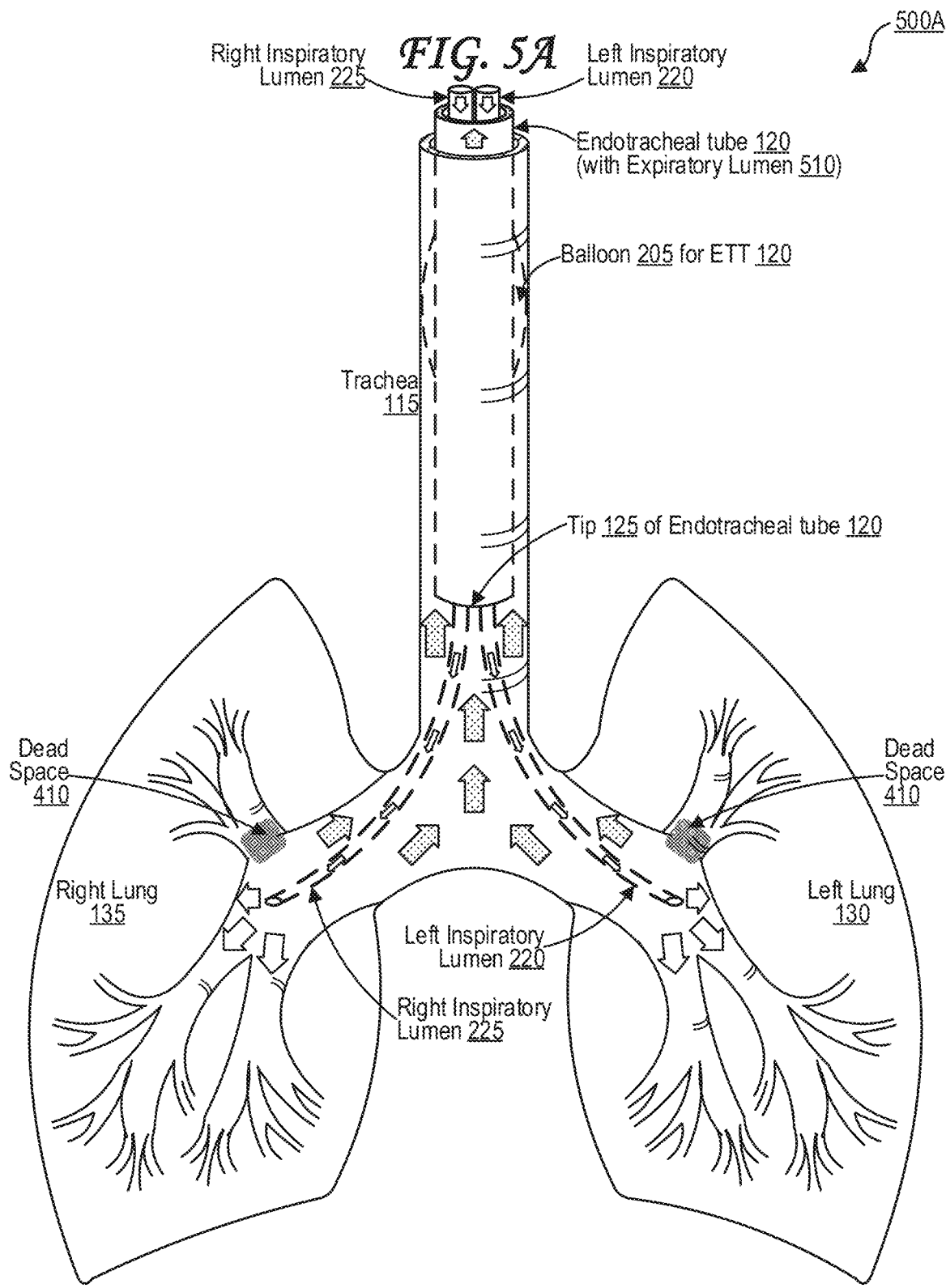

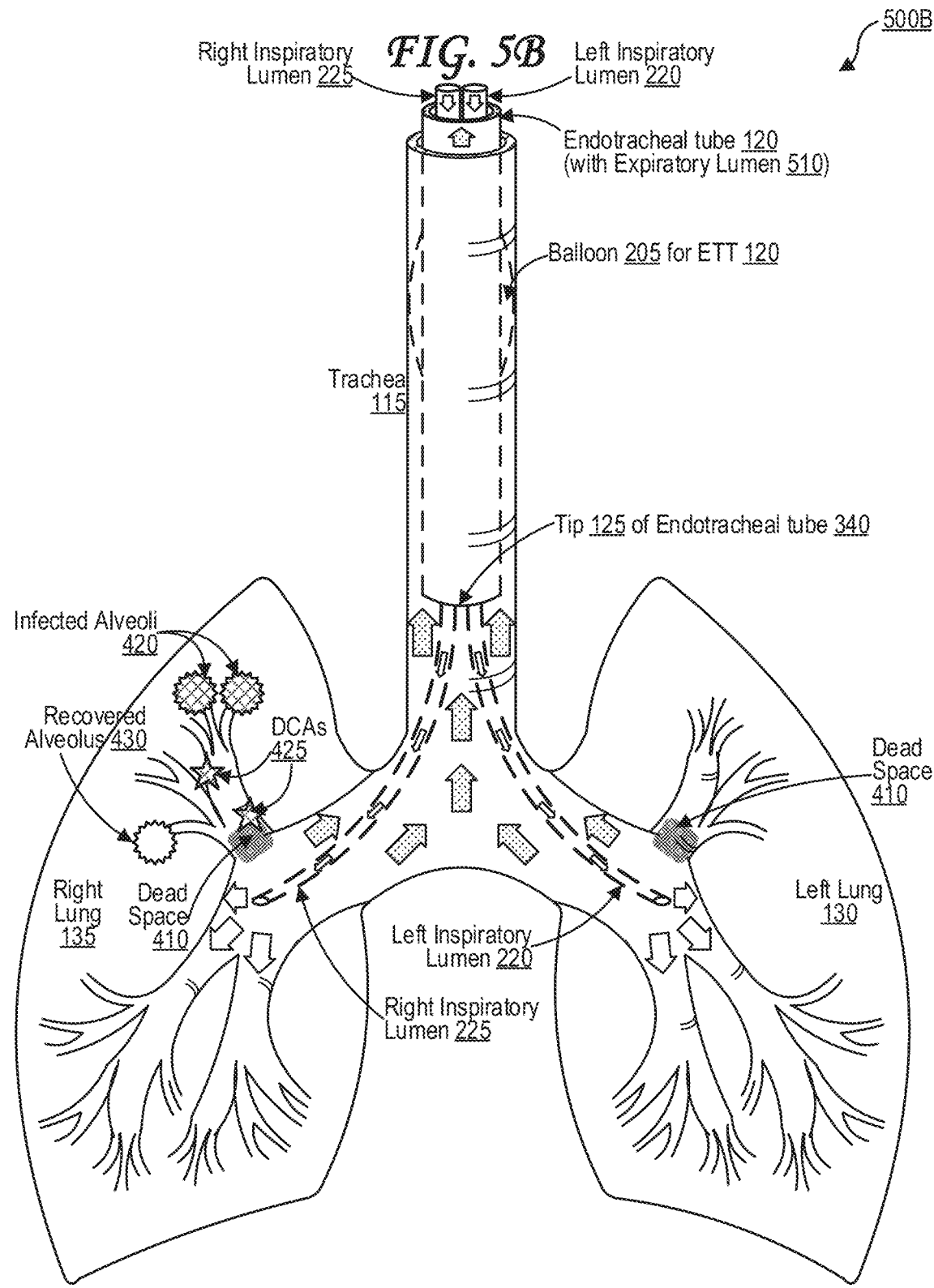

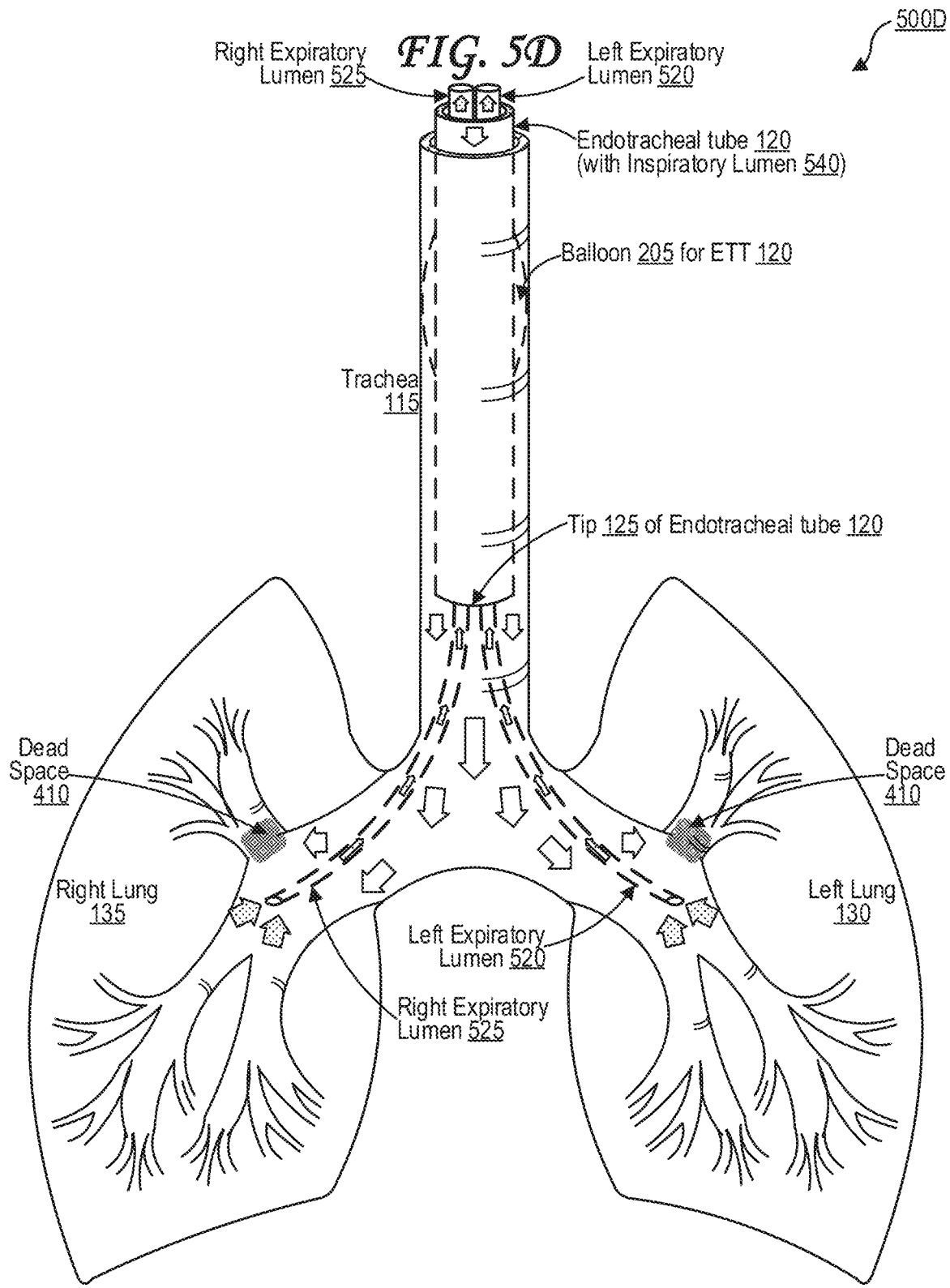

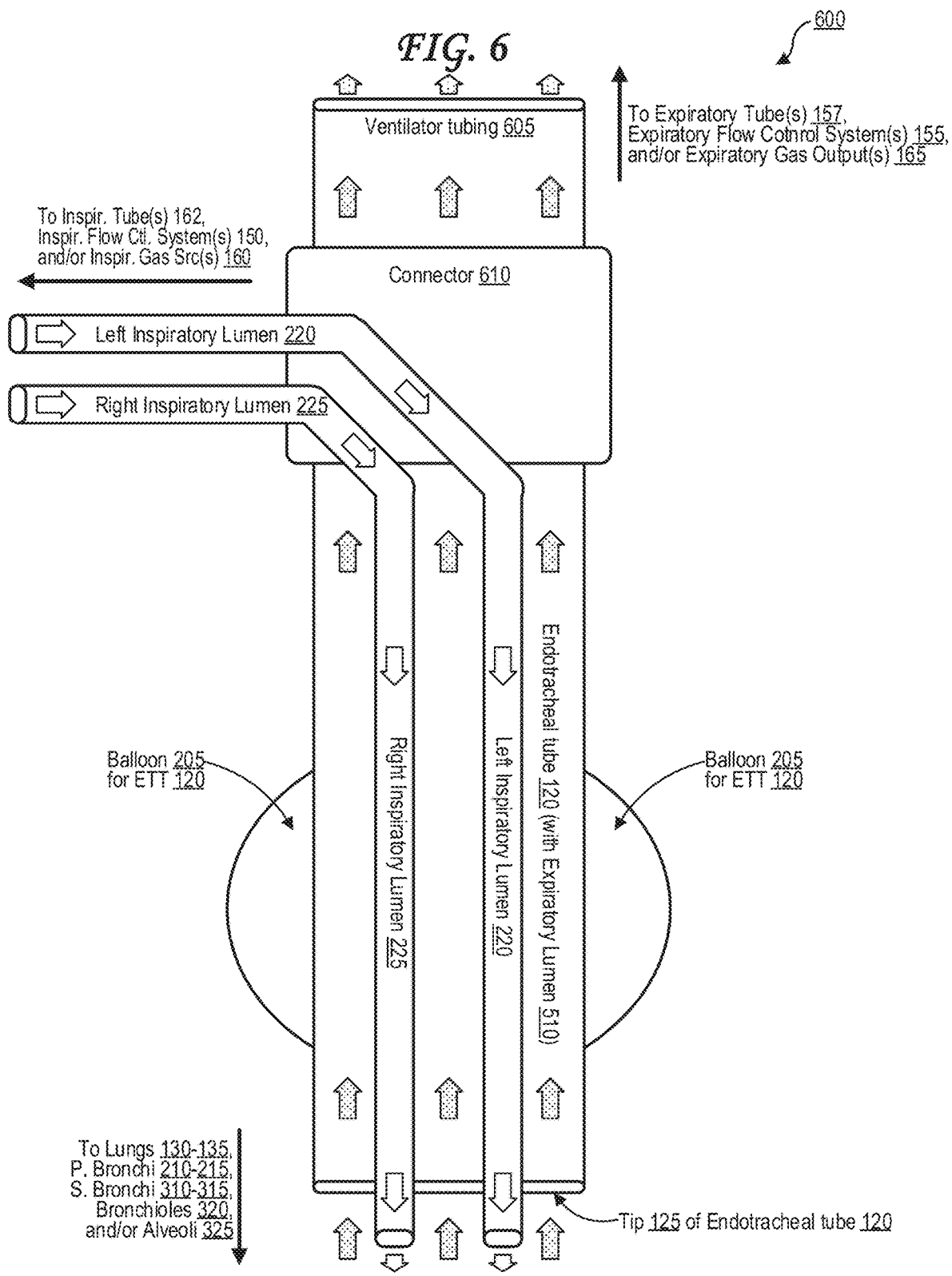

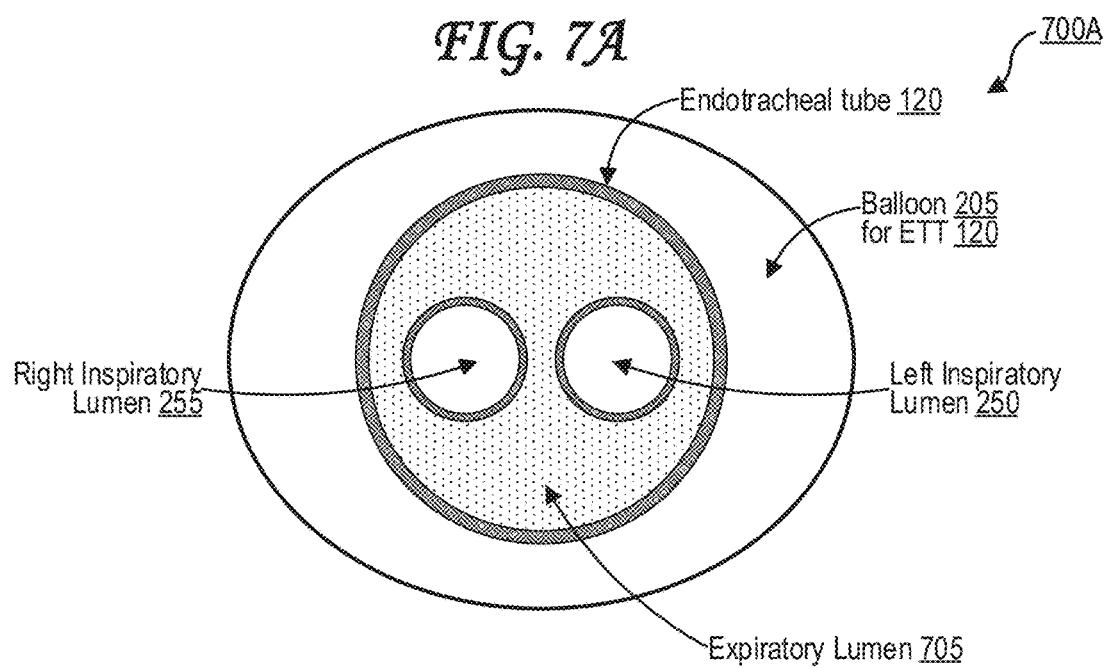
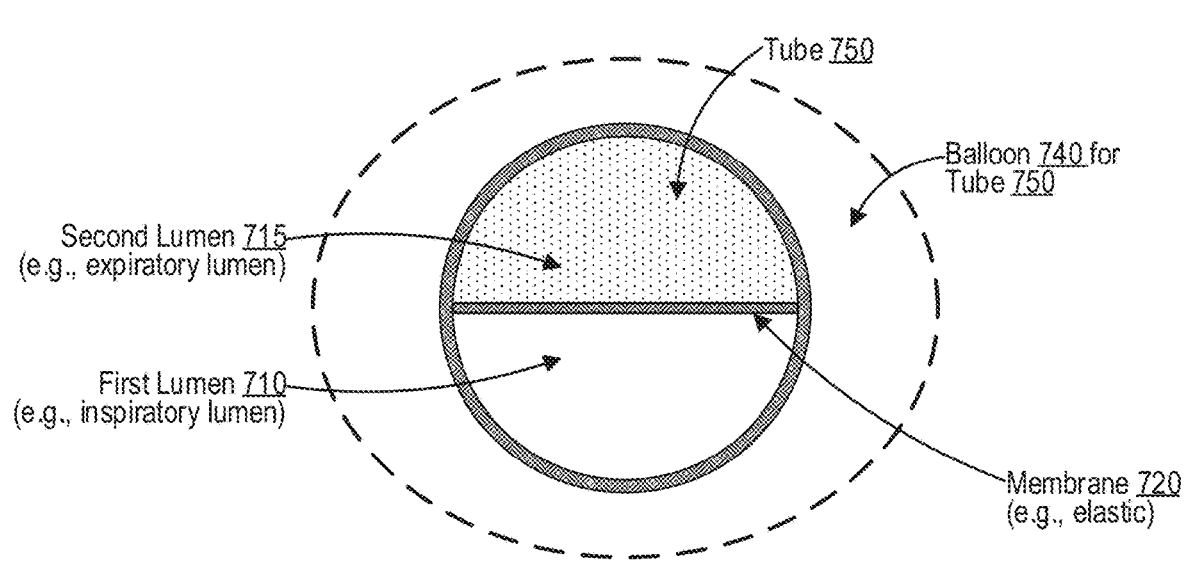

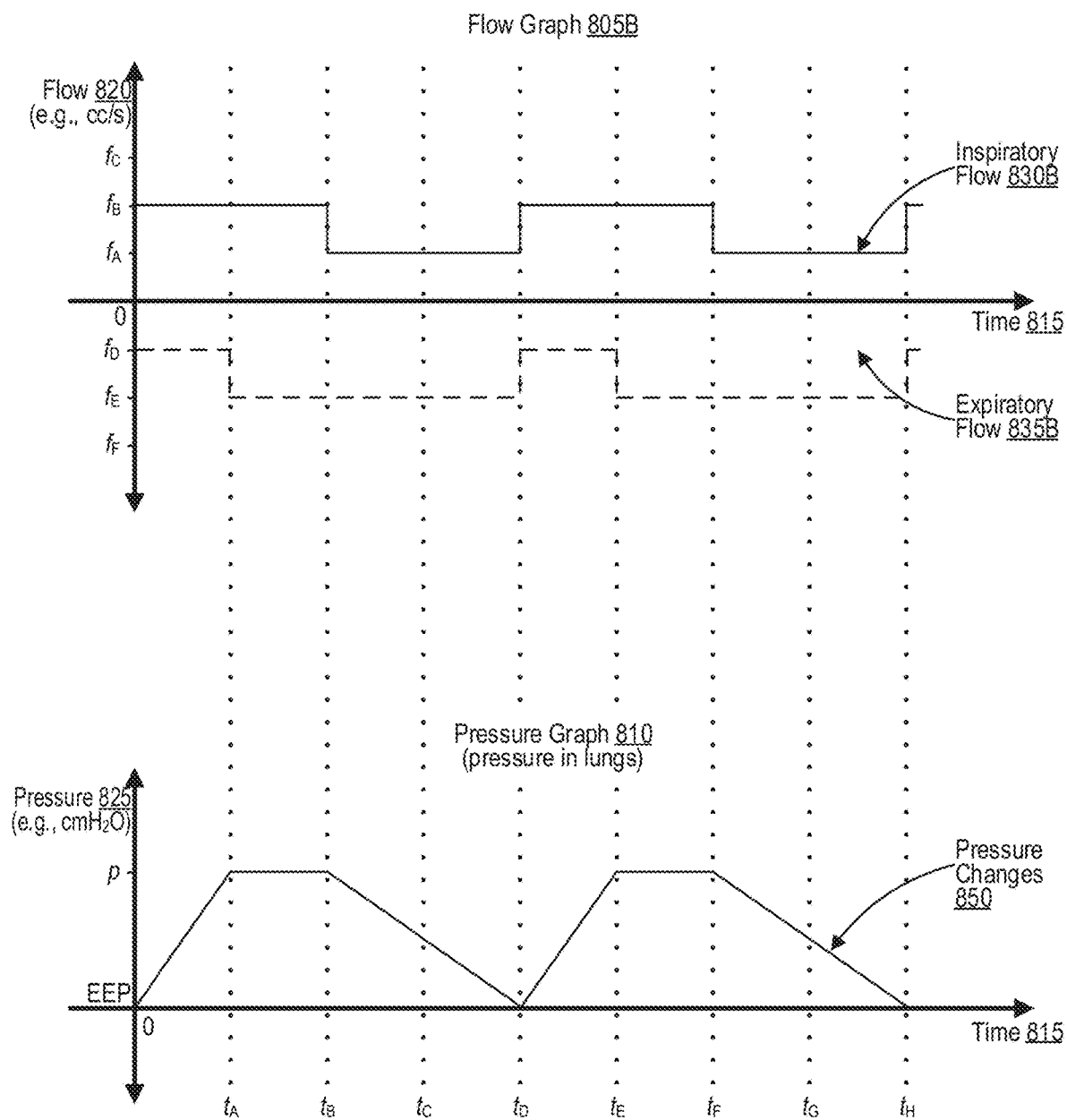

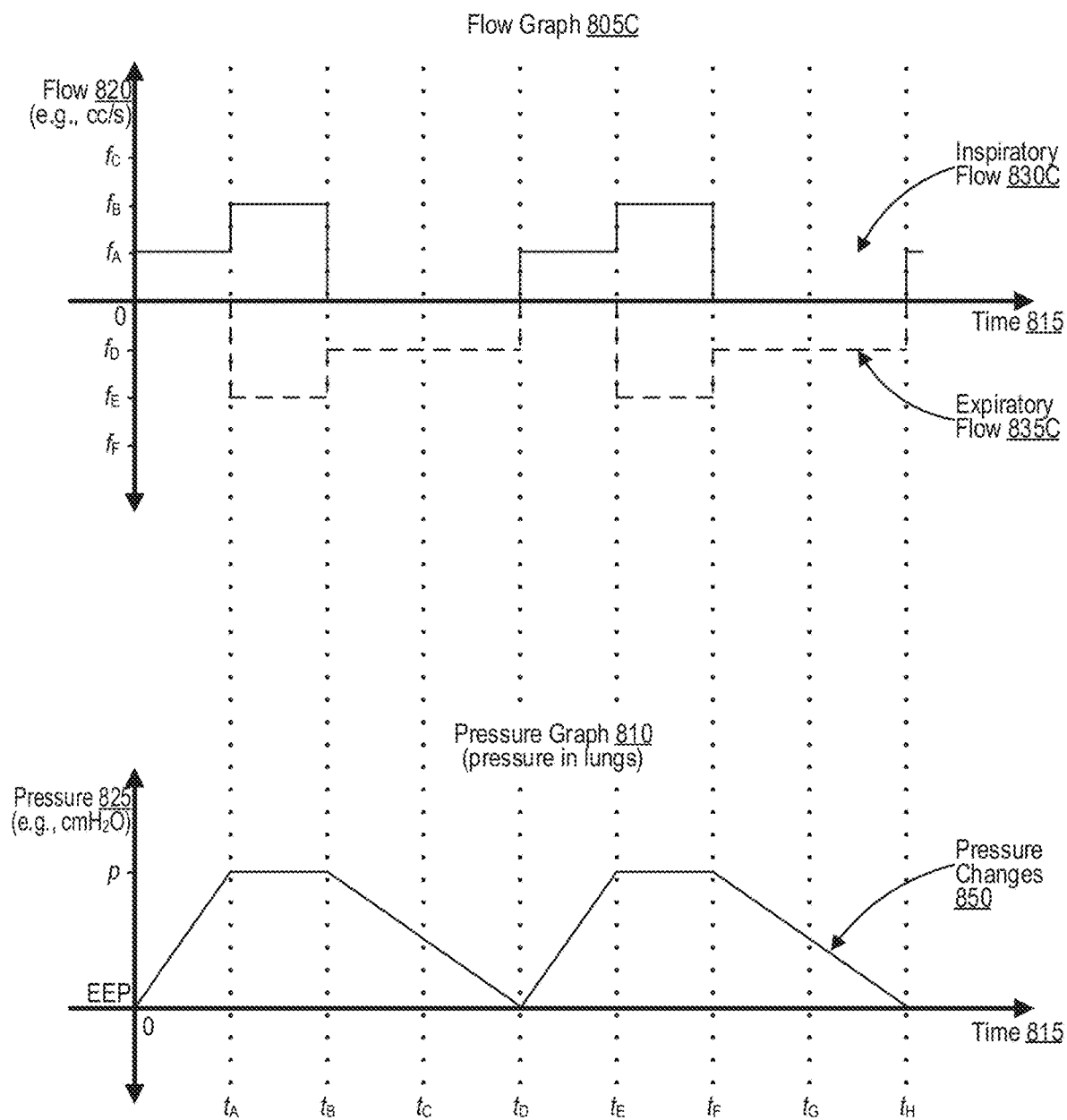

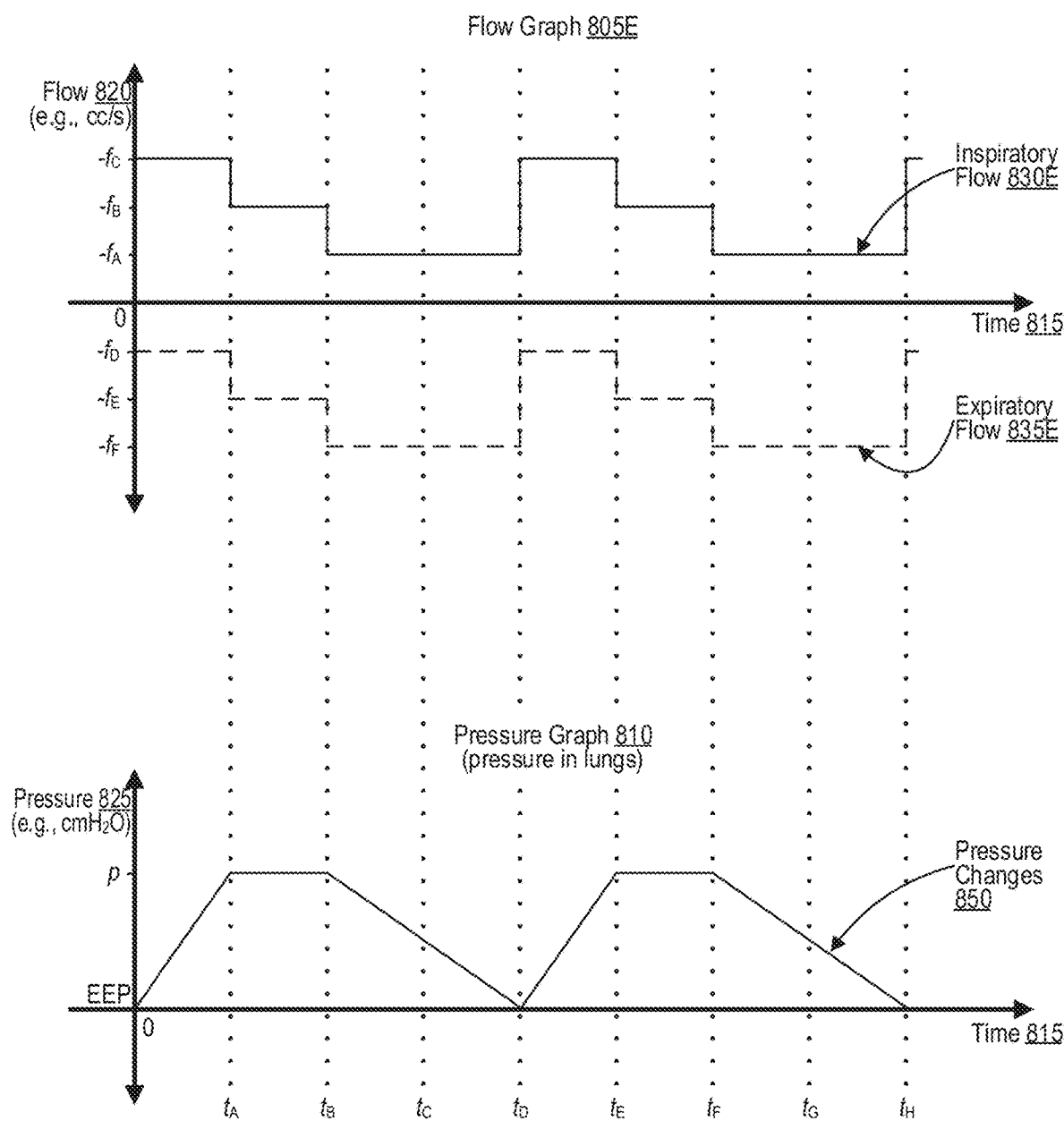

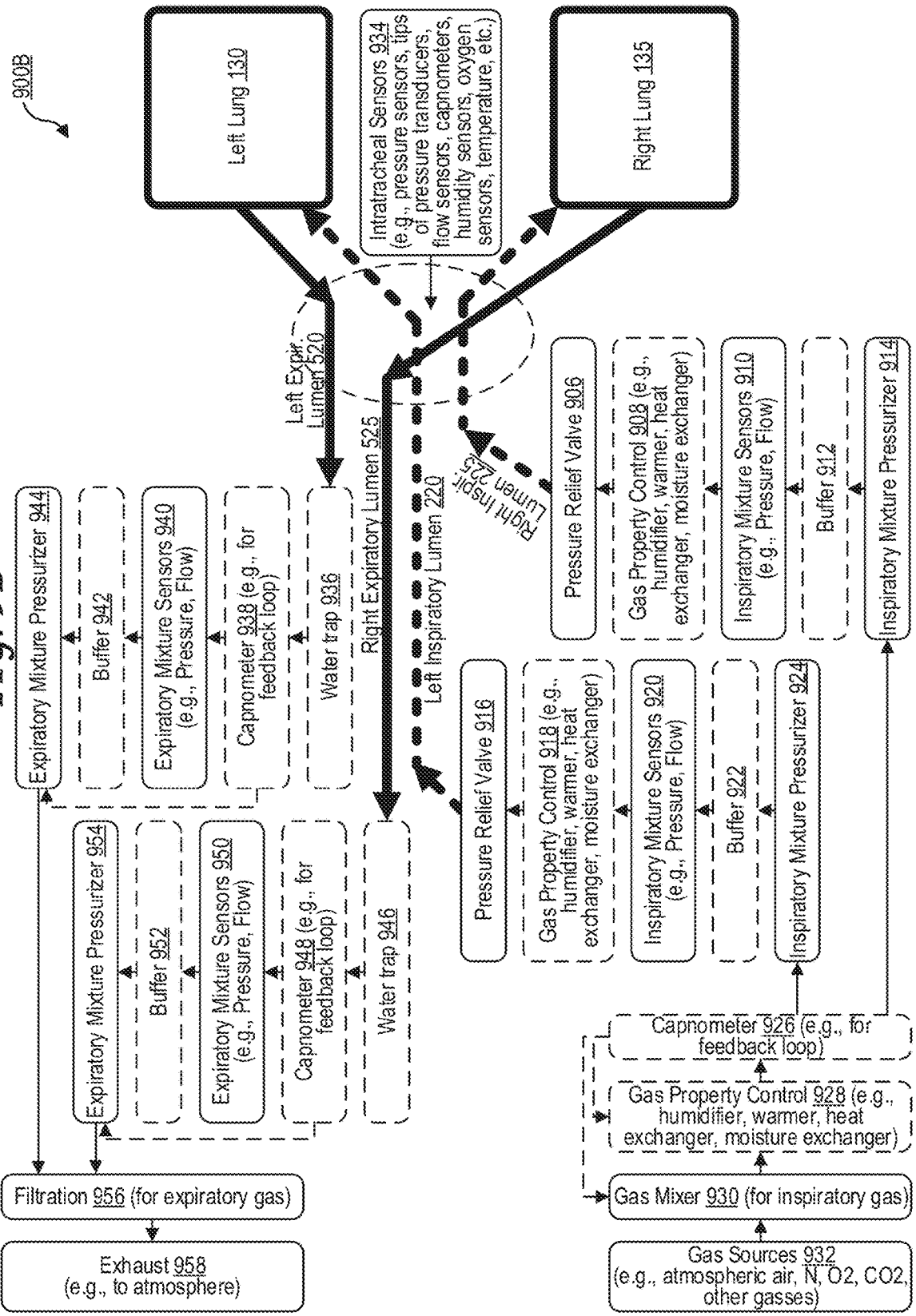

VENTILATOR SYSTEM WITH GAS FLOW CONTROL

CROSS-REFERENCE TO RELATED APPLICATIONS

The present application is a continuation of U.S. patent application Ser. No. 17/345,994 filed Jun. 11, 2021, now U.S. Pat. No. 11,285,286, which claims the priority benefit of U.S. provisional application No. 63/075,327 filed Sep. 8, 2020, U.S. provisional application No. 63/075,555 filed Sep. 8, 2020, and U.S. provisional application No. 63/077,037 filed Sep. 11, 2020, the disclosures of which are all hereby incorporated by reference in their entireties.

BACKGROUND

1. Field

The present teachings are generally related to ventilator systems. More specifically, the present teachings relate to ventilator systems with multiple inspiratory lumens configured so that separate inspiratory lumens provide gas to different portions of a patient's airways, reducing dead space in the patient's airways and reducing risk of cross-infection between the different portions of the patient's airways.

2. Description of the Related Art

A ventilator is life support machine that can be used to assist a patient with breathing. A ventilator generally includes a tube that is inserted into the patient's mouth. A ventilator mechanically provides air into the patient's airways. A ventilator may be used, for example, when a patient is having trouble breathing on their own due to an infection, an injury, a disability, and/or another medical condition.

Dead space represents a volume of ventilated air in a patient's airways that does not # participate in gas exchange. For instance, dead space can represent a volume of air that remains in the patient's airways even after an exhalation, and that is thus not replaced by fresh air from the patient's next inhalation. The average dead space in a healthy individual's airways represent 26% of tidal volume. Respiratory conditions, such as diseases, injuries, or disabilities, can all increase dead space in the airways of patients, for example by impairing a patient's ability to inhale and/or exhale. Disease-causative agents (DCAs) can move throughout dead space in a patient's airways, which can cause infections or other diseases to spread throughout the patient's airways. #DCAs suspended in dead space are generally not accessible to inhaled medications or to the human body's defense systems (e.g., immune cells and antibodies).

SUMMARY

Techniques and systems are described herein for reducing dead space and increasing clearance of dead space in a patient's airways using a ventilator apparatus with multiple inspiratory lumens. The inspiratory lumens are configured so that separate inspiratory lumens provide air to separate lungs and/or bronchi. The ventilator apparatus can also include one or more expiratory lumens to receive and/or evacuate expiratory gases from the patient's airways. The use of separate inspiratory lumens, together with one or more expiratory lumens, can reduce dead space in the patient's airways and increase the clearance of dead space. The use of separate inspiratory lumens, together with one or more expiratory lumens, can thus reduce risk of cross-infection and/or cross-contamination between different parts of the patient's airways, such as cross-infection from one lung to the other and/or cross-infection between bronchi and reinfection of already recovered portions of patient's lungs, with the DCAs suspended in dead space.

In one example, an apparatus for airflow control is provided. The apparatus includes a first inspiratory lumen that is configured to receive a first inspiratory gaseous volume and to provide the first inspiratory gaseous volume to a first portion of an airway of a patient while the first inspiratory lumen is at least partially inserted into the airway. The apparatus includes a second inspiratory lumen that is configured to receive a second inspiratory gaseous volume and to provide the second inspiratory gaseous volume to a second portion of the airway while the second inspiratory lumen is at least partially inserted into the airway. The apparatus includes one or more expiratory lumens that are configured to evacuate an expiratory gaseous volume from at least one of the first portion of the airway and from the second portion of the airway while the one or more expiratory lumens are at least partially inserted into the airway.

In another example, a method for airflow control is provided. The method includes receiving a first inspiratory gaseous volume into a first inspiratory lumen. The method includes providing the first inspiratory gaseous volume to a first portion of an airway of a patient using the first inspiratory lumen while the first inspiratory lumen is at least partially inserted into the airway. The method includes receiving a second inspiratory gaseous volume into a second inspiratory lumen. The method includes providing the second inspiratory gaseous volume to a second portion of the airway using the second inspiratory lumen while the second inspiratory lumen is at least partially inserted into the airway. The method includes evacuating an expiratory gaseous volume from the first portion of the airway and from the second portion of the airway using one or more expiratory lumens while the one or more expiratory lumens are at least partially inserted into the airway.

In another example, an apparatus for airflow control is provided. The apparatus includes means for receiving a first inspiratory gaseous volume into a first inspiratory lumen. The apparatus includes means for providing the first inspiratory gaseous volume to a first portion of an airway of a patient using the first inspiratory lumen while the first inspiratory lumen is at least partially inserted into the airway. The apparatus includes means for receiving a second inspiratory gaseous volume into a second inspiratory lumen. The apparatus includes means for providing the second inspiratory gaseous volume to a second portion of the airway using the second inspiratory lumen while the second inspiratory lumen is at least partially inserted into the airway. The apparatus includes means for evacuating an expiratory gaseous volume from the first portion of the airway and from the second portion of the airway using one or more expiratory lumens while the one or more expiratory lumens are at least partially inserted into the airway.

In another example, a non-transitory computer-readable medium is provided having stored thereon instructions that, when executed by one or more processors, cause the one or more processors to: receive a first inspiratory gaseous volume into a first inspiratory lumen; provide the first inspiratory gaseous volume to a first portion of an airway of a patient using the first inspiratory lumen while the first inspiratory lumen is at least partially inserted into the airway; receive a second inspiratory gaseous volume into a second inspiratory lumen; provide the second inspiratory gaseous volume to a second portion of the airway use the second inspiratory lumen while the second inspiratory lumen is at least partially inserted into the airway; and evacuate an expiratory gaseous volume from the first portion of the airway and from the second portion of the airway using one or more expiratory lumens while the one or more expiratory lumens are at least partially inserted into the airway.

BRIEF DESCRIPTION OF THE FIGURES

FIG. 3 is a conceptual diagram illustrating a trachea connected to a left lung and a right lung;

FIG. 4B is a conceptual diagram illustrating part of the ventilator system of FIG. 4A with the endotracheal tube (ETT) evacuating expiratory gas that includes disease-causative agents (DCAs) from the diseased right lung and the healthy left lung.

FIG. 4C is a conceptual diagram illustrating part of the ventilator system of FIGS. 4A-4B with the endotracheal tube (ETT) providing inspiratory gas that spreads disease-causative agents (DCAs) to more of the diseased right lung and newly introduces the DCAs into the newly-diseased left lung;

FIG. 4D is a conceptual diagram illustrating an example of the ventilator systems of FIGS. 4A-4C with an adapter added on one side of the balloon and another adapter added on the other side of the balloon;

FIG. 4E is a conceptual diagram 400E illustrating a cross-section of a micro-filter adapter;

FIG. 5A is a conceptual diagram illustrating part of a ventilator system with an endotracheal tube (ETT) that includes an expiratory lumen that evacuates expiratory gas, a left inspiratory lumen that provides inspiratory gas to the left primary bronchus and left lung, and a right inspiratory lumen that provides inspiratory gas to the right primary bronchus and right lung;

FIG. 5B is a conceptual diagram illustrating part of the ventilator system of FIG. 5A where the right lung is diseased and the left lung is healthy;

FIG. 5D is a conceptual diagram illustrating part of a ventilator system with an endotracheal tube (ETT) that includes an inspiratory lumen that provides inspiratory gas, a left expiratory lumen that evacuates expiratory gas from the left primary bronchus and left lung, and a right expiratory lumen that evacuates expiratory gas from the right primary bronchus and right lung;

FIG. 6 is a conceptual diagram illustrating part of a ventilator system with an endotracheal tube (ETT) that includes an expiratory lumen that evacuates expiratory gas, a left inspiratory lumen that provides inspiratory gas, and a right inspiratory lumen that provides inspiratory gas;

FIG. 7A is a conceptual diagram illustrating a cross-section of an endotracheal tube (ETT) that includes an expiratory lumen that evacuates expiratory gas, a left inspiratory lumen that provides inspiratory gas, and a right inspiratory lumen that provides inspiratory gas;

FIG. 7B is a conceptual diagram illustrating a cross-section of a tube that includes a first lumen and a second lumen separated by a membrane;

FIG. 8B is a graph diagram illustrating inspiratory flow, expiratory flow, and pressure changes over time in a ventilator system according to a second illustrative example;

FIG. 8C is a graph diagram illustrating inspiratory flow, expiratory flow, and pressure changes over time in a ventilator system according to a third illustrative example;

FIG. 8E is a graph diagram illustrating inspiratory flow, expiratory flow, and pressure changes over time in a ventilator system according to a fifth illustrative example;

FIG. 9B is a block diagram illustrating an architecture of an exemplary ventilator system that includes a left inspiratory control system that provides inspiratory gas to a left lung through a left inspiratory lumen, a right inspiratory control system that provides inspiratory gas to a right lung through a right inspiratory lumen, a left expiratory control system that evacuates expiratory gas from a left lung through a left expiratory lumen, and a right expiratory control system that evacuates expiratory gas from a right lung through a right expiratory lumen;

DETAILED DESCRIPTION

Figure 1:
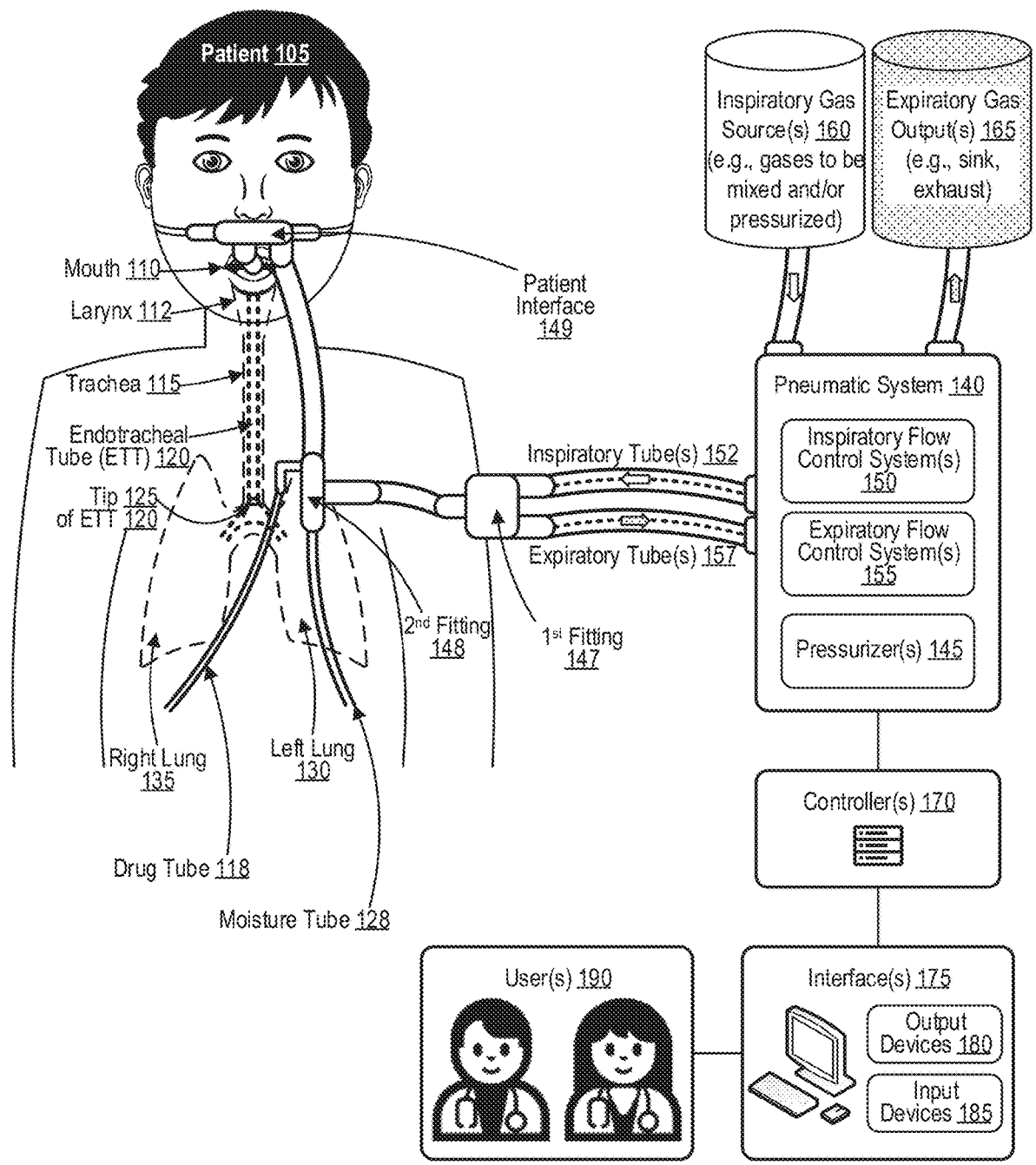
FIG. 1 is a conceptual diagram illustrating a front view of a ventilator system connected to a patient.

A ventilator is a life support machine that can be used to assist a patient with breathing. A ventilator generally includes an endotracheal tube that is inserted via mouth into the patient's trachea. A ventilator can mechanically provide an inspiratory gas into the patient's airways. A ventilator can mechanically evacuate an expiratory gas from the patient's airways. A ventilator may be used, for example, when a patient is having trouble breathing on their own due to an infection, an injury, a disease, a physical handicap, a physical disability, weakness, sedation, use of paralyzing anesthetics, another medical condition, another physical condition, another anatomical condition, or a combination thereof.

A patient's lungs and airways can become infected with and/or otherwise affected by a disease-causative agent (DCA). DCAs can include, for example, bacteria, fungi, viruses (e.g., virions, viral agents), parasites, protozoa, helminths, prions, toxins, synthetic toxicants, physical contaminants, chemical contaminants, biological contaminants, radiological contaminants, portions of a patient's immune system in patients that have an autoimmune disease, other antigens or hazards, or combinations thereof. Diseases can include infections, injuries, poisonings, disabilities, disorders, syndromes, infections, isolated symptoms, deviant behaviors, atypical, aberrant and pathologic variations of structure and function, or combinations thereof. Certain types of DCAs can be referred to as infection agents, toxins, antigens, antibodies, cells, prions, infection vectors, disease agents, disease vectors, microorganisms, microbes, pathogens, germs, contaminants, chemicals, or combinations thereof.

Dead space represents a volume of ventilated air in a patient's airways that does not # participate in alveolar gas exchange. For instance, dead space can represent a volume of air that remains in the patient's airways even after an exhalation. The average dead space in a healthy individual's airways represent 26% of tidal volume. Tidal volume represents the volume of gas inspired with breath. Average tidal volume is 450 milliliters (ml), so average dead space is 117 milliliters (mL). Diseases, such as respiratory diseases, and pathologic conditions, such as being ventilated on mechanical ventilator with high respiratory rate, as commonly required per treatment protocols, can cause a significant increase in dead space in the airways of patients, for example because a patient's ability to inhale and/or exhale may be impaired. DCAs can freely move, or float, or move throughout dead space in a patient's airways. This movement of DCAs within the dead space can facilitate spreading of the diseases from contaminated to uncontaminated yet portions of respiratory system, also to uncontaminated portions of lungs. DCAs suspended in the dead space are generally not accessible to other than inhaled medications, circulating antibodies, immune cells, or other immune response mechanisms of the patient.

The SARS-CoV-2 virus is an example of a disease-causative agent (DCA). COVID-19 is an example of a disease that can be caused by the SARS-CoV-2 virus. During the COVID-19 pandemic, ventilators have been used to treat most severely sick patients with COVID-19 infections. According to some news reports during the COVID-19 pandemic, some patients' conditions appeared to worsen after the patient was connected to a ventilator. In some examples, the disease spread throughout a patient's airways after the patient was connected to a ventilator. In some cases, patients can get reinfected with COVID-19, sometimes weeks after their first COVID-19 infection. In some patients, portions of the lungs can get reinfected with COVID-19 while the patient is on a ventilator, even during a first-in-lifetime COVID-19 infections. Furthermore, in at least some patients, intravenous provision of antibodies can be beneficial only before patient present significant lungs disease and before patients end up on ventilator. Once such a patient is on a ventilator, antibodies provide limited effect, for instance because the dead space in the patient's lungs is already filled with DCAs, the antibodies cannot reliably reach the DCAs suspended in the dead space, and the effectiveness of such therapies is lost.

Systems and techniques are described herein that minimize or reduce the risk of infection and/or reinfection of patients' lungs (and/or other portions of the patients' airways) while patients are on a ventilator by clearing and reducing the dead space in the patients' lungs. Once a patient ends up on a ventilator, the only remaining treatments may have very limited effectiveness, so any improvements to the functioning of the ventilator, such as improved ability to clear DCAs from the patient's airways mechanically and/or to reduce dead space, may significantly improve patient outcomes and save lives. By preventing patients' conditions from getting significantly worse, improvements to ventilators can also expand the treatments that will be available and effective for patients, for example allowing antibody treatments to be effective for a longer period of time for COVID-19 patients. Such improvements can also help patients with any lung disease or airway issue caused by any DCA, even empirically caused by unknown DCAs.

FIG. 1 is a conceptual diagram 100 illustrating a front view of a ventilator system connected to a patient 105. The airway of the patient 105 includes at least the patient 105's mouth 110, larynx 112, trachea 115, bronchi (not pictured), left lung 130, and right lung 135. The ventilator system includes an endotracheal tube (ETT) 120 that is inserted into the mouth 110 of the patient 105 and into the patient 105's trachea 115, alongside the patient 105's larynx 112. The ETT 120 ends in a tip 125 of the ETT 120 within the trachea 115. Additional dashed tubes are illustrated extending beyond the tip 125 of the ETT 120 partway into the left lung 130 and right lung 135, and may represent inspiratory lumens (e.g., left inspiratory lumen 220, right inspiratory lumen 225) and/or expiratory lumens (e.g., left expiratory lumen 520, right expiratory lumen 525) as discussed further herein. The ETT 120 is kept in position through a patient interface 149, which can be mechanically coupled to the patient 105 using one or more coupling mechanisms of the patient interface 149, such as one or more rubber bands, one or more clamps, one or more clips, one or more fasteners, or a combination thereof. The ETT 120 provides inspiratory gas (e.g., clean air) to the left lung 130 and right lung 135 of the patient. The ETT 120 receives and evacuates expiratory gas (e.g., exhaled air) from the left lung 130 and right lung 135 of the patient 105.

The ventilator system includes a pneumatic system 140 with a pressurizer 145 (e.g., compressor and/or decompressor), an inspiratory flow control system 150, and an expiratory flow control system 155. The inspiratory flow control system 150 provides flow of inspiratory gas(es) from one or more inspiratory gas sources 160, through an inspiratory tube 152, through a first fitting 147 (e.g., a wye-fitting), through a second fitting 148, through a patient interface 149, through the ETT 120, and/or into the airway of the patient 105. In some examples, the inspiratory flow control system 150 can mix inspiratory gases from the one or more inspiratory gas sources 160. For example, the one or more inspiratory gas sources 160 can include an oxygen ($O_2$) gas source, a nitrogen (N) gas source, a carbon dioxide ($CO_2$) gas source, an argon (Ar) gas source, one or more gas sources for one or more drugs (in gaseous and/or aerosolized form), one or more gas sources for one or more other elemental gases, one or more gas sources for one or more other molecular gases, an pre-mixed atmospheric gas source, or a combination thereof. For example, the inspiratory flow control system 150 can mix oxygen ($O_2$), nitrogen (N), carbon dioxide ($CO_2$), argon (Ar), one or more drugs (in gaseous and/or aerosolized form), one or more one or more other elemental gases, one or more other molecular gases, a pre-mixed atmospheric gas source, or a combination thereof.

Even though it may seem counter-intuitive to include carbon dioxide ($CO_2$) in the inspiratory gas mixture, it may be useful to include carbon dioxide ($CO_2$) in the inspiratory gas mixture when carbon dioxide ($CO_2$) is being evacuated in excess from the patient 105's airways, as lack of carbon dioxide ($CO_2$) can increase alkalinity, pushing pH too high, and can cause negative effects such as alkalosis. Some types of ventilator systems, such as those illustrated in FIGS. 4A-4C, might not evacuate enough carbon dioxide ($CO_2$) to necessitate or benefit significantly from inclusion of carbon dioxide ($CO_2$) in the inspiratory gas mixture. Other types of ventilator systems that regularly and actively evacuate expiratory airflow, such as those illustrated in or discussed with respect to FIGS. 2, 5A-5C, 6, 7A-7B, 8A-8E, 9A-9B, and 10, can evacuate enough carbon dioxide ($CO_2$) that inclusion of carbon dioxide ($CO_2$) in the inspiratory gas mixture may be necessary and/or significantly beneficial to reduce alkalinity and prevent alkalosis or other negative effects.

In some examples, the inspiratory flow control system 150 can mix one or more liquids and/or one or more particulate solids into the one or more gases, for example in aerosolized form. The one or more liquids can include water ($H_2O$), one or more drugs in liquid form, one or more other liquids, or a combination thereof. The one or more particulate solids can include one or more drugs in particulate solid form, one or more other particulate solids, or a combination thereof. The inspiratory flow control system 150 can include an aerosolizer and/or particulatizer to aerosolize and/or particulatize the one or more liquids and/or the one or more solids. The inspiratory flow control system 150 can mix the one or more aerosolized and/or particulate liquids and/or solids into the one or more inspiratory gases.

The inspiratory flow control system 150 can mix gases and/or liquids and/or particulate solids from the one or more inspiratory gas sources 160 at one or more predetermined ratios and/or proportions. The inspiratory flow control system 150 can mix inspiratory gases and/or liquids and/or particulate solids from the one or more inspiratory gas sources 160 at one or more predetermined ratios and/or proportions to simulate the natural ratios and/or proportions of these gases in Earth's atmosphere or other ratios and/or proportions that may be selected or recommended by an operator, by an artificial intelligence algorithm (e.g., one or more trained machine learning models, one or more trained neural networks, or a combination thereof), or a combination thereof. The inspiratory flow control system 150 can mix inspiratory gases from the one or more inspiratory gas sources 160 at one or more predetermined ratios and/or proportions that increase or decrease a relative quantity of one or more specific gases (e.g., increased oxygen and/or decreased carbon monoxide) relative to the natural ratios and/or proportions of these gases in Earth's atmosphere or other ratios and/or proportions that may be selected or recommended by an operator, by an artificial intelligence algorithm (e.g., one or more trained machine learning models, one or more trained neural networks, or a combination thereof), or a combination thereof. The mixture mixed by the inspiratory flow control system 150 can be referred to as the inspiratory mixture, the inspiratory gas, the inspiratory substance, the inspiratory air, or some combination thereof.

In some examples, some of the mixing and/or modifications to gas properties described above with respect to the inspiratory flow control system 150 can occur between the inspiratory tube 152 and the ETT 120. In some examples, some of the mixing and/or modifications to gas properties described above with respect to the inspiratory flow control system 150 can occur at the first fitting 147, at the second fitting 148, and/or at the patient interface 149. For example, a drug tube 118 is illustrated in FIG. 1 going into the second fitting 148. The drug tube 118 can provide one or more drugs from one or more drug sources (e.g., one or more of the one or more inspiratory gas sources 160) to the inspiratory gas provided through the ETT 120 to the patient 105's airways. The one or more drugs can include, for example, anesthetics, drugs for treating an injury, drugs for treating a disability, a drugs for treating a disease (e.g., a respiratory disease and/or any other disease discussed herein), and/or drugs for treating symptoms of a disease (e.g., a respiratory disease and/or any other disease discussed herein), bronchodilators, or a combination thereof.

The inspiratory flow control system 150 can control various properties of the inspiratory gas, such as temperature and/or humidity. The inspiratory flow control system 150 can include a warmer and/or a heat exchanger to control (e.g., increase or decrease) the temperature of the inspiratory gas before the inspiratory flow control system 150 provides the inspiratory gas to the patient 105's airways through the inspiratory tube 152, through the first fitting 147, through the second fitting 148, through the patient interface 149, and/or through the ETT 120. The inspiratory flow control system 150 can include a humidifier and/or a moisture exchanger and/or a moisture trap to control (e.g., increase or decrease) the humidity of the inspiratory gas before the inspiratory flow control system 150 provides the inspiratory gas to the patient 105's airways through the inspiratory tube 152, through the first fitting 147, through the second fitting 148, through the patient interface 149, and/or through the ETT 120. The inspiratory flow control system 150 can control properties such as temperature and/or humidity before mixing inspiratory gases/liquids/solids, after mixing inspiratory gases/liquids/solids, or both.

The inspiratory flow control system 150 can include one or more filters that filter out the contaminants from the inspiratory gas before the inspiratory flow control system 150 provides the inspiratory gas to the patient 105's airways through the inspiratory tube 152, through the first fitting 147, through the second fitting 148, through the patient interface 149, and/or through the ETT 120. The inspiratory flow control system 150 can filter the inspiratory air before mixing inspiratory gases/liquids/solids, after mixing inspiratory gases/liquids/solids, or both.

In some examples, the inspiratory flow control system 150 can include one or multiple inspiratory lumens that provide inspiratory gas to both lungs or separately provide inspiratory gas to different portions of the patient 105's airways. For instance, the inspiratory flow control system 150 can include a first inspiratory lumen and a second inspiratory lumen. The multiple inspiratory lumens can include a left inspiratory lumen 220 and a right inspiratory lumen 225 as illustrated in, and/or described with respect to, FIGS. 2, 5A, 5B, 6, 9A, and/or 9B. In some examples with at least 2 inspiratory lumens, as illustrated on FIG. 9B, the inspiratory flow control system 150 can include a pressure relief valve 906, a gas property control 908, inspiratory mixture sensors 910, a buffer 912, an inspiratory mixture pressurizer 914, a pressure relief valve 916, a gas property control 918, inspiratory mixture sensors 920, a buffer 922, an inspiratory mixture pressurizer 924, a capnometer 926, a gas property control 928, a gas mixer 930, or a combination thereof.

The expiratory flow control system 155 receives flow of expiratory gas(es) from the patient 105's airways, through the ETT 120, through the patient interface 149, through the second fitting 148, through the first fitting 147, through an expiratory tube 157, and/or transfers expiratory gas(es) into one or more expiratory gas outputs 165. The one or more expiratory gas outputs 165 can include a sink (e.g., a reservoir), an exhaust, or both. For example, if the expiratory gas is from a patient whose airways include disease-causative agents that might cause disease in others in the area (e.g, doctors, nurses other patients), the one or more expiratory gas outputs 165 can include a sink (e.g., a reservoir) to trap the expiratory gas(es) within. If the disease-causative agents can be reliably filtered out using one or more filters, the one or more expiratory gas outputs 165 can include the one or more filters and/or an exhaust.

In some examples, the expiratory flow control system 155 includes a suction device that provides suction from the patient 105's airway through the ETT 120 and expiratory tube 157. The compressor(s) and/or pressurizer(s) 145 can provide gas compression and/or pressure that can provide the suction for the suction device of the expiratory flow control system 155. In some examples, the expiratory flow control system 155 does not include or does not activate its suction device, and instead receives expiratory flow from the airways of the patient 105 based on the airflow provided by patient 105's own exhalations. In some examples, the expiratory flow control system 155 receives the expiratory partially using suction from the suction device and partially using airflow provided by patient 105's own exhalations, for example if patient 105 is passively exhaling during the expiration, but with not enough flow rate to provide sufficient exhalation, or if the patient 105 is breathing on their own but too weakly to provide sufficient exhalation.

In some examples, the expiratory flow control system 155 filters out and/or traps one or more liquids (e.g., aerosolized liquids), one or more solids (e.g., particulate solids), or a combination thereof. The expiratory flow control system 155 can filters out and/or traps the liquids and/or solids using one or more filters, one or more moisture traps, or a combination thereof. For example, a moisture tube 128 is illustrated coming from the second fitting 148, which may output liquid collected by a moisture trap within the second fitting 148. In some examples, the moisture tube 128 can output to an expiratory gas output 165 (e.g., sink or exhaust).

The expiratory flow control system 155 can control various properties of the expiratory gas, such as temperature and/or humidity. The expiratory flow control system 155 can include a warmer and/or a heat exchanger to control (e.g. increase or decrease) the temperature of the expiratory gas. The expiratory flow control system 150 can include a humidifier and/or a moisture exchanger and/or a moisture trap to control (e.g. increase or decrease) the humidity of the expiratory gas. The expiratory flow control system 155 can include one or more filters that filter out the contaminants (such as disease-causative agents) from the expiratory gas.

In some examples, the expiratory flow control system 155 can include multiple expiratory lumens that separately receive expiratory gas from different portions of the patient 105's airways. For instance, the inspiratory flow control system 150 can include a first expiratory lumen and a second expiratory lumen. The multiple expiratory lumens can include a left expiratory lumen 520 and a right inspiratory lumen 525 as illustrated in, and/or described with respect to, FIGS. 5C and 9B. In some examples, the expiratory flow control system 155 can include a water trap 936, a capnometer 938, expiratory mixture sensors 940, a buffer 942, an expiratory mixture pressurizer 944, a water trap 946, a capnometer 948, expiratory mixture sensors 950, a buffer 952, an expiratory mixture pressurizer 954, a filtration system 956, or a combination thereof.

The pressurizer(s) 145 can be used to compress and/or pressurize the inspiratory gas (e.g., the mixture of inspiratory gases from the inspiratory gas sources 160) before providing the inspiratory gas compressed and/or pressurized to the patient 105's airways through the ETT 120. The pressurizer(s) 145 can compress and/or pressurize the inspiratory gas within a buffer chamber. The pressurizer(s) 145 can be used to compress, decompress, pressurize, and/or depressurize expiratory gas, for example to provide suction as part of a suction device.

The ventilation system can include one or more controllers 170. The one or more controllers 170 can each include one or more computing systems 1100. For examples, the one or more controllers 170 can each include one or more processors 1110, one or more memory units (e.g., ROM 1120, RAM 1125), one or more storage devices 1130, one or more input devices 1145, one or more output devices 1135, one or more communication interfaces 1140, or a combination thereof. In some examples, the one or more controllers 170 can receive sensor data from one or more sensors of the ventilator system, such as one or more capnometers 926/938/948, one or more inspiratory mixture sensors 910/920, one or more expiratory mixture sensors 940/950, or a combination thereof and/or other sensors (not shown on pictures) used in clinical practice like oxygen saturation of patient's blood, patient's blood pressure, ECG curve, temperature, central line catheter transducer, video camera, microphone, or a combination thereof. In some examples, the one or more controllers 170 can analyze the sensor data from the one or more sensors and one or more capnometers of the ventilator system, for example to compare the sensor data to one or more predetermined thresholds or ranges that the one or more controllers 170 can trigger actions based on. In some examples, the one or more controllers 170 can analyze the sensor data from the one or more sensors of the ventilator system to identify one or more patterns that the one or more controllers 170 can trigger actions based on. Actions that can be triggered can include, for example, modifying inspiratory airflow pressure, modifying inspiratory airflow patterns (e.g., between inspiratory flows 830A-830E), modifying expiratory airflow pressure (e.g., expiratory suction), modifying expiratory airflow patterns (e.g., between expiratory flows 835A-835E), or a combination thereof.

The ventilation system can include one or more interfaces 175 for the one or more controllers 170. The one or more interfaces 175 can include one or more output devices 180, which can include one or more display screens, one or more indicator lights (e.g., light emitting diodes (LEDs)), one or more speakers, one or more headphones, one or more output devices 1135, or a combination thereof. The one or more output devices 180 also include connectors that can be used to connect the one or more controllers 170 to one or the previously-listed types of output devices 180, such as plugs, ports, jacks, wires, and/or wireless transceivers. The one or more output devices 180 can output data to one or more users 190, such as sensor data from the one or more sensors of the ventilator system, indicators that the sensor data has exceeded a threshold, indicators that the sensor data has fallen below a threshold, indicators that the sensor data has crossed into a predetermined range, indicators that the sensor data has crossed out of a predetermined range, indications of one or more patterns recognized in the sensor data by the one or more controllers 170, or a combination thereof.

The one or more interfaces 175 can include one or more input devices 185, which can include one or more touchscreens, keyboards, keypads, mouse pointers, trackpads, trackballs, microphones, cameras, one or more input devices 1145, or a combination thereof. The one or more input devices 185 also include connectors that can be used to connect the one or more controllers 170 to one or the previously-listed types of input devices 185, such as plugs, ports, jacks, wires, and/or wireless transceivers. The one or more input devices 185 can receive input data from one or more users 190, such as input data identifying a threshold, a range, an inspiratory airflow pattern to use (e.g., one of inspiratory flows 830A-830E), an inspiratory airflow pattern to use (e.g., one of expiratory flows 835A-835E), or a combination thereof.

In some examples, a ventilator system may include multiple inspiratory flow control systems 150, multiple expiratory flow control systems 152, multiple pressurizers 145, multiple controllers 170, multiple inspiratory tubes 152, multiple expiratory tubes 157, or a combination thereof. In an illustrative example, the inspiratory flow control systems 150 of the ventilator system may include a left inspiratory flow control system and a right inspiratory flow control system. The left inspiratory flow control system can mix an inspiratory mixture for, and/or provides the inspiratory mixture to, the left lung 130 of the patient, in some examples through a left inspiratory tube of the inspiratory tubes 152 and/or through a left inspiratory lumen (e.g., left inspiratory lumen 220). In some examples, a left pressurizer of the multiple pressurizers 145 can provide pressure to provide the inspiratory mixture from the left inspiratory flow control system to the left lung 130 of the patient. In some examples, a left controller of the multiple controllers 170 can control inspiratory pressure, inspiratory mixture components, inspiratory mixture component ratios, and/or other aspects of provision of the inspiratory mixture from the left inspiratory flow control system to the left lung 130. The right inspiratory flow control system can mix an inspiratory mixture for, and/or provides the inspiratory mixture to, the right lung 135 of the patient, in some examples through a right inspiratory tube of the inspiratory tubes 152 and/or through a right inspiratory lumen (e.g., right inspiratory lumen 225). In some examples, a right pressurizer of the multiple pressurizers 145 can provide pressure to provide the inspiratory mixture from the right inspiratory flow control system to the right lung 135 of the patient. In some examples, a right controller of the multiple controllers 170 can control inspiratory pressure, inspiratory mixture components, inspiratory mixture component ratios, and/or other aspects of provision of the inspiratory mixture from the right inspiratory flow control system to the right lung 135. The inspiratory tube(s) 152 are illustrated as a single tube with a dashed line dividing the single tube into two tubes. The single tube represents that the inspiratory tube(s) 152 can be a single tube, while the dashed line division represents that the inspiratory tube(s) 152 can include a left inspiratory tube and a right inspiratory tube as discussed above.

In an illustrative example, the expiratory flow control systems 155 of the ventilator system may include a left expiratory flow control system and a right expiratory flow control system. The left expiratory flow control system can receive an expiratory mixture from, and/or suction the expiratory mixture from, the left lung 130 of the patient, in some examples through a left expiratory tube of the expiratory tubes 157 and/or through a left expiratory lumen (e.g., left expiratory lumen 520). In some examples, a left pressurizer of the multiple pressurizers 145 can provide negative pressure to pull, extract, and/or suction the expiratory mixture from the left expiratory flow control system from the left lung 130 of the patient 105 to the expiratory gas output(s) 165. In some examples, a left controller of the multiple controllers 170 can control expiratory negative pressure and/or other aspects of receipt of the expiratory mixture from the left lung 130 to the expiratory gas output(s) 165. The right expiratory flow control system can receive an expiratory mixture from, and/or suction the expiratory mixture from, the right lung 130 of the patient, in some examples through a right expiratory tube of the expiratory tubes 157 and/or through a right expiratory lumen (e.g., right expiratory lumen 525). In some examples, a right pressurizer of the multiple pressurizers 145 can provide negative pressure to pull, extract, and/or suction the expiratory mixture from the right expiratory flow control system from the right lung 135 of the patient 105 to the expiratory gas output(s) 165. In some examples, a right controller of the multiple controllers 170 can control expiratory negative pressure and/or other aspects of receipt of the expiratory mixture from the right lung 135 to the expiratory gas output(s) 165. The expiratory tube(s) 157 are illustrated as a single tube with a dashed line dividing the single tube into two tubes. The single tube represents that the expiratory tube(s) 157 can be a single tube, while the dashed line division represents that the expiratory tube(s) 157 can include a left expiratory tube and a right expiratory tube as discussed above.

Figure 2:
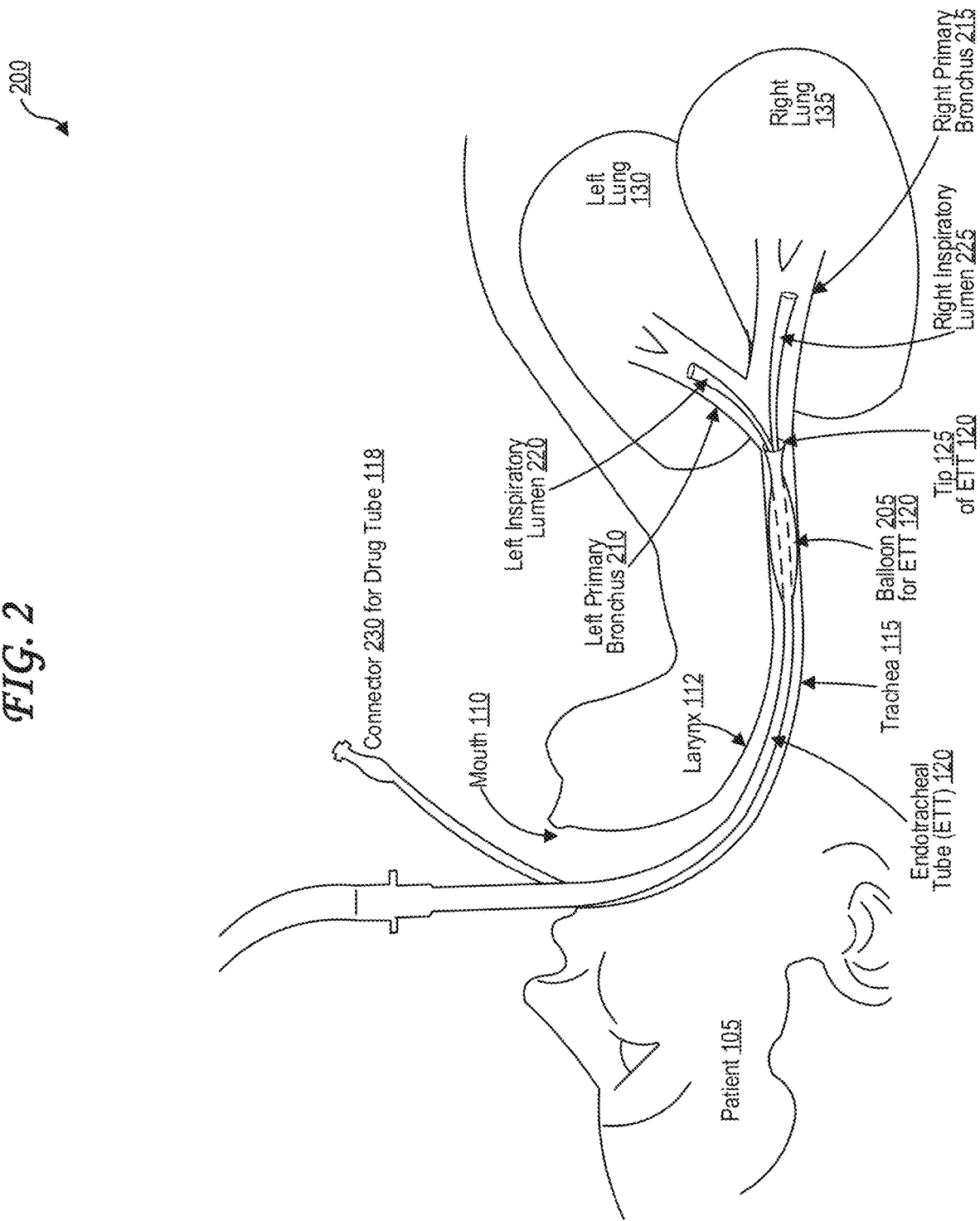
FIG. 2 is a conceptual diagram illustrating a side view of a ventilator system connected to a patient.

FIG. 2 is a conceptual diagram 200 illustrating a side view of a ventilator system connected to a patient 105. The side view illustrates the ETT 120 entering the patient 105's mouth 110, passing along the patient 105's larynx 112, and passing into and/or through at least a portion of the patient 105's trachea 115. The ventilator system includes a connector 230 to which a drug tube 118 can be connected.

The ventilator system includes a balloon 205 for the ETT 120. The balloon 205 inflates once the ETT 120 is in the trachea 115. The balloon 205, once inflated, secures the ETT 120 in position in the trachea 115. The balloon 205, once inflated, can protect the ETT 120 from scraping the walls of, colliding with the walls of, or otherwise injuring the trachea 115. The balloon 205, once inflated, can prevent airflow from passing through the trachea 115 other than through the ETT 120.

The ventilator system includes multiple inspiratory lumens that provide inspiratory gas(es) to different portions of the patient 105's airways. In particular, the ventilator system of FIG. 2 includes a left inspiratory lumen 220 and a right inspiratory lumen 225. The left inspiratory lumen 220 and the right inspiratory lumen 225 pass through the ETT 120 and extends beyond the tip 125 of the ETT 120, further into the patient 105's airways. The left inspiratory lumen 220 extends toward and/or into the left primary bronchus 210 and/or the left lung 130 of the patient 105. The right inspiratory lumen 225 extends toward and/or into the right primary bronchus 215 and/or the right lung 135 of the patient 105.

FIG. 3 is a conceptual diagram 300 illustrating a trachea 115 connected to a left lung 130 and a right lung 135. The trachea 115, as illustrated in FIG. 3, starts from a point below the larynx 112 (not pictured). The trachea 115, as it extends toward the left lung 130 and the right lung 135, branches into the left primary bronchus 210 and the right primary bronchus 215. The left primary bronchus 210 conducts airflow between the trachea 115 and the left lung 130. The right primary bronchus 215 conducts airflow between the trachea 115 and the right lung 135. The primary bronchi can branch into further, smaller bronchi. For example, the left primary bronchus 210 branches into three left secondary bronchi 310. The right primary bronchus 215 branches into three right secondary bronchi 315. The secondary bronchi may be referred to as lobar bronchi. Each secondary bronchus of the left secondary bronchi 310 and/or right secondary bronchi 315 can branch off further into narrower tertiary bronchi or segmental bronchi. #Further divisions of the segmental bronchi are known as 4th order segmental bronchi, 5th order segmental bronchi, 6th order segmental bronchi, and so forth, or may be referred to as subsegmental bronchi.

Bronchi may branch into smaller bronchioles 320, which themselves may branch into further bronchioles 320. Some bronchioles 320, referred to as respiratory bronchioles 320, end in alveoli 325 that include alveolar ducts and alveolar sacs. The alveoli may include surface epithelial cells referred to as pneumocytes. If a patient 105 has a disease, alveoli 325 in the left lung 130 and/or alveoli 325 in right lung 135 can become infected with disease-causative agents (DCAs) such as viruses or bacteria. In some examples, if a patient 105 has a disease, pneumocytes of the alveoli 325 can become infected by certain DCAs such as viruses or bacteria.

Figure 4A:
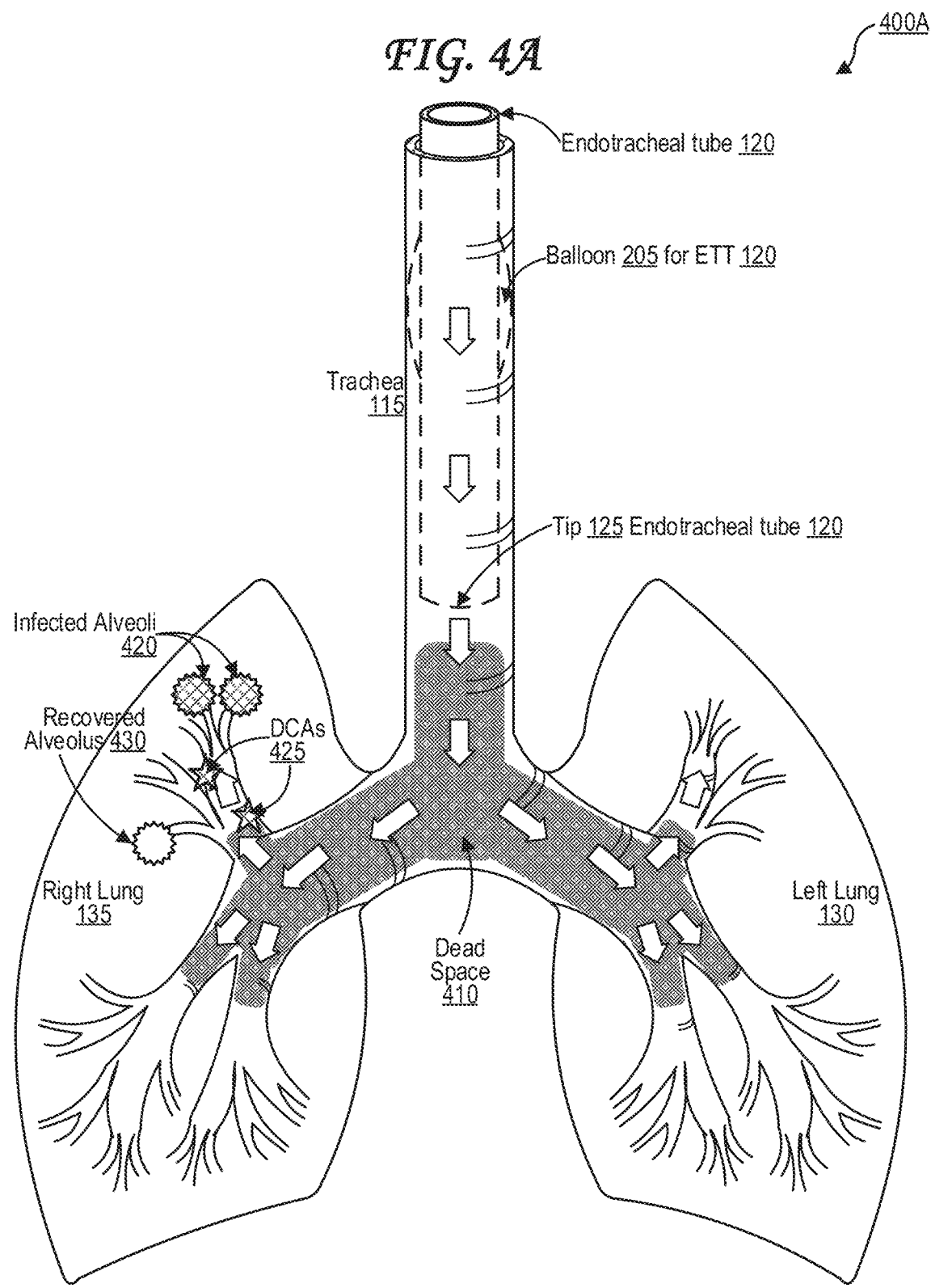
FIG. 4A is a conceptual diagram illustrating part of a ventilator system with an endotracheal tube (ETT) in a trachea providing inspiratory gas into a diseased right lung and a healthy left lung.

FIG. 4A is a conceptual diagram 400A illustrating part of a ventilator system with an endotracheal tube (ETT) 120 in a trachea 115 providing inspiratory gas into a diseased right lung 135 and a healthy left lung 130. The ventilator system includes a balloon 205 for the ETT 120. The balloon 205 is illustrated in its inflated state, in which the balloon 205 secures the ETT 120 in position in the trachea 115, protects the trachea 115 from being damaged by the ETT 120, and/or prevent airflows from passing through the trachea 115 other than through the ETT 120.

A shaded area within part of the trachea 115 and some of the bronchi represents the dead space 410 with limited gas exchange or no gas exchange. The dead space 410 covers a significant portion of the left primary bronchus 210 and the right primary bronchus 215, for instance. The dead space 410 covers at least some of the left secondary bronchi 310 and/or right secondary bronchi 315. In some examples, the dead space 410 can also include certain segmental bronchi, subsegmental bronchi, bronchioles 320, and/or alveoli 325.

The right lung 135 of FIG. 4A includes two infected alveoli 420 and a recovered alveolus 430. The two infected alveoli 420 are each illustrated as white-colored 16-point starburst shape that are shaded with a black crosshatch pattern and outlined in black. The recovered alveolus 430 is illustrated as a white-colored 16-point starburst shape that is outlined in black. The two infected alveoli 420 may be infected with a disease caused by DCAs 425. As noted above, DCAs 425 can include, for example, bacteria, fungi, viruses (e.g., virions), parasites, protozoa, helminths, prions, toxins, synthetic toxicants, physical contaminants, chemical contaminants, biological contaminants, radiological contaminants, portions of a patient's immune system that have an autoimmune disease, or combinations thereof. Diseases can include infections, injuries, disabilities, disorders, syndromes, infections, isolated symptoms, deviant behaviors, atypical, aberrant, or pathologic variations of structure and function, or combinations thereof. The recovered alveolus 430 may have previously been an infected alveolus that has since recovered from the disease and/or no longer harbors DCAs 425. Two example DCAs 425 are also illustrated in secondary and tertiary bronchi of the right lung 135 near the infected alveoli 420. The DCAs 425 are illustrated as white-colored 5-point star shapes that are shaded with a black crosshatch pattern and outlined in black.

The ETT 120, as illustrated in FIG. 4A, is providing an inspiratory gas to the patient 105's airways. An exemplary flow of the inspiratory gas down the ETT 120 and into and through the bronchi of the left lung 130 and the right lung 135 is illustrated using white arrows outlined in black. Because the DCAs 425 in the bronchi are largely clustered close to the infected alveoli 420 in FIG. 4A, the flow of inspiratory gas in FIG. 4A might spread the DCAs 425 to certain segmental bronchi, subsegmental bronchi, bronchioles 320, and/or alveoli 325 that are close to the infected alveoli 420. Because the DCAs 425 in the bronchi are largely clustered close to the infected alveoli 420 in FIG. 4A, the flow of inspiratory gas in FIG. 4A is unlikely to spread the DCAs 425 from the right lung 135 to the left lung 130, or otherwise to portions of the patient 105's airway (e.g., bronchi, bronchioles 320, and/or alveoli 325) that are far away from the infected alveoli 420 in FIG. 4A.

FIG. 4B is a conceptual diagram 400B illustrating part of the ventilator system of FIG. 4A with the endotracheal tube (ETT) 120 evacuating expiratory gas that includes disease-causative agents (DCAs) 425 from the diseased right lung 135 and the healthy left lung 130 during the expiration. The right lung 135 of FIG. 4B includes the two infected alveoli 420 of FIG. 4A and the recovered alveolus 430 of FIG. 4A.

The ETT 120, as illustrated in FIG. 4B, is receiving and/or evacuating an expiratory gas from the patient 105's airways. An exemplary flow of the expiratory gas up the ETT 120 and from the bronchi of the left lung 130 and the right lung 135 is illustrated using white arrows shaded with black dots and outlined in black. The flow of the expiratory gas from the patient 105's airways toward and up the ETT 120 has pulled more DCAs 425 from the infected alveoli 420 and spread the DCAs 425 through more of the patient's airways. The expiratory gas from the infected alveoli 420's exit path can all become contaminated with DCSs 425, including for instance the secondary right bronchus, the main right bronchus, and the distal part of trachea 115 and ETT 120. Additionally, because the dead space 410 is not briskly evacuated, DCAs 425 released from pneumocytes of infected alveoli 420, or otherwise present in the infected alveoli 420, can float into dead space 410, and then from there spread to other proximal portions of lungs 130-135. For example, the flow of the expiratory gas from the patient 105's airways toward and up the ETT 120 has pulled some DCAs 425 into other bronchi of the right lung 135 (e.g., the right primary bronchus 215), adjacent to (or even into) bronchi of the left lung 130 (e.g., the left primary bronchus 210), into the trachea 115, and into the ETT 120. While some of these DCAs 425 will be successfully evacuated from the patient's airways by the ETT 120, in some cases DCAs 425 may remain in the dead space 410 due to lack of timely evacuation of the dead space 410. The DCAs 425 that remain in the dead space 410 can then be spread further by a inspiratory gas provided from the ETT 120 as illustrated in FIG. 4C with an subsequent inspiration after the expiration of FIG. 4B.

FIG. 4C is a conceptual diagram 400C illustrating part of the ventilator system of FIGS. 4A-4B with the endotracheal tube (ETT) 120 providing inspiratory gas that spreads disease-causative agents (DCAs) 425 to more of the diseased right lung 135 and newly introduces DCAs 425 into the newly-diseased left lung 130, for instance as inspiratory gas passes through previously-contaminated airways and ETT 120 (e.g., areas with DCAs 425 in FIG. 4B). This spread causes the right lung 135 of FIG. 4C to include two newly infected alveoli 440, and causes the recovered alveolus 430 of FIG. 4B to become reinfected, becoming a reinfected alveolus 435. The right lung 135 of FIG. 4C also still includes the two infected alveoli 420 of FIGS. 4A-4B.

The ETT 120, as illustrated in FIG. 4C, is providing an inspiratory gas to the patient 105's airways. An exemplary flow of the inspiratory gas down the ETT 120 and into and through the bronchi of the left lung 130 and the right lung 135 is illustrated using white arrows outlined in black. Because some DCAs 425 remain in the dead space 410 after being pulled into the dead space 410 by the flow of the expiratory gas of FIG. 4B, and because the ETT 120 and some airways became contaminated by the expiratory gas as illustrated in FIG. 4B, the inspiratory gas provided from the ETT 120 into the patient 105's airways spreads the DCAs 425 from the dead space 410 and other portions of the patient 105's airways that were contaminated during the expiration of FIG. 4B (e.g., the ETT 120) throughout the patient 105's airways, even to parts of the patient 105's airways that were previously healthy, non-diseased, and/or free of DCAs 425. For example, the flow of the inspiratory gas spreads the DCAs 425 to the recovered alveolus 430 of FIGS. 4A-4B, which newly becomes reinfected to become a reinfected alveolus 435 in FIG. 4C. The reinfected alveolus 435 is illustrated as a black-colored 16-point starburst shape that is shaded with a white crosshatch pattern and outlined in black. The flow of the inspiratory gas spreads the DCAs 425 to other previously-health alveoli 325, newly infecting them, including two newly infected alveoli 440. The newly infected alveoli 440 are illustrated as black-colored 16-point starburst shapes. The first of the newly infected alveoli 440 is located in a part of the right lung 135 far from the infected alveoli 420, branching from a different one of the right secondary bronchi 315 than the infected alveoli 420. The second of the newly infected alveoli 440 is located in the left lung 130. Thus, FIGS. 4A-4C illustrate how a ventilator system that both provides inspiratory gas to the patient 105's airways from the tip 125 of the ETT 120 and evacuates an expiratory gas from the patient 105's airways through the same tip 125 of the ETT 120 can spread DCAs 425 throughout the patient 105's airways, for example from a diseased lung (as in the right lung 135 of FIGS. 4A-4B) to a formerly-healthy lung (as in the left lung 130). This cycle of reinfecting the patient 105's airways, and spreading the DCAs 425 throughout the patient 105's airways, perpetuates and/or spreads diseases and makes it harder for medications, therapeutics, patients' native immune system cells, antibodies, or other treatments to neutralize or eliminate the DCAs 425. This maintains and/or spreads the diseased state in the patient 105's airways.

FIG. 4D is a conceptual diagram 400D illustrating an example of the ventilator systems of FIGS. 4A-4C with an adapter 450 added on one side of the balloon 205 and another adapter 455 added on the other side of the balloon 205. The conceptual diagram 400D of FIG. 4D includes an exploded view of the ventilator system of FIG. 4D, illustrating the ETT 120, the adapter 450, the adapter 455, and a ventilator circuit tube 457. The adapter 450 is coupled to the ETT 120 on one end of the adapter 450, and to a ventilator circuit tube 457 on the other end of the adapter 450. The adapter 455 is coupled to one portion of the ETT 120 (that includes the balloon 205 and goes toward the patient 105's mouth) one end of the adapter 455, and to another portion of the ETT 120 (that includes the tip 125 of the ETT 120 and goes toward the patient 105's lungs 130-135) on the other end of the adapter 455.

The ventilator circuit tube 457 may be, for example, a tube between the ETT 120 and the patient interface 149, at least a part of the patient interface 149, a tube between the patient interface 149 and the second fitting 148, a tube between the second fitting 148 and the first fitting 147, an inspiratory tube 152, an expiratory tube 157, or a combination thereof.

Figure 4F:
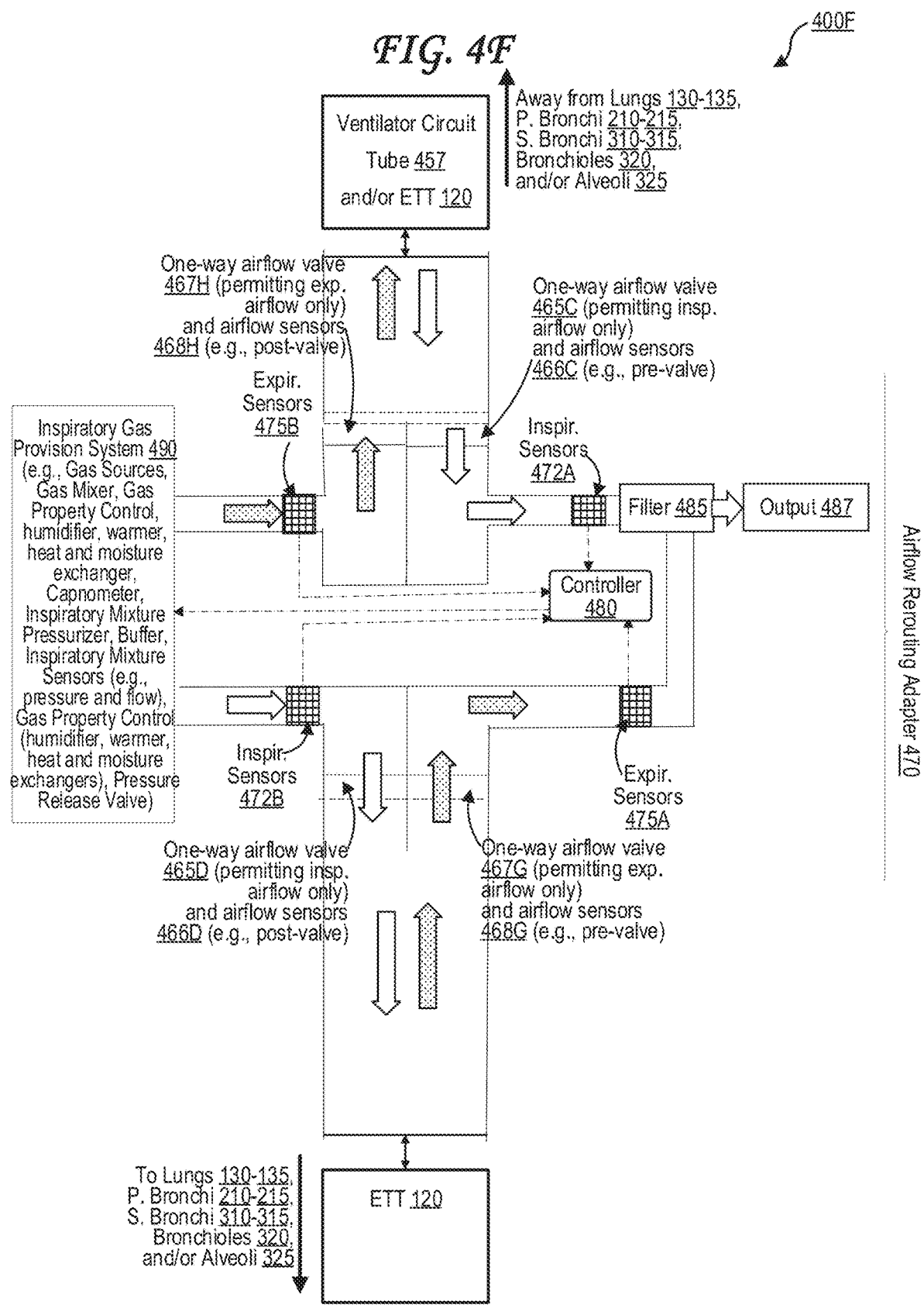
FIG. 4F is a conceptual diagram 400F illustrating a cross-section of an airflow rerouting adapter.

Examples of the adapter 450 include the micro-filter adapter 460 of FIG. 4E, the airflow rerouting adapter 470 of FIG. 4F, and the connector 610 of FIG. 6. Examples of the adapter 455 include the micro-filter adapter 460 of FIG. 4E, the airflow rerouting adapter 470 of FIG. 4F, and the connector 610 of FIG. 6. In some examples, the ventilator system of FIG. 4D may include the adapter 450 but may omit the adapter 455. In some examples, the ventilator system of FIG. 4D may include the adapter 455 but may omit the adapter 450. In some examples, the ventilator system of FIG. 4D may include both the adapter 450 and the adapter 455, which may both be the same type of adapter or may be different types of adapters.

FIG. 4E is a conceptual diagram 400E illustrating a cross-section of a micro-filter adapter 460. The micro-filter adapter 460 includes an inner area 462 and an outer area 464. The inner area 462 and the outer area 464 may be separated by a barrier 463. In some examples, the barrier 463 may be rigid. In some examples, the barrier 463 may be pliable, as in a sleeve and/or a membrane or the barrier maybe the microfiltration medium, on of a kinds later listed. The inner area 462 includes a microfilter medium 465. The microfilter medium 465 may include, for example, N95 filter medium, N99 filter medium, HVAC filter medium, HEPA filter medium, ULPA filter medium, MERV 16 filter medium, MERV 15 filter medium, MERV 14 filter medium, MERV 13 filter medium, MERV 12 filter medium, MERV 11 filter medium, MERV 10 filter medium, MERV 9 filter medium, MERV 8 filter medium, MERV 7 filter medium, MERV 6 filter medium, MERV 5 filter medium, MERV 4 filter medium, paper filter medium, pleated filter medium, non-pleated filter medium, or a combination thereof.

The micro-filter adapter 460 can be an example of the adapter 250 and/or of the adapter 255 of FIG. 4D. Either way, the micro-filter adapter 460 couples to the ETT 120 along a bottom side of the micro-filter adapter 460 in a direction toward the patient 105's left lung 130, right lung 135, left primary bronchus 210, right primary bronchus 215, left secondary bronchi 310, right secondary bronchi 315, other bronchi, bronchioles 320, alveoli 325, or combinations thereof. The micro-filter adapter 460 can couple to the ETT 120 and/or to the ventilator circuit tube 457 along a top side of the micro-filter adapter 460 in a direction away from the patient 105's left lung 130, right lung 135, left primary bronchus 210, right primary bronchus 215, left secondary bronchi 310, right secondary bronchi 315, other bronchi, bronchioles 320, alveoli 325, or combinations thereof.

Examples of inspiratory airflow are illustrated in FIG. 4E using white arrows outlined in black, which enter from the top side of the micro-filter adapter 460 and move toward the bottom side of the micro-filter adapter 460. Examples of expiratory airflow are illustrated in FIG. 4E using white arrows shaded with black dots and outlined in black, which enter from the bottom side of the micro-filter adapter 460 and move toward the top side of the micro-filter adapter 460. While both the inspiratory airflow and expiratory airflow are illustrated flowing at the same time, in some cases inspiratory and expiratory airflow happen sequentially (i.e. inspiratory flow via microfilter medium 465 during inspiration and expiratory flow via outer area bypassing the microfilter medium 465 during expiration). In some cases, inspiratory and expiratory airflow happen simultaneously (i.e. continuous inspiratory flow via microfilter medium 465 and continues expiratory flow via outer area bypassing the microfilter medium). In some cases, inspiratory and expiratory airflow happen independently and intermittently (i.e. intermittent independent inspiratory flow via microfilter medium 465 and intermittent independent intermittent expiratory flow via outer area bypassing the microfilter medium 465 during at any other times). In some cases either inspiratory airflow or expiratory airflow may be flowing through the micro-filter adapter 460 without the other. For instance, at some times, only the inspiratory airflow may be flowing through the micro-filter adapter 460, while at other times, only the expiratory airflow may be flowing through the micro-filter adapter 460. In some examples, the microfilter medium can be placed in outer area 464 as well, as addition to microfilter medium 465 placed in inner area 464, or without the microfilter medium 465 in the inner area.

The micro-filter adapter 460 includes a first one-way airflow valve 465A that permits inspiratory airflow to pass through the first one-way airflow valve 465A into the inner area 462 (based on movement direction moving toward the lungs 130-135) and prevents expiratory airflow from passing through the first one-way airflow valve 465A (based on movement direction moving away from the lungs 130-135). Once in the inner area 462, the inspiratory airflow passes through the microfilter medium 465 and is filtered by the microfilter medium 465. The micro-filter adapter 460 includes a second one-way airflow valve 465B that permits inspiratory airflow to pass through the second one-way airflow valve 465B out from inside the inner area 462 (based on movement direction moving toward the lungs 130-135) and prevents expiratory airflow from passing through the second one-way airflow valve 465B to enter the inner area 462 (based on movement direction moving away from the lungs 130-135). Thus, inspiratory airflow is filtered by the microfilter medium 465 before reaching the lungs 130-135 and bronchi.

The micro-filter adapter 460 can include a one or more one-way airflow valves 467A-467B that permit expiratory airflow to pass through the one or more one-way airflow valves 467A-467B into the outer area 464 (based on movement direction moving away from the lungs 130-135) and prevents inspiratory airflow from passing through the one or more one-way airflow valves 467A-467B (based on movement direction moving toward the lungs 130-135). Once in the outer area 464, the inspiratory airflow moves up without passing through the microfilter medium 465, ensuring the microfilter medium 465 is kept free of DCAs 425 from the patient 105's airways. The micro-filter adapter 460 includes one or more one-way airflow valves 467C-467D that permit expiratory airflow to pass through the one or more one-way airflow valves 467C-467D out from inside the outer area 464 (based on movement direction moving away from the lungs 130-135) and prevents inspiratory airflow from passing through the one or more one-way airflow valves 467C-467D to enter the outer area 464 (based on movement direction moving away from the lungs 130-135). Thus, the inspiratory airflow and the expiratory airflow are kept separate within the micro-filter adapter 460 by the barrier 463 and the various one-way airflow valves.

In some examples, the micro-filter adapter 460 can include, and/or be coupled to, one or more mucus extraction tubes 469A-469B, which may extract mucus from expiratory airflow and/or inspiratory airflow to help prevent mucus from clogging any of the one-way airflow valves 465A-465B, from clogging any of the one-way airflow valves 467A-467F, from clogging the microfilter medium 465, from clogging the inner area 462, from clogging the outer area 464, from weakening the barrier 463, or a combination thereof. The one or more mucus extraction tubes 469A-469B may use suction (e.g., negative pressure) to extract the mucus from the airflow. In some examples, the micro-filter adapter 460 can include one or more one-way airflow valves 467E-467F that permit expiratory airflow to pass through the one or more one-way airflow valves 467E-467F into the one or more mucus extraction tubes 469A-469B (based on movement direction moving away from the lungs 130-135) and prevents inspiratory airflow from passing through the one or more one-way airflow valves 467E-467F to enter the one or more mucus extraction tubes 469A-469B (based on movement direction moving toward the lungs 130-135). In some examples, the one or more one-way airflow valves 467E-467F instead permit inspiratory airflow to pass through the one or more one-way airflow valves 467E-467F into the one or more mucus extraction tubes 469A-469B (based on movement direction moving toward the lungs 130-135) and prevents expiratory airflow from passing through the one or more one-way airflow valves 467E-467F to enter the one or more mucus extraction tubes 469A-469B (based on movement direction moving away from the lungs 130-135). In some examples, the one or more one-way airflow valves 467E-467F permit both inspiratory airflow and expiratory airflow to pass through the one or more one-way airflow valves 467E-467F into the one or more mucus extraction tubes 469A-469B. A first mucus extraction tube 469A is illustrated above (away from the lungs 130-135) the microfilter medium 465 and above one-way airflow valves 465A, 467C, and 467D. A second mucus extraction tube 469B is illustrated below (toward from the lungs 130-135) the microfilter medium 465 and below one-way airflow valves 465B, 467A, and 467B. The mucus extraction tube(s) 469A-469B can connect to the outer area 464, the inner area 462, or both. In some examples, the barrier 463 may be cylindrical in shape as illustrated in FIG. 4E, In some examples, the barrier 463 may be conical in shape, which may increase filtration surface area, reducing the pressure gradient across the microfilter medium 465 and maximizing the lifetime of microfilter medium 465. In some examples, a microfilter adapter 460 (and/or a microfilter medium 465 on its own) can be placed distally from trachea 115, within inspiratory lumens 220-225 and/or expiratory lumens 520/525. In some examples, a microfilter adapter 460 may be used upside-down, or backwards, relative to the airflow and directionality illustrated in FIG. 4E, so that the expiratory airflow is filtered through the microfilter medium 465 rather than the inspiratory airflow. In some examples, the outer area 464 may also include a separate microfilter medium (of any of the types discussed with respect to the microfilter medium 465) that may filter the airflow passing through the outer area 464 of the microfilter adapter 460.

A micro-filter adapter 460 may provide technical improvements over the ventilator systems of FIGS. 4A-4C by filtering inspiratory airflow before the inspiratory airflow reaches the patient 105's lungs 130-135. A micro-filter adapter 460 may provide technical improvements over the ventilator systems of FIGS. 4A-4C by separating the inspiratory airflows and expiratory airflows to prevent DCAs 425 from the expiratory airflows from mixing into the inspiratory airflows and spreading throughout the patient 105's lungs 130-135 and airways in general.

FIG. 4F is a conceptual diagram 400F illustrating a cross-section of an airflow rerouting adapter 470. The airflow rerouting adapter 470 can be an example of the adapter 450 and/or of the adapter 455 of FIG. 4D. Either way, the airflow rerouting adapter 470 couples to the ETT 120 along a bottom side of the airflow rerouting adapter 470 in a direction toward the patient 105's left lung 130, right lung 135, left primary bronchus 210, right primary bronchus 215, left secondary bronchi 310, right secondary bronchi 315, other bronchi, bronchioles 320, alveoli 325, or combinations thereof. The airflow rerouting adapter 470 can couple to the ETT 120 and/or to the ventilator circuit tube 457 along a top side of the airflow rerouting adapter 470 in a direction away from the patient 105's left lung 130, right lung 135, left primary bronchus 210, right primary bronchus 215, left secondary bronchi 310, right secondary bronchi 315, other bronchi, bronchioles 320, alveoli 325, or combinations thereof.

Examples of inspiratory airflow are illustrated in FIG. 4F using white arrows outlined in black. A primary inspiratory airflow enters the airflow rerouting adapter 470 from the top side of the airflow rerouting adapter 470 and moves toward the filter 485 and the output 487. A secondary inspiratory airflow enters the airflow rerouting adapter 470 from the inspiratory gas provision system 490 of the airflow rerouting adapter 470 moves toward the bottom of the airflow rerouting adapter 470, toward the patient 105's lungs 130-135.

Examples of expiratory airflow are illustrated in FIG. 4E using white arrows shaded with black dots and outlined in black. A primary expiratory airflow enters the airflow rerouting adapter 470 from the bottom side of the airflow rerouting adapter 470 (from the patient 105's lungs 130-135) and moves toward the filter 485 and the output 487. A secondary expiratory airflow enters the airflow rerouting adapter 470 from the inspiratory gas provision system 490 of the airflow rerouting adapter 470 moves toward the top of the airflow rerouting adapter 470, away from the patient 105's lungs 130-135. While both the inspiratory airflow and expiratory airflow are illustrated flowing at the same time, in some cases either inspiratory airflow or expiratory airflow may be flowing through the airflow rerouting adapter 470 without the other, and/or sequentially, or continuously, For instance, at some times, only the inspiratory airflow may be flowing through the airflow rerouting adapter 470, while at other times, only the expiratory airflow may be flowing through the airflow rerouting adapter 470.

A set of one-way airflow valves 465C-465D can route the inspiratory airflow along the previously-described and illustrated paths. A set of one-way airflow valves 467G-467H can route the expiratory airflow along the previously-described and illustrated paths.

The airflow rerouting adapter 470 includes a one-way airflow valve 465C that permits the primary inspiratory airflow to pass through the one-way airflow valve 465C toward the inspiratory sensors 472A, the filter 485, and the output 487 (based on movement direction moving toward the lungs 130-135) and prevents expiratory airflow from passing through the one-way airflow valve 465C (based on movement direction moving away from the lungs 130-135). The airflow rerouting adapter 470 includes a one-way airflow valve 465D that permits the secondary inspiratory airflow to pass through the one-way airflow valve 465D toward the inspiratory sensors 472B, and into the ETT 120 toward the tip 125 of the ETT 120 and toward the patient 105's lungs 130-135 (based on movement direction moving toward the lungs 130-135) and prevents expiratory airflow from passing through the one-way airflow valve 465D (based on movement direction moving away from the lungs 130-135).

The airflow rerouting adapter 470 includes a one-way airflow valve 467G that permits the primary expiratory airflow to pass through the one-way airflow valve 467G toward the expiratory sensors 475A, the filter 485, and the output 487 (based on movement direction moving away from the lungs 130-135) and prevents inspiratory airflow from passing through the one-way airflow valve 467G (based on movement direction moving toward the lungs 130-135). The airflow rerouting adapter 470 includes a one-way airflow valve 467H that permits the secondary expiratory airflow to pass through the one-way airflow valve 467H toward the expiratory sensors 475B, toward the top of the airflow rerouting adapter 470 and into the ventilator circuit tube 457 and/or ETT 120 (based on movement direction moving away from the lungs 130-135) and prevents inspiratory airflow from passing through the one-way airflow valve 467H (based on movement direction moving toward the lungs 130-135).

The output 487 can be, for example, a sink or an exhaust. Examples of the output 487 include the expiratory gas output(s) 165 and the output 958. Examples of the filter 485 include the filtration 956. In some examples, the primary inspiratory airflow may be output to the filter 485 and/or to the output 487. The airflow rerouting adapter 470 can effectively replace the primary inspiratory airflow with the secondary inspiratory airflow provided by the inspiratory gas provision system 490, which can provide the patient 105's lungs 130-135 and airways generally with more fine-tuned inspiratory airflow than the ventilator system into which the airflow rerouting adapter 470 is being added. This fine-tuned inspiratory airflow can be clean of DCAs 425, as it is not coming from an already-contaminated ETT 120, ventilator circuit tubing 457, other tubing, or other portion(s) of the ventilator system. In some examples, the primary expiratory airflow may be output to the filter 485 and/or to the output 487. The airflow rerouting adapter 470 can effectively replace the primary expiratory airflow with the secondary expiratory airflow provided by the expiratory gas provision system 490, which can provide the ETT 120 and/or ventilator circuit tube 457 with expiratory airflow that prevents warnings or alarms (e.g., regarding lack of expiratory airflow or irregular expiratory airflow) from being raised by the ventilator system into which the airflow rerouting adapter 470 is being added.

In some examples, the airflow rerouting adapter 470 includes one or more airflow sensors 466C beside the one-way airflow valve 465C that detect attributes of the primary inspiratory airflow. In some examples, the one or more airflow sensors 466C are above the one-way airflow valve 465C, and therefore the primary inspiratory airflow encounters the one or more airflow sensors 466C before passing through the one-way airflow valve 465C. In some examples, the airflow rerouting adapter 470 includes one or more airflow sensors 466D beside the one-way airflow valve 465D that detect attributes of the secondary inspiratory airflow. In some examples, the one or more airflow sensors 466D are below the one-way airflow valve 465D, and therefore the secondary inspiratory airflow encounters the one or more airflow sensors 466D after passing through the one-way airflow valve 465D. In some examples, the airflow rerouting adapter 470 includes one or more airflow sensors 468G beside the one-way airflow valve 467G that detect attributes of the primary expiratory airflow. In some examples, the one or more airflow sensors 468G are below the one-way airflow valve 467G, and therefore the primary expiratory airflow encounters the one or more airflow sensors 468G before passing through the one-way airflow valve 467G. In some examples, the airflow rerouting adapter 470 includes one or more airflow sensors 468H beside the one-way airflow valve 467H that detect attributes of the secondary expiratory airflow. In some examples, the one or more airflow sensors 468H are above the one-way airflow valve 467H, and therefore the secondary expiratory airflow encounters the one or more airflow sensors 468H after passing through the one-way airflow valve 467H.

The various sensors of the airflow rerouting adapter 470—including the one or more airflow sensors 466C, the one or more airflow sensors 466D, the one or more airflow sensors 468G, the one or more airflow sensors 468H, the—can each measure one or more airflow attributes of airflow. Each of these sensors can include, for example, pressure sensors, pressure transducers, flow sensors, capnometers, humidity sensors, oximeters (oxygen sensors), thermometers (temperature sensors), other types of sensors discussed herein, or a combination thereof. The one or more airflow attributes can include, for example, airflow, pressure, speed, velocity, volume, temperature, moisture, humidity, $O_2$ concentration, $CO_2$ concentration, N concentration, Ar concentration, $H2O$ concentration, other sensor measurement data discussed herein, or a combination thereof. For instance, examples of any of the sensors of the airflow rerouting adapter 470 can include the capnometer 926, the inspiratory mixture sensors 910, the inspiratory mixture sensors 920, the intratracheal sensors 934, the capnometer 938, the capnometer 948, the expiratory mixture sensors 940, the expiratory mixture sensors 950, or a combination thereof. Sensor data from the sensors of the airflow rerouting adapter 470 can be passed to a controller 480. The controller 480 can control airflow provision (e.g., of the secondary inspiratory airflow and/or of the secondary expiratory airflow) by the inspiratory gas provision system 490. The controller 480 can be an example of a controller 170.

In some examples, the inspiratory gas provision system 490 can include gas sources, gas mixer, gas property control, humidifier, warmer, heat and moisture exchanger, capnometer, inspiratory mixture pressurizer, buffer, inspiratory mixture sensors (e.g., pressure and flow), gas property control (humidifier, warmer, heat and moisture exchangers), pressure relieve valve. In some examples, the inspiratory gas provision system 490 can include, for example, the inspiratory flow control system(s) 150, the inspiratory gas source(s) 160, the gas sources 932, the gas mixer(s) 930, the gas property control(s) 928, the capnometer(s) 926, the inspiratory mixture pressurizer 914, the buffer 912, the inspiratory mixture sensors 910, the gas property control 908, the pressure release valve 906, the inspiratory mixture pressurizer 924, the buffer 922, the inspiratory mixture sensors 920, the gas property control 918, the pressure release valve 916, or a combination thereof.

In some examples, the controller 480 may mix, pressurize, heat, cool, humidify, dehumidify, or otherwise set one or more attributes of the secondary inspiratory airflow based on one or more one or more attributes of the primary inspiratory airflow as measured by the airflow sensor(s) 466C and/or the inspiratory sensors 472A. The controller 480 may verify that the attributes match using the inspiratory sensors 472B and/or the airflow sensors 466D. In some examples, the controller 480 may mix, pressurize, heat, cool, humidify, dehumidify, or otherwise set one or more attributes of the secondary expiratory airflow based on one or more one or more attributes of the primary expiratory airflow as measured by the airflow sensor(s) 468G and/or the expiratory sensors 475A. The controller 480 may verify that the attributes match using the expiratory sensors 475B and/or the airflow sensors 468H.

An airflow rerouting adapter 470 may provide technical improvements over the ventilator systems of FIGS. 4A-4C by allowing to provide uncontaminated with DCAs inspiratory gas via uncontaminated with DCAs inspiratory lumens, and customized control of inspiratory airflow and/or expiratory airflow using the inspiratory gas provision system 490, while still using the framework of a ventilator system such as those of FIGS. 4A-4C, and simulating expected inspiratory airflow and/or expiratory airflow to the ventilator system using the inspiratory gas provision system 490. In some examples, use of an airflow rerouting adapter 470 can provide some technical improvements similar to a ventilator system illustrated in FIGS. 5A-5D.

FIG. 5A is a conceptual diagram 500A illustrating part of a ventilator system with an endotracheal tube (ETT) 120 that includes an expiratory lumen 510 that evacuates expiratory gas, a left inspiratory lumen 220 that provides inspiratory gas to the left primary bronchus 210 and left lung 130, and a right inspiratory lumen 225 that provides inspiratory gas to the right primary bronchus 215 and right lung 135. The left inspiratory lumen 220 and right inspiratory lumen 225 both extend beyond the tip 125 of the ETT 120 toward and/or into the patient 105's airways. The left inspiratory lumen 220 and right inspiratory lumen 225 both extend further into the patient 105's airways than the tip 125 of the ETT 120 does. In particular, the left inspiratory lumen 220 extends beyond the tip 125 of the ETT 120 toward the patient 105's left primary bronchus 210, left lung 130, and/or other left bronchi within the left lung 130. The right inspiratory lumen 225 extends beyond the tip 125 of the ETT 120 toward the patient 105's right primary bronchus 215, right lung 135, and/or other right bronchi within the right lung 135.

The left inspiratory lumen 220 and right inspiratory lumen 225 each provide a gaseous volume of inspiratory gas(es) to different portions of the patient 105's airways. The left inspiratory lumen 220 provides a first (left) gaseous volume of inspiratory gas(es) to patient 105's left primary bronchus 210, left lung 130, other left bronchi within the left lung 130, bronchioles 320 within the left lung 130, alveoli 325 within the left lung 130, or a combination thereof. An exemplary flow of the first (left) gaseous volume of inspiratory gas(es) down the left inspiratory lumen 220 and into the patient 105's airways is illustrated using white arrows outlined in black. The right inspiratory lumen 225 provides a second (right) gaseous volume of inspiratory gas(es) to patient 105's right primary bronchus 215, right lung 135, other right bronchi within the right lung 135, bronchioles 325 within the right lung 135, alveoli 325 within the right lung 135, or a combination thereof. An exemplary flow of the second (right) gaseous volume of inspiratory gas(es) down the right inspiratory lumen 225 and into the patient 105's airways is illustrated using white arrows outlined in black.

The ETT 120 of FIG. 5A houses an expiratory lumen 510. For instance, as illustrated in FIG. 6 and FIG. 7A, any space in the ETT 120 not taken up by the left inspiratory lumen 220 or the right inspiratory lumen 225 can be used as an expiratory lumen 510. Thus, the tip 125 of the ETT 120 is also the tip of the expiratory lumen 510. Thus, in FIG. 5A, the left inspiratory lumen 220 and right inspiratory lumen 225 both extend beyond the tip of the expiratory lumen 510 toward the patient 105's airways. The left inspiratory lumen 220 and right inspiratory lumen 225 both extend further into the patient 105's airways than the tip of the expiratory lumen 510 does. The expiratory lumen 510, as illustrated in FIG. 4B, is receiving and/or evacuating expiratory gas(es) from the patient 105's airways. An exemplary flow of the expiratory gas(es) up the expiratory lumen 510 and from the trachea 115 and bronchi of the left lung 130 and the right lung 135 is illustrated using white arrows shaded with black dots and outlined in black.

Figure 5C:
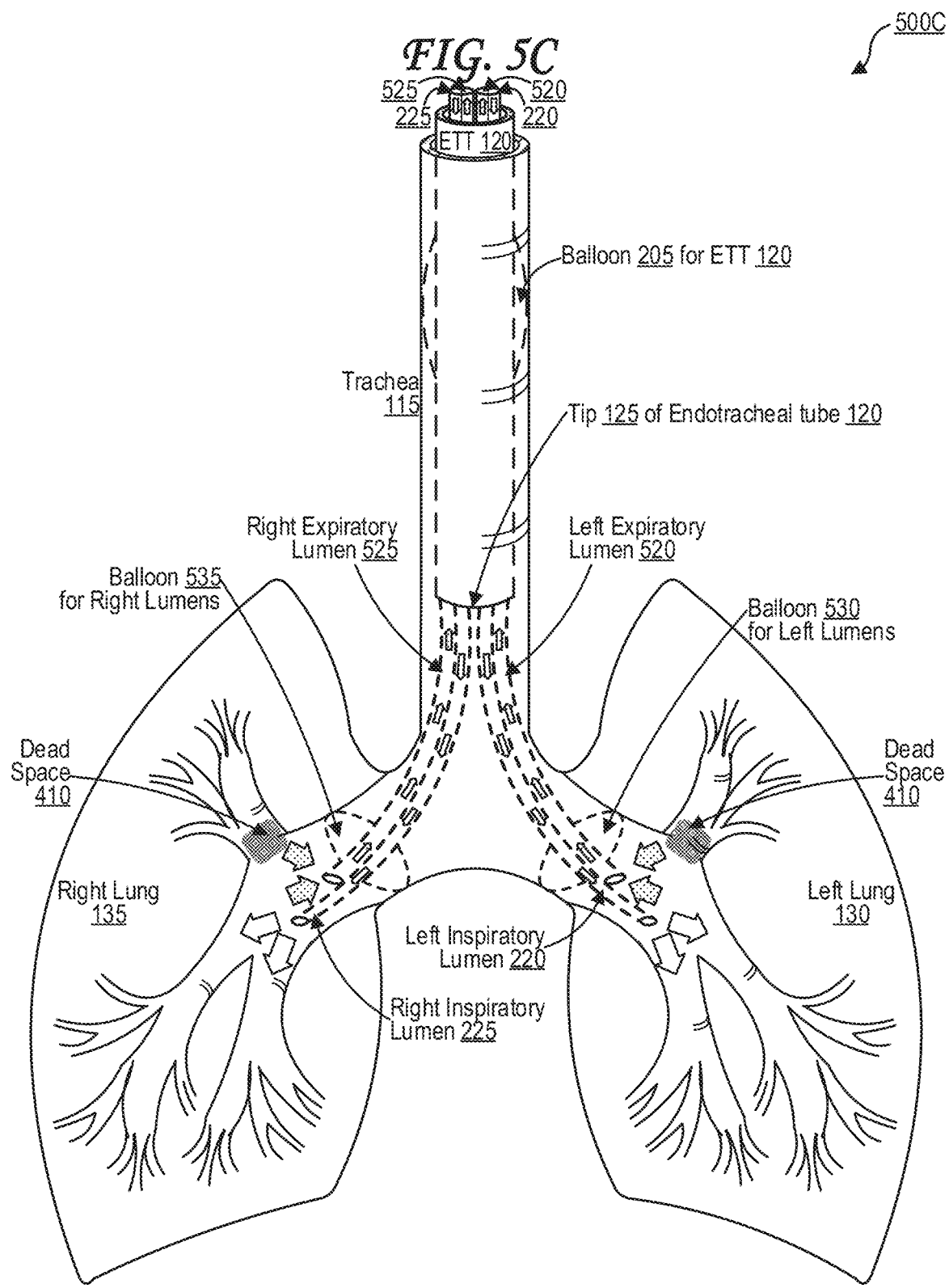
FIG. 5C is a conceptual diagram illustrating part of a ventilator system with an endotracheal tube (ETT) that includes a left expiratory lumen that evacuates expiratory gas from a left primary bronchus and left lung, a right expiratory lumen that evacuates expiratory gas from a right primary bronchus and right lung, a left inspiratory lumen that provides inspiratory gas to the left primary bronchus and left lung, and a right inspiratory lumen that provides inspiratory gas to the right primary bronchus and right lung.

The ventilator systems of FIGS. 5A-5C reduce dead space 410 compared to the ventilator systems of FIGS. 4A-4C by having inspiratory gas delivered more directly and proximally to the alveoli, and in most embodiment and most of ventilatory modes (as illustrated on FIGS. 8A-8E) by continuous or all almost continuous clearing of the dead space with continues gas flow between the inspiratory lumen or lumens and expiratory lumen or lumens. The dead space 410 in FIGS. 5A-5C is identified by shaded regions similar to those that indicate dead space 410 in FIGS. 4A-4C. The reduction in dead space 410 and continuous or close to continues clearance of dead space 410 can reduce the ventilator's ability to spread DCAs 425 from diseased portions of a patient 105's airways to healthy portions of the patient 105's airways, as illustrated in FIG. 5B. Additionally, inspiratory gas can be consistently and/or continuously delivered to the lungs 130-135 by clean (non-contaminated) inspiratory lumens 250/255, as all contaminated expiratory gas leaves the lungs via separate expiratory lumen(s) 510/520/525.

FIG. 5B is a conceptual diagram 500B illustrating part of the ventilator system of FIG. 5A where the right lung 135 is diseased and the left lung 130 is healthy. Like FIG. 4A, the right lung 135 of FIG. 5B includes two infected alveoli 420 and a recovered alveolus 430. Several DCAs 425 are illustrated near the two infected alveoli 420 in the diseased right lung 135. However, the ventilator system(s) of FIGS. 5A-5C does not spread the DCAs 425 to different parts of the patient 105's airways as readily as the ventilator system(s) of FIGS. 4A-4C. For instance, the ventilator system(s) FIGS. 5A-5C include physical separation between the tip of the expiratory lumen 510 (the tip 125 of the ETT 120) and tips of the inspiratory lumens (the left inspiratory lumen 220 and the right inspiratory lumen 225), preventing dead space cross between the left lung 130 (and/or the left primary bronchus 210) and the right lung 135 (and/or the right primary bronchus 215) through which DCAs 425 could otherwise cross between left lungs/bronchi and right lungs/bronchi. The ventilator system(s) FIGS. 5A-5C include physical separation between the tip of the left inspiratory lumen 220 and the tip of the right inspiratory lumen 225, also preventing dead space between the left lung 130 (and/or the left primary bronchus 210) and the right lung 135 (and/or the right primary bronchus 215) through which DCAs 425 could otherwise cross between lungs/bronchi.

FIG. 5C is a conceptual diagram 500C illustrating part of a ventilator system with an endotracheal tube (ETT) 120 that includes a left expiratory lumen 520 that evacuates expiratory gas from a left primary bronchus 210 and left lung 130, a right expiratory lumen 525 that evacuates expiratory gas from a right primary bronchus 215 and right lung 135, a left inspiratory lumen 220 that provides inspiratory gas to the left primary bronchus 210 and left lung 130, and a right inspiratory lumen 225 that provides inspiratory gas to the right primary bronchus 215 and right lung 135. The ventilator system of FIG. 5C is similar to the ventilator system of FIGS. 5A and 5B, for instance because the ventilator system of FIG. 5C also includes the left inspiratory lumen 220 and the right inspiratory lumen 225. The left inspiratory lumen 220 and the right inspiratory lumen 225 of the ventilator system of FIG. 5C function similarly to the left inspiratory lumen 220 and the right inspiratory lumen 225 of the ventilator system of FIGS. 5A and 5B.

However, the ventilator system of FIG. 5C includes the left expiratory lumen 520 and the right expiratory lumen 525 in place of a single expiratory lumen 510 of the ventilator system of FIGS. 5A and 5B. The left expiratory lumen 520 and right expiratory lumen 525 both extend beyond the tip 125 of the ETT 120 toward and/or into the patient 105's airways. The left expiratory lumen 520 and right expiratory lumen 525 both extend further into the patient 105's airways than the tip 125 of the ETT 120 does. In particular, the left expiratory lumen 520 extends beyond the tip 125 of the ETT 120 toward the patient 105's left primary bronchus 210, left lung 130, and/or other left bronchi within the left lung 130. The right expiratory lumen 525 extends beyond the tip 125 of the ETT 120 toward the patient 105's right primary bronchus 215, right lung 135, and/or other right bronchi within the right lung 135.

In some examples (as illustrated in FIG. 4C), the left inspiratory lumen 220 extends beyond the tip of the left expiratory lumen 520 toward and/or into the patient 105's airways. In some examples (as illustrated in FIG. 4C), the left inspiratory lumen 220 extends further into the patient 105's airways than the tip of the left expiratory lumen 520. In some examples (as illustrated in FIG. 4C), the right inspiratory lumen 225 extends beyond the tip of the right expiratory lumen 525 toward and/or into the patient 105's airways. In some examples (as illustrated in FIG. 4C), the right inspiratory lumen 225 extends further into the patient 105's airways than the tip of the right expiratory lumen 525.

In some examples (not illustrated), the left expiratory lumen 520 extends beyond the tip of the left inspiratory lumen 220 toward and/or into the patient 105's airways. In some examples (not illustrated), the left expiratory lumen 520 extends further into the patient 105's airways than the tip of the left inspiratory lumen 220. In some examples (not illustrated), the right expiratory lumen 225 extends beyond the tip of the right inspiratory lumen 525 toward and/or into the patient 105's airways. In some examples (not illustrated), the right expiratory lumen 225 extends further into the patient 105's airways than the tip of the right inspiratory lumen 525.

The left expiratory lumen 520 and the right expiratory lumen 525, as illustrated in FIG. 5C, are both receiving and/or evacuating expiratory gas(es) from different parts of the patient 105's airways. An exemplary flow of the expiratory gas(es) up the left expiratory lumen 520 from the bronchi of the left lung 130 is illustrated using white arrows shaded with black dots and outlined in black. An exemplary flow of the expiratory gas(es) up the right expiratory lumen 525 from the bronchi of the right lung 135 is illustrated using white arrows shaded with black dots and outlined in black.

In some examples, the left inspiratory lumen 220 and the left expiratory lumen 520 are coupled together. In some examples, the right inspiratory lumen 225 and the right expiratory lumen 525 are coupled together. In some examples, the left inspiratory lumen 220 and the left expiratory lumen 520 are two distinct parts of a single lumen, for example with a membrane in between (as in FIG. 7B). In some examples, the right inspiratory lumen 225 and the right expiratory lumen 525 are two distinct parts of a single lumen, for example with a membrane in between (as in FIG. 7B).

In some examples, a balloon 530 for the left lumens (the left inspiratory lumen 220 and the left expiratory lumen 520) may, in its inflated state (as illustrated in FIG. 5C), secure the left lumens in position in the trachea 115 and/or left primary bronchus 210, protect the trachea 115 and/or left primary bronchus 210 from being damaged by the left lumens, and/or prevent airflows from passing through the trachea 115 and/or left primary bronchus 210 other than through the left lumens. In some examples, a balloon 535 for the right lumens (the right inspiratory lumen 225 and the right expiratory lumen 525) may, in its inflated state (as illustrated in FIG. 5C), secure the right lumens in position in the trachea 115 and/or right primary bronchus 215, protect the trachea 115 and/or right primary bronchus 215 from being damaged by the right lumens, and/or prevent airflows from passing through the trachea 115 and/or right primary bronchus 215 other than through the right lumens. In some examples, the balloon 530 and/or the balloon 535 may be missing and/or may be intentionally left uninflated, for example to prevent unintentionally producing one or more ulcers, because the balloon 205 may be safer, an/or because the balloon 205 may provide sufficient isolation of airflow on its own in some circumstances. In some examples, a controller 170 of a pneumatic system 140 can adjust pressures to help prevent airflow from crossing between the left lung 130 and the right lung even without presence or inflation of the balloon 530 and/or the balloon 535. In some examples, the balloon 205 may be missing and/or may be intentionally left uninflated, because the balloon 530 and/or the balloon 535 may provide sufficient isolation of airflow without the balloon 205.

In some examples, the left expiratory lumen 520, the right expiratory lumen 525, the left inspiratory lumen 220, and/or the right inspiratory lumen 225 can include one or more valves for uni-directional gas flow. Valves for uni-directional gas flow can prevent expiratory gas from getting into the left inspiratory lumen 220 and/or the right inspiratory lumen 225. Valves for uni-directional gas flow can prevent inspiratory gas from getting into the left expiratory lumen 520 and/or the right expiratory lumen 525. This can be particularly useful when an adapter such as the connector 610 of FIG. 6 is used. Such valves can improve isolation of inspiratory and expiratory lumens.

In some examples, the left expiratory lumen 520 and the right expiratory lumen 525 can reach positions at or adjacent to the carina of the left primary bronchus 310 and the carina of the right primary bronchus 315, respectively. In some examples, the left inspiratory lumen 220 and the right inspiratory lumen 225 can reach positions past (and/or further deeper into the bronchial tree than) the carina of the left primary bronchus 310 and the carina of the right primary bronchus 315, respectively.

In some examples, the left expiratory lumen 520, the right expiratory lumen 525, the left inspiratory lumen 220, and/or the right inspiratory lumen 225 can extend deeper into a patient 105's bronchial tree, which may further reduce dead space. For instance, the left expiratory lumen 520, the right expiratory lumen 525, the left inspiratory lumen 220, and/or the right inspiratory lumen 225 can extend into secondary bronchi, tertiary bronchi, $4^{th}$ order bronchi, $5^{th}$ order bronchi, $6^{th}$ order bronchi, and so forth, or some combination thereof. The tips of the left inspiratory lumen 220 and/or left expiratory lumen 520 can extend into the superior lobe and/or the inferior lobe of the left lung 130. The tips of the right inspiratory lumen 225 and/or the right expiratory lumen 525 can extend into the superior lobe, the middle lobe, or the inferior lobe of the right lung 135. In an illustrative example, the tips of the left expiratory lumen 520 and the right expiratory lumen 525 extend into the superior lobes of the left lung 130 and the right lung 135, while the tips of the left inspiratory lumen 220 and the right inspiratory lumen 225 extend into inferior lobes of the left lung 130 and the right lung 135. The arrangement in this illustrative example can reduce dead space 410 by a particularly significant amount. In some examples, the left expiratory lumen 520, the right expiratory lumen 525, the left inspiratory lumen 220, and/or the right inspiratory lumen 225 can themselves branch off into further sub-lumens, for example with different sub-lumens going into different bronchi (e.g., different secondary bronchi, tertiary bronchi, $4^{th}$ order bronchi, $5^{th}$ order bronchi, $6^{th}$ order bronchi, and so forth).

In some examples, different lumens (e.g., the left expiratory lumen 520, the right expiratory lumen 525, the left inspiratory lumen 220, and/or the right inspiratory lumen 225) can include markers (e.g., at the tips of the lumens and/or along the lengths of the lumens) that allow the lumens to be located using a scan of the patient 105 and/or using triangulation. The markers can include materials that are visible in scans of the patient 105, such as radiopaque markers, radiolucent markers, radioactive tracers. Scans may include X-ray scans, magnetic resonance imagery (MRI) scans, computerized tomography (CT) scans, computed axial tomography (CAT) scans, C-arm scans, positron emission tomography (PET) scans, fluoroscopy scans, angiography scans, or combinations thereof. In some examples, the markers may include solenoids, magnetic field emitters, electromagnetic field emitters, wireless signal transmitters, or a combination thereof. Such markers may be located within the patient 105 by detecting the fields or signals transmitted by the markers and detecting distance between the receiver(s) and the marker transmitting the signals based on signal travel time, signal frequency shift, and/or another change in a signal property between transmission of the signal and receipt of the signal. Such markers may be located within the patient 105 using triangulation, by detecting the fields or signals transmitted by the markers using multiple receivers or using a single receiver at multiple points in time.

FIG. 5D is a conceptual diagram 500D illustrating part of a ventilator system with an endotracheal tube (ETT) 120 that includes an inspiratory lumen 540 that provides inspiratory gas, a left expiratory lumen 520 that evacuates expiratory gas from the left primary bronchus and left lung 130, and a right expiratory lumen 525 that evacuates expiratory gas from the right primary bronchus and right lung 135.

As noted previously, it may be useful in the ventilator systems of FIGS. 5A-5D to include carbon dioxide ($CO_2$) in the inspiratory gas mixture. For instance, depending on how inspiratory flows are set (see e.g., inspiratory flows 830A-830E) and/or how expiratory flows are set (see e.g., inspiratory flows 835A-835E), carbon dioxide ($CO_2$) may be being evacuated excessively and/or from the patient 105's airways. Lack or decreased concentration of carbon dioxide ($CO_2$) can increase alkalinity, pushing pH too high, and can cause negative effects such as alkalosis. Including carbon dioxide ($CO_2$) in the inspiratory gas mixture can offset the evacuation of carbon dioxide ($CO_2$), reducing alkalinity, lowering pH, and preventing negative effects such as alkalosis.

In some examples, the ventilator systems of FIGS. 5A-5D may be modified to include only inspiratory lumen into only one lung and/or only one expiratory lumen into only one lung. For instance, the ventilator systems of FIGS. 5A-5D may be modified to include only the left inspiratory lumen 220 without the right inspiratory lumen 225, or to include only the right inspiratory lumen 225 without the left inspiratory lumen 220. Similarly, the ventilator systems of FIGS. 5A-5D may be modified to include only the left expiratory lumen 520 without the right expiratory lumen 525, or to include only the right expiratory lumen 525 without the left expiratory lumen 520. Even in situations with only one inspiratory lumen 220/225 into only one lung 130/135 and/or only one expiratory lumen 520/525 into only one lung 130/135, dead space 410 is still decreased relative to dead space 410 in ventilator systems of FIGS. 4A-4C, due to deeper division of inspiratory and expiratory airflow. In some examples, this type of modification may be desirable, for example to assist a patient that only has one functional lung and/or to make a low-cost ventilator system (e.g., to assist patients in developing countries).

FIG. 6 is a conceptual diagram 600 illustrating part of a ventilator system with an endotracheal tube (ETT) 120 that includes an expiratory lumen 510 that evacuates expiratory gas, a left inspiratory lumen 220 that provides inspiratory gas, and a right inspiratory lumen 225 that provides inspiratory gas. The ventilator system of FIG. 6 is similar to the ventilator system of FIGS. 5A and 5B in that the ventilator system of FIG. 6 includes an ETT 120 with a left inspiratory lumen 220, a right inspiratory lumen 225, an expiratory lumen 510, a tip 125, and a balloon 205. The left inspiratory lumen 220 and the right inspiratory lumen 225 pass through at least part of the ETT 120. The expiratory lumen 510 can include at least a part of the ETT 120. A connector 610 can mechanically and/or pneumatically connect the left inspiratory lumen 220 and the right inspiratory lumen 225 to the ETT 120. In some examples, the connector 610 can mechanically and/or pneumatically introduce the left inspiratory lumen 220 and the right inspiratory lumen 225 into the ETT 120. The connector 610 can also mechanically and/or pneumatically couple the ETT 120 to the ventilator tubing 605.

The ETT 120, the expiratory lumen 510, the left inspiratory lumen 220, and/or the right inspiratory lumen 225, can each extend downward in FIG. 6 toward the left lung 130, right lung 135, left primary bronchus 210, right primary bronchus 215, left secondary bronchi 310, right secondary bronchi 315, other bronchi, bronchioles 320, alveoli 325, or combinations thereof. The left inspiratory lumen 220, and/or the right inspiratory lumen 225 can come from the left side of FIG. 6, from inspiratory tube(s) 152, the inspiratory flow control system(s) 150, inspiratory gas source(s) 160, or a combination thereof. In some examples, the left inspiratory lumen 220 couples to its own inspiratory tube 152, inspiratory flow control system 150, and/or inspiratory gas source(s) 160. In some examples, the right inspiratory lumen 225 couples to its own inspiratory tube 152, inspiratory flow control system 150, and/or inspiratory gas source(s) 160. The ventilator tubing 605 can couple to the expiratory tube(s) 157, the expiratory flow control system(s) 155, the expiratory gas output(s) 165, or a combination thereof. In another illustrative example the ventilator tubing 605 can couple to the patient interface 149, $1^{st}$ fitting 147 or $2^{nd}$ fitting 148, inspiratory tube(s) 152 and expiratory tube(s) 157, the expiratory flow control system(s) 155, the expiratory gas output(s) 165, or a combination thereof. In the latter example, it would be the appropriate combination of pressures (high-pressure flow in inspiratory lumens left 220 and right 225) that would direct the inspiratory gas from inspiratory lumens 220 and 225 into the expiratory tube(s) 157, the expiratory flow control system(s) 155, the expiratory gas output(s) 165. Same high-pressure flow in the inspiratory lumens 220 and 225 would limit or stop the inflow of inspiratory gas via inspiratory tube(s) 152.

Exemplary flows of the inspiratory gas(s) into, along, and out of each of the left inspiratory lumen 220 and the right inspiratory lumen 225 are illustrated using white arrows that are outlined in black. Exemplary flows of the expiratory gas(s) up the expiratory lumen 510 of the ETT 120, up the ventilator tubing 605, and out of the ventilator tubing are illustrated using white arrows shaded with black dots and outlined in black. In some examples, the connector 510 may also provide a left expiratory lumen 520 and a right expiratory lumen 525 as in FIGS. 5C and 5D. In some examples, the connector 610 may be used as an adapter 450 and/or as an adapter 455. In some examples, use of the connector 610 as an adapter 450 and/or as an adapter 455 can provide a left inspiratory lumen 220, a right inspiratory lumen 225, a left expiratory lumen 520, and/or a right expiratory lumen 525 to a ventilator system that might not otherwise include such lumens, such as the ventilator system(s) of FIGS. 4A-4D. In some examples, use of the connector 610 as an adapter 450 and/or as an adapter 455 can provide inspiratory airflow through the left inspiratory lumen 220 and/or right inspiratory lumen 225 from a separate inspiratory airflow source than the ventilator system to which the connector 610 is connected. The separate inspiratory airflow source can include, for example, the inspiratory flow control system(s) 150, the inspiratory gas source(s) 160, the inspiratory gas provision system 490, the gas sources 932, the gas mixer(s) 930, the gas property control(s) 928, the capnometer(s) 926, the inspiratory mixture pressurizer 914, the buffer 912, the inspiratory mixture sensors 910, the gas property control 908, the pressure release valve 906, the inspiratory mixture pressurizer 924, the buffer 922, the inspiratory mixture sensors 920, the gas property control 918, the pressure release valve 916, or a combination thereof. In some examples, use of the connector 610 as an adapter 450 and/or as an adapter 455 can provide expiratory pressure and/or suction through the left expiratory lumen 520, and/or a right expiratory lumen 525 from a separate expiratory pressure control, which can include, for example, expiratory tube(s) 157, the expiratory flow control system(s) 155, the expiratory gas output(s) 165, the water trap 936, the capnometer 938, the expiratory mixture sensors 940, the buffer 942, the expiratory mixture pressurizer 944, the water trap 946, the capnometer 948, the expiratory mixture sensors 950, the buffer 952, the expiratory mixture pressurizer 954, or a combination thereof.

FIG. 7A is a conceptual diagram 700A illustrating a cross-section of an endotracheal tube (ETT) 120 that includes an expiratory lumen 705 that evacuates expiratory gas, a left inspiratory lumen 220 that provides inspiratory gas, and a right inspiratory lumen 225 that provides inspiratory gas. In some examples, the left inspiratory lumen 220 and the right inspiratory lumen 225 can pass freely through the ETT 120. In some examples, the left inspiratory lumen 220 and the right inspiratory lumen 225 can be coupled to one another within at least a portion of the ETT 120. In some examples, the left inspiratory lumen 220 and the right inspiratory lumen 225 can be two parts of a single lumen separated by a membrane, similarly to the separation of the first lumen 710 and the second lumen 715 by the membrane 720 in the tube 750 of FIG. 7B.

In some ventilator devices, the left inspiratory lumen 220 of FIG. 7A can instead be a left expiratory lumen 520, the right inspiratory lumen 225 of FIG. 7A can instead be a right expiratory lumen 525, and the expiratory lumen 705 can instead be an inspiratory lumen 540. An example of such a ventilator device is illustrated in FIG. 5D.

In some ventilator devices, the ETT 120 of FIG. 7A can also include a left expiratory lumen 520 and/or a right expiratory lumen 525 in addition to the left inspiratory lumen 220 and the right inspiratory lumen 225. In such ventilator devices, the ETT 120 itself can function as an expiratory lumen 705 as discussed above, as an inspiratory lumen 540, as both, or as neither. An example of such a ventilator device is illustrated in FIG. 5C.

FIG. 7B is a conceptual diagram 700B illustrating a cross-section of a tube 750 thlat includes a first lumen 710 and a second lumen 715 separated by a membrane 720. In some examples, the membrane 720 can be stretch-compliant, allowing for the lumens cross section area to accommodate current needs. If more flow is required via first lumen 710, the pressure within the first lumen 710 can be higher than in second lumen 715, and the compliant membrane 720 can allow for first lumen 710 to consume some of space previously taken up by second lumen 715. If more flow is required via second lumen 715, the pressure within the second lumen 715 can be higher than in the first lumen 710, and the compliant membrane 720 can allow for second lumen 715 to consume some of space previously taken up by first lumen 710.

In some examples, the tube 750 is an ETT 120. For instance, the first lumen 710 may be an inspiratory lumen, which may in some cases split into a left inspiratory lumen 220 and a right inspiratory lumen 225. The second lumen 715 may be an expiratory lumen 510, which may in some cases split into a left expiratory lumen 520 and a right expiratory lumen 525. The balloon 740 for the tube 750 may be an example of the balloon 205 for the ETT 120.

In some examples, the tube 750 includes the left inspiratory lumen 220 and the right inspiratory lumen 225 within the ETT 120. For instance, the first lumen 710 may be the left inspiratory lumen 220, and the second lumen 715 may be the right inspiratory lumen 225. The balloon 740 for the tube 750 need not be present, or may be an example of the balloon 205 for the ETT 120.

In some examples, the tube 750 includes the left lumens (the left inspiratory lumen 220 and the left expiratory lumen 520) of FIG. 5C. For instance, the first lumen 710 may be the left inspiratory lumen 220, and the second lumen 715 may be the left expiratory lumen 520. The balloon 740 for the tube 750 may be an example of the balloon 530 for the left lumens of FIG. 5C.

In some examples, the tube 750 includes the right lumens (the right inspiratory lumen 225 and the right expiratory lumen 525) of FIG. 5C. For instance, the first lumen 710 may be the right inspiratory lumen 225, and the second lumen 715 may be the right expiratory lumen 525. The balloon 740 for the tube 750 may be an example of the balloon 535 for the right lumens of FIG. 5C.

In some examples, the tube 750 includes an inspiratory tube 152 and an expiratory tube 157. For instance, the first lumen 710 may be the inspiratory tube 152, and the second lumen 715 may be the expiratory tube 157.

In some examples, the tube 750 includes two inspiratory tubes 152. For instance, the first lumen 710 may be a first inspiratory tube 152 that provides inspiratory gas(es) to a left inspiratory lumen 220 and/or from a first inspiratory flow control system 150 and/or a first set of inspiratory gas source(s) 160. The second lumen 715 may be a second inspiratory tube 152 that provides inspiratory gas(es) to a right inspiratory lumen 225 and/or from a second inspiratory flow control system 150 and/or a second set of inspiratory gas source(s) 160.

In some examples, the tube 750 includes two expiratory tubes 157. For instance, the first lumen 710 may be a first expiratory tube 157 that provides expiratory gas(es) from a left expiratory lumen 520 and/or to a first expiratory flow control system 155 and/or a first set of expiratory gas output(s) 165. The second lumen 715 may be a second expiratory tube 157 that provides expiratory gas(es) from a right expiratory lumen 525 and/or to a second expiratory flow control system 155 and/or a second set of expiratory gas output(s) 165.

Figure 8A:
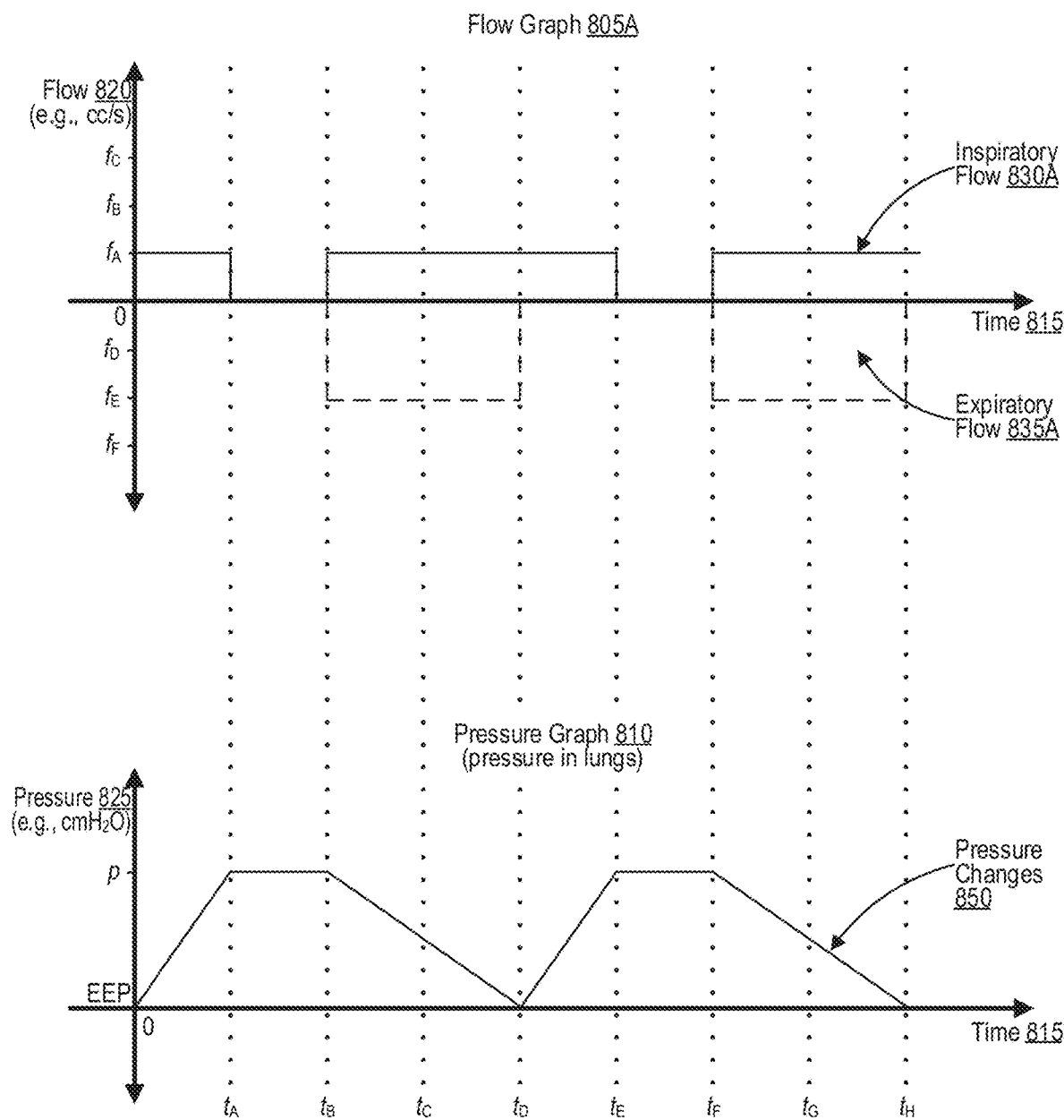
FIG. 8A is a graph diagram illustrating inspiratory flow, expiratory flow, and pressure changes over time in a ventilator system according to a first illustrative example.

FIG. 8A is a graph diagram 800A illustrating inspiratory flow 830A, expiratory flow 835A, and pressure changes 850 over time 815 in a ventilator system according to a first illustrative example. A flow graph 805A and a pressure graph 810A are illustrated in FIG. 8A. The flow graph 805A and the pressure graph 810A both include a shared horizontal time axis 815. The time axis 815 is the same for FIGS. 8A-8E, and includes times marked at time zero (0), at time $t_A$, at time $t_B$ after time $t_A$, at time $t_C$ after time $t_B$, at time $t_D$ after time $t_C$, at time $t_E$ after time $t_D$, at time $t_F$ after time $t_E$, at time $t_G$ after time $t_F$, and at time $t_H$ after time $t_G$. The timespan from time zero (0) to time $t_H$ is an example of portion of a longer period of time with multiple inspirations and multiple corresponding expirations.

The pressure graph 810 graphs pressure within a patient 105's lungs 130-135 (and/or another portion of the patient 105's airways) over time 815. The pressure graph 810 includes a vertical pressure axis 825. The vertical pressure axis 825 may measure pressure in centimeters of water ($cmH_2O$) or another pressure unit. Graphed pressure changes 850 in pressure 825 are tracked over time 815, and fluctuate from a value of zero (0) $cmH_2O$ to a value of p $cmH_2O$. The graphed pressure changes 850 of the pressure graph 810A span two (2) cycles of inspiration and expiration. The value of zero (0) $cmH_2O$, within the context of the graphed pressure changes 850, represent the pressure in the patient 105's airways when the patient 105 has fully exhaled, or been made to fully exhale by the pressurizer(s) of the ventilator system. The value of p $cmH_2O$, within the context of the graphed pressure changes 850, represent the pressure in the patient 105's airways when the patient 105 has fully inhaled, or been made to fully inhale by the pressurizer(s) of the ventilator system. In some examples, the pressure graphed in the pressure 825 may be a relative pressure rather than an absolute pressure. For instance, the pressure changes curve 850 reaching a pressure zero (0) may not mean that there is literally no pressure in the patient 105's lungs 130/135, but may refer to patient 105's lungs 130/135 having a baseline pressure level (e.g., atmospheric pressure, or end expiratory pressure (EEP) or positive end expiratory pressure (PEEP)). Likewise, the pressure changes curve 850 reaching the pressure p may not mean that p is the total pressure in the patient 105's lungs, but may simply refer to pressure p added to the baseline pressure level.

In some examples, the inspiratory flows 830A-830E represent sum of all inspiratory flows through all inspiratory lumens of a ventilator system (e.g., inspiratory lumens 220, 225, and/or 540). In some examples, the inspiratory flows 830A-830E represents individual inspiratory flows through an individual inspiratory lumen (e.g., inspiratory lumen 220, 225, or 540). In some examples, the inspiratory flows 830A-830E represent sum of all inspiratory flows through a subset of inspiratory lumens of a ventilator system (e.g., inspiratory lumens 220, 225, and/or 540). In some examples, the expiratory flows 835A-835E represent sum of all expiratory flows through all expiratory lumens of a ventilator system (e.g., expiratory lumens 520, 525, 510, and/or 705). In some examples, the expiratory flows 835A-835E represents individual expiratory flows through an individual expiratory lumen (e.g., expiratory lumen 520, 525, 510, or 705). In some examples, the expiratory flows 835A-835E represent sum of all expiratory flows through a subset of expiratory lumens of a ventilator system (e.g., expiratory lumens 520, 525, 510, and/or 705).

From time zero (0) to time $t_A$, the patient 105 is inhaling (and/or is being made to inhale by the pressurizer(s) of the ventilator system) and thus increasing pressure from an end expiratory pressure (EEP) up to pressure p. The increase in pressure from time zero (0) to time $t_A$ may be caused by an absolute value of an inspiratory flow (of the inspiratory flows 830A-830E) being higher than an absolute value of a corresponding expiratory flow (of the expiratory flows 835A-835E) from time zero (0) to time $t_A$. From time $t_A$ to time $t_B$, the patient 105 is holding their breath (and/or is being made to hold their breath by the pressurizer(s) of the ventilator system) and thus maintaining pressure p. Maintenance of the pressure p to hold the patient's breath, as in time $t_A$ to time $t_B$, may be referred to as inspiratory hold. The maintenance in pressure from time $t_A$ to time $t_B$ may be caused by an absolute value of an inspiratory flow (of the inspiratory flows 830A-830E) matching, or being substantially equal to, an absolute value of the corresponding expiratory flow (of the expiratory flows 835A-835E) from time $t_A$ to time $t_B$. From time $t_B$ to time $t_D$, the patient 105 is exhaling (and/or is being made to exhale by the pressurizer(s) of the ventilator system) thus reducing pressure from pressure p back down to the end expiratory pressure (EEP). The decrease in pressure from time $t_B$ to time $t_D$ may be caused by an absolute value of an inspiratory flow (of the inspiratory flows 830A-830E) being lower than an absolute value of the corresponding expiratory flow (of the expiratory flows 835A-835E) from time $t_B$ to time $t_D$ Time zero (0) to time $t_D$ represents a single inhale-exhale cycle. A second inhale-exhale cycle occurs from time $t_D$ to time $t_H$, and generally matches the first inhale-exhale cycle from time zero (0) to time $t_D$.

The pressure in the patient 105's airways when the patient 105 has fully exhaled may be referred to as an end expiratory pressure (EEP). In some cases, the EEP may be zero (0) cmH$_2$O. In some cases, the EEP may be higher than zero (0) cmH$_2$O. In some cases, the EEP may be less than zero (0) cmH$_2$O (e.g., may be a negative pressure). The value of the graphed pressure changes 850 at a given point in time may be a value relative to the pressure in the patient 105's airways when the patient 105 has fully exhaled (the EEP), rather than an absolute pressure value. The graphed pressure changes 850 in the pressure graph 810 are the same for FIGS. 8A-8E.

The flow graph 805A of FIG. 8A tracks an inspiratory flow 830A and an expiratory flow 835A over time 815. The inspiratory flow 830A and the expiratory flow 835A are tracked along a vertical flow axis 820. The vertical flow axis 820 may measure flow in cubic centimeters per second (cc/s) or another flow unit. The vertical flow axis 820 identifies zero (0) cc/s, three identified positive values ($f_A$, $f_B$, and $f_C$), and three identified negative values ($f_D$, $f_E$, and $f_F$). The positive values ($f_A$, $f_B$, and $f_C$) represent inspiratory flow into the patient 105's airways. The negative values ($f_D$, $f_E$, and $f_F$) represent expiratory flow out of the patient 105's airways. These flow values are used in the inspiratory flows 830A-830E and in the expiratory flows 835A-835E of FIGS. 8A-8E. In some examples, flow values $f_A$ and $f_D$ may share an absolute value, for instance $f_D$ with $f_A$ being multiplied by −1 and vice versa. In some examples, flow values $f_B$ and $f_E$ may share an absolute value, for instance $f_B$ with $f_E$ being multiplied by −1 and vice versa. In some examples, flow values $f_C$ and $f_F$ may share an absolute value, for instance $f_C$ with $f_F$ being multiplied by −1 and vice versa.

From time zero (0) to time $t_A$, during which the patient 105 is inhaling (and/or being made to inhale by the pressurizer(s) of the ventilator system) per the pressure changes 850, the inspiratory flow 830A provides relatively low continuous flow of inspiratory gas to the patient 105's airways at relatively low flow rate $f_A$ to provide the patient 105 with inspiratory gas to inhale during the inhalation from time zero (0) to time $t_A$. From time $t_A$ to time $t_B$, during which the patient 105 is holding his/her breath (and/or being made to hold his/her breath by the pressurizer(s) of the ventilator system) per the pressure changes 850, the inspiratory flow 830A provides zero (0) flow of inspiratory gas to the patient 105's airways at flow value zero (0) so as not to over pressurize the patient 105's airways. The period from time $t_A$ to time $t_B$ may be referred to as an "inspiratory hold," and may be when some of the gas exchange between the blood and alveoli gas (e.g., blood oxygenation, $CO_2$ extraction) happens in the patient 105's respiratory and circulatory systems, and/or where inspiratory flow may match expiratory flow for net zero flow to exchange expiratory gases (e.g., from the lungs 130/135 and including dead space 410 with suspected DCAs 425) for clean inspiratory gases. From time zero (0) to time $t_B$, the expiratory flow 835A is zero (0) and thus is not evacuating and/or receiving expiratory gas from the patient 105's airways, for instance so as not to interfere with inhalation. Net flow from time zero (0) to time $t_A$ may be positive, producing the inhalation. Net flow time $t_A$ to time $t_B$ may be zero, producing the inspiratory hold. From time is to time $t_D$, during which the patient 105 is exhaling (and/or being made to exhale by the pressurizer(s) of the ventilator system) per the pressure changes 850, the expiratory flow 835A evacuates and/or receives a relatively high continuous flow of expiratory gas from the patient 105's airways at relatively high (high absolute value) flow rate $f_E$. From time $t_B$ to time $t_D$, the absolute value of the expiratory flow $f_E$ may be higher than the absolute value of the inspiratory flow $f_A$, resulting in a net effect of expiration, which can to help evacuate $CO_2$-rich and $O_2$-deficient and potentially DCA 425—including expiratory gas from the patient 105's airways. From time $t_B$ to time $t_D$, during which the patient 105 is exhaling (and/or being made to exhale by the pressurizer(s) of the ventilator system) per the pressure changes 850, the inspiratory flow 830A provides relatively low continuous flow of inspiratory gas to the patient 105's airways at relatively low flow rate $f_A$ to maintain continuous airflow to perform gas exchange (exchanging contaminated expiratory air for clean inspiratory air) and clear out dead space 410 (and any DCAs 425 suspended therein) from the patient 105's lungs 130/135 and airways generally. Net flow from time is to time $t_D$ may be negative, producing the exhalation. The period of time from time zero (0) to time $t_D$ represents a single inhale-exhale cycle. A second inhale-exhale cycle occurs from time $t_D$ to time $t_H$. The continuous inspiratory and expiratory flows can provide continuous clearance and removal of dead space 410 with any DCAs 425 suspended therein.

During the expiration phases (from time $t_B$ to time $t_D$ and from time $t_F$ to time $t_H$), even though expiration happens, there is a continuous flow between inspiratory and expiratory lumens, which allows the ventilator system to clear out dead space 410 (along with any DCAs 425 included within the dead space 410). Furthermore, because the inspiratory lumens are separate from the expiratory lumens, inspiration lumens remain noncontaminated or less contaminated with virions or other DCAs 425, so still-healthy alveoli 325 (and their pneumocytes) or alveoli that already recovered have a chance to obtain noncontaminated air.

In the pressure graph 810 and the flow graphs 805A-805E of FIGS. 8A-8E, the length of expiration phases (from time $t_B$ to time $t_D$ and from time $t_F$ to time $t_H$) are longer than the length of the inspiration phases (from time zero to time $t_A$ and from time $t_D$ to time $t_E$) so there is enough time for expiration, and in some cases to prevent negative issues such as intrinsic positive end expiratory pressure (PEEP). Intrinsic PEEP can also be referred to as autoPEEP or PEEPi. Intrinsic PEEP can occur when expiratory time is shorter than the time needed to fully deflate the lungs, preventing the lung and chest wall from reaching an elastic equilibrium point, also referred to as "gas trapping."

FIG. 8B is a graph diagram 800B illustrating inspiratory flow 830B, expiratory flow 835B, and pressure changes 850 over time 815 in a ventilator system according to a second illustrative example. The pressure graph 810 of FIG. 8B matches the pressure graph 810 of FIG. 8A.

The flow graph 805B of FIG. 8B tracks an inspiratory flow 830B and an expiratory flow 835B over time 815, and along the vertical flow axis 820. In the flow graph 805B, the expiratory flow 835B evacuates and/or receives a relatively low continuous flow of expiratory gas from the patient 105's airways at relatively low (low absolute value) flow rate $f_D$ from time zero (0) to time $t_A$. In the flow graph 805B, the expiratory flow 835B evacuates and/or receives a relatively high flow of expiratory gas from the patient 105's airways at relatively high (relatively high absolute value) flow rate $f_E$ from time $t_A$ to time $t_D$. Under the expiratory flow 835B of FIG. 8B, the expiratory flow 835B continuously evacuates at least some of the $CO_2$-rich and $O_2$-deficient and potentially DCAs 425—including expiratory gas from the patient 105's airways, though the rate varies slightly by time. This continuously maintained expiratory flow 835B can allow the ventilator system to clear out dead space 410 (along with any DCAs 425 included within the dead space 410).

From time zero (0) to time $t_A$, during which the patient 105 is inhaling (and/or being made to inhale by the pressurizer(s) of the ventilator system) per the pressure changes 850, the inspiratory flow 830B provides relatively high continuous flow of inspiratory gas to the patient 105's airways at relatively high flow rate $f_B$ to ensure that the patient 105 has inspiratory gas to inhale during the inhalation from time zero (0) to time $t_A$. Net flow time zero (0) to time $t_A$ may be positive, producing the inhalation. Net flow time $t_A$ to time $t_B$ may be zero, producing the inspiratory hold. From time $t_A$ to time $t_B$, during which the patient 105 is holding his/her breath (and/or being made to hold his/her breath by the pressurizer(s) of the ventilator system) per the pressure changes 850, the inspiratory flow 830B still provides the relatively high continuous flow of inspiratory gas to the patient 105's airways at relatively high flow rate $f_B$ matching the relatively high flow of expiratory gas ($f_E$) from time $t_A$ to time $t_B$ to ensure clearance of dead space 410 (and any DCAs 425 therein) and help the patient's lungs 130-135 to perform gas exchange. From time $t_B$ to time $t_D$, during which the patient 105 is exhaling (and/or being made to exhale by the pressurizer(s) of the ventilator system) per the pressure changes 850, the inspiratory flow 830B provides relatively low continuous flow of inspiratory gas to the patient 105's airways at relatively low flow rate $f_A$ to continue to perform gas exchange (exchanging contaminated expiratory air for clean inspiratory air) and continue to clear out dead space 410 (and any DCAs 425 suspended therein) from the patient 105's lungs 130/135 and airways generally. Net flow time $t_B$ to time $t_D$ may be negative, producing the exhalation. With the relatively low flow rate $f_A$ of inspiratory flow 830B from time $t_B$ to time $t_D$, and the relatively high absolute flow rate $f_E$ of expiratory flow 835B from time $t_B$ to time $t_D$, the net effect can be a decrease in pressure in the lungs as illustrated in the pressure changes 850. Continuous inspiratory and expiratory flows can provide continuous clearance and removal of dead space 410 with any DCAs 425 suspended therein.

The period of time from time zero (0) to time $t_D$ represents a single inhale-exhale cycle. A second inhale-exhale cycle occurs from time $t_D$ to time $t_H$.

FIG. 8C is a graph diagram 800C illustrating inspiratory flow 830C, expiratory flow 835C, and pressure changes 850 over time 815 in a ventilator system according to a third illustrative example. The pressure graph 810 of FIG. 8C matches the pressure graphs 810 of FIGS. 8A and 8B.

The flow graph 805C of FIG. 8C tracks an inspiratory flow 830C and an expiratory flow 835C over time 815, and along the vertical flow axis 820.

From time zero (0) to time $t_A$, during which the patient 105 is inhaling (and/or being made to inhale his/her breath by the pressurizer(s) of the ventilator system) per the pressure changes 850, the expiratory flow 835C is approximately zero (0) or very low and the inspiratory flow 830C is not zero. From time $t_A$ to time $t_B$, during which the patient 105 is holding his/her breath (and/or being made to hold his/her breath by the pressurizer(s) of the ventilator system) per the pressure changes 850, the expiratory flow 835C evacuates and/or receives a relatively high continuous flow of expiratory gas from the patient 105's airways at relatively high (high absolute value) flow rate $f_E$ to help evacuate $CO_2$-rich and $O_2$-deficient and potentially DCA 425—including expiratory gas from the patient 105's airways. From time $t_B$ to time $t_D$, during which the patient 105 is exhaling (and/or being made to exhale by the pressurizer(s) of the ventilator system) per the pressure changes 850, the expiratory flow 835C evacuates and/or receives a relatively low continuous flow of expiratory gas from the patient 105's airways at relatively low (low absolute value) flow rate $f_D$ to help evacuate $CO_2$-rich and $O_2$-deficient and potentially DCA 425—including expiratory gas from the patient 105's airways. The high expiratory flow 835C in FIG. 8C maintained during the inspiratory flow can allow the ventilator system to rapidly clear out significant amounts dead space 410 (along with any DCAs 425 included within the dead space 410), and can be replaced with high inspiratory flow as discussed below to perform gas exchange within the patient 105's lungs 130/135 and airways generally.

From time zero (0) to time $t_A$, during which the patient 105 is inhaling (and/or being made to inhale by the pressurizer(s) of the ventilator system) per the pressure changes 850, the inspiratory flow 830C provides relatively low continuous flow of inspiratory gas to the patient 105's airways at relatively low flow rate $f_A$ to provide the patient 105 with inspiratory gas to inhale during the inhalation from time zero (0) to time $t_A$. Net flow time zero (0) to time $t_A$ may be positive, producing the inhalation. From time $t_A$ to time $t_B$, during which the patient 105 is holding his/her breath (and/or being made to hold his/her breath by the pressurizer(s) of the ventilator system) per the pressure changes 850, the inspiratory flow 830C provides a relatively high continuous flow of inspiratory gas to the patient 105's airways at relatively high flow rate $f_B$ to perform gas exchange (exchanging contaminated expiratory air for clean inspiratory air) and continue to clear out dead space 410 (and any DCAs 425 suspended therein) from the patient 105's lungs 130/135 and airways generally. Net flow from time $t_A$ to time $t_B$ may be zero, producing the inspiratory hold. The relatively high flow rate $f_B$ for the inspiratory flow 830C from time $t_A$ to time $t_B$ can be used to offset the relatively high flow rate $f_E$ for the expiratory flow 835C from time $t_A$ to time $t_B$. From time $t_B$ to time $t_D$, during which the patient 105 is exhaling (and/or being made to exhale by the pressurizer(s) of the ventilator system) per the pressure changes 850, the inspiratory flow 830C provides no flow, or very low continuous flow, of inspiratory gas to the patient 105's airways. Net flow time $t_B$ to time $t_D$ may be negative, producing the exhalation. Because expiratory flow 835C is still active from time $t_D$ to time $t_E$, the clearance of dead space 410 and DCAs 425 continues from time $t_D$ to time $t_E$. However, the clearance can be lower and/or slower during the time $t_B$ to $t_D$ in graph 805C than as it was during the time $t_B$ to $t_D$ in ventilatory system modes of operation presented on graphs 805A-805B, as there is no (or very low) inspiratory flow in ventilatory system mode as shown on graph 805C during the time $t_B$ to $t_D$. Continuous inspiratory and expiratory flows can provide continuous clearance and removal of dead space 410 with any DCAs 425 suspended therein.

The period of time from time zero (0) to time $t_D$ represents a single inhale-exhale cycle. A second inhale-exhale cycle occurs from time $t_D$ to time $t_H$.

Figure 8D:
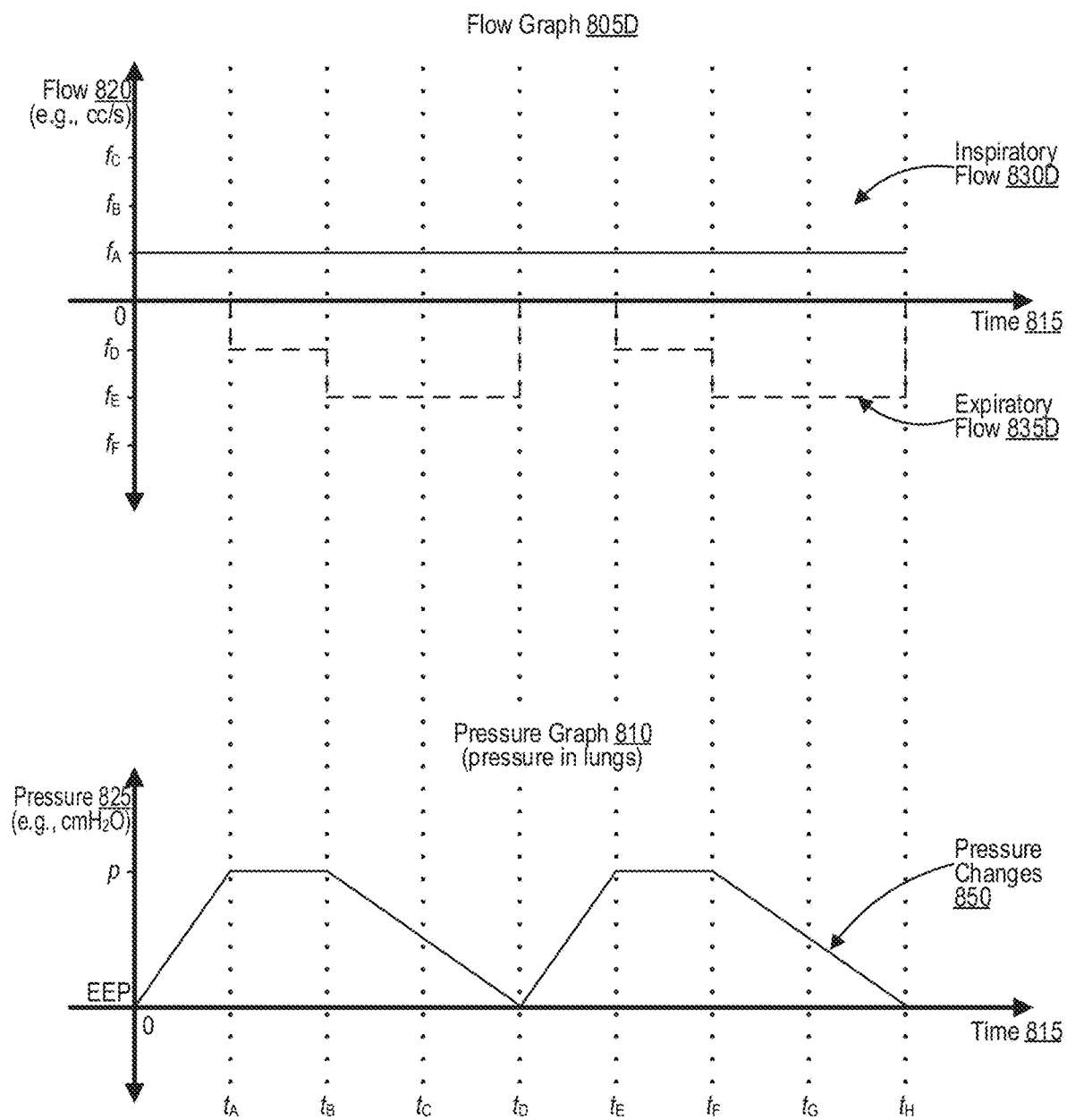
FIG. 8D is a graph diagram illustrating inspiratory flow, expiratory flow, and pressure changes over time in a ventilator system according to a fourth illustrative example.

FIG. 8D is a graph diagram 800D illustrating inspiratory flow 830D, expiratory flow 835D, and pressure changes 850 over time 815 in a ventilator system according to a fourth illustrative example. The pressure graph 810 of FIG. 8D matches the pressure graphs 810 of FIGS. 8A-8C.

The flow graph 805D of FIG. 8D tracks an inspiratory flow 830D and an expiratory flow 835D over time 815, and along the vertical flow axis 820. In the flow graph 805D, the inspiratory flow 830D provides relatively low continuous flow of inspiratory gas to the patient 105's airways at relatively low flow rate $f_A$ during the entire period of time 815 from time zero (0) onward, to continuously provide the patient 105 with inspiratory gas to inhale during inhalations and/or to perform gas exchange and dead space clearance with suspended DCAc.

From time zero (0) to time $t_A$, during which the patient 105 is inhaling (and/or being made to inhale by the pressurizer(s) of the ventilator system) per the pressure changes 850, the expiratory flow 830D is approximately zero (0), or very low. Net flow from time zero (0) to time $t_A$ may be positive, producing the inhalation. From time $t_A$ to time $t_B$, during which the patient 105 is holding his/her breath (and/or being made to hold his/her breath by the pressurizer(s) of the ventilator system) per the pressure changes 850, the expiratory flow 835D the expiratory flow 835D evacuates and/or receives a relatively low continuous flow of expiratory gas from the patient 105's airways at relatively low (low absolute value) flow rate $f_D$ to evacuate $CO_2$-rich and $O_2$-deficient and potentially DCA 425—including expiratory gas from the patient 105's airways. Net flow time $t_A$ to time $t_B$ may be zero, producing the inspiratory hold. From time $t_B$ to time $t_D$, during which the patient 105 is exhaling (and/or being made to exhale by the pressurizer(s) of the ventilator system) per the pressure changes 850, the expiratory flow 835D evacuates and/or receives a relatively high continuous flow of expiratory gas from the patient 105's airways at relatively high (high absolute value) flow rate $f_E$ producing exhalation and evacuating $CO_2$-rich and $O_2$-deficient and maintain high clearance of dead space with suspended within DCA 425-$s$. Net flow time $t_B$ to time $t_D$ may be negative, producing the exhalation. The high expiratory flow 835D in FIG. 8D can allow the ventilator system to rapidly clear out significant amounts dead space 410 (along with any DCAs 425 included within the dead space 410). Continuous inspiratory and expiratory flows can provide continuous clearance and removal of dead space 410 with any DCAs 425 suspended therein.

The period of time from time zero (0) to time $t_D$ represents a single inhale-exhale cycle. A second inhale-exhale cycle occurs from time $t_D$ to time $t_H$.

In some examples, the inspiratory flow 830D and/or the expiratory flow 835D can be used with ventilator systems that are similar to the ventilator systems of FIGS. 4A-4C but that are modified (e.g., using one or more adapters and/or connecter, for example connected 610 from FIG. 6.) to be more like the ventilator systems of FIGS. 5A-5C (e.g., by adding left inspiratory lumens 220 and right inspiratory lumens 225 and one or more expiratory lumens 510/520/525 separate from the inspiratory lumens 220-225 and/or separate from any expiratory lumens).

FIG. 8E is a graph diagram 800E illustrating inspiratory flow 830E, expiratory flow 835E, and pressure changes 850 over time 815 in a ventilator system according to a fifth illustrative example. The pressure graph 810 of FIG. 8E matches the pressure graphs 810 of FIGS. 8A-8D.

From time zero (0) to time $t_A$, during which the patient 105 is inhaling (and/or being made to inhale by the pressurizer(s) of the ventilator system) per the pressure changes 850, the expiratory flow 835E evacuates and/or receives a relatively low continuous flow of expiratory gas from the patient 105's airways at relatively low (low absolute value) flow rate $f_D$ to help evacuate $CO_2$-rich and $O_2$-deficient and potentially DCA 425—including expiratory gas from the patient 105's airways. From time $t_A$ to time $t_B$, during which the patient 105 is holding his/her breath (and/or being made to hold his/her breath by the pressurizer(s) of the ventilator system) per the pressure changes 850, the expiratory flow 835E evacuates and/or receives a relatively high continuous flow of expiratory gas from the patient 105's airways at relatively high (high absolute value) flow rate $f_E$ to help evacuate $CO_2$-rich and $O_2$-deficient and potentially DCA 425—including expiratory gas from the patient 105's airways. From time $t_B$ to time $t_D$, during which the patient 105 is exhaling (and/or being made to exhale by the pressurizer(s) of the ventilator system) per the pressure changes 850, the expiratory flow 835C evacuates and/or receives a very high continuous flow of expiratory gas from the patient 105's airways at very high (very high absolute value) flow rate $f_F$ to help evacuate $CO_2$-rich and $O_2$-deficient and potentially DCA 425—including expiratory gas from the patient 105's airways. The high expiratory flow 835C in FIG. 8E can allow the ventilator system to rapidly clear out significant amounts dead space 410 (along with any DCAs 425 included within the dead space 410).

From time zero (0) to time $t_A$, during which the patient 105 is inhaling (and/or being made to inhale by the pressurizer(s) of the ventilator system) per the pressure changes 850, the inspiratory flow 830E provides very high continuous flow of inspiratory gas to the patient 105's airways at very high flow rate $f_C$ to provide the patient 105 with inspiratory gas to inhale during the inhalation from time zero (0) to time $t_A$ and to offset the expiratory flow 835E. Net flow from time zero (0) to time $t_A$ may be positive, producing the inhalation. From time $t_A$ to time $t_B$, during which the patient 105 is holding his/her breath (and/or being made to hold his/her breath by the pressurizer(s) of the ventilator system) per the pressure changes 850, the inspiratory flow 830E provides a relatively high continuous flow of inspiratory gas to the patient 105's airways at relatively high flow rate $f_B$ to perform gas exchange (exchanging contaminated expiratory air for clean inspiratory air) and continue to clear out dead space 410 (and any DCAs 425 suspended therein) from the patient 105's lungs 130/135 and airways generally. Net flow time $t_A$ to time $t_B$ may be zero, producing the inspiratory hold. From time $t_B$ to time $t_D$, during which the patient 105 is exhaling (and/or being made to exhale by the pressurizer(s) of the ventilator system) per the pressure changes 850, the inspiratory flow 830E provides relatively low continuous flow of inspiratory gas to the patient 105's airways at relatively low flow rate $f_A$ to continue to perform gas exchange. Net flow time $t_B$ to time $t_D$ may be negative, producing the exhalation. Continuous inspiratory and expiratory flows can provide continuous clearance and removal of dead space 410 with any DCAs 425 suspended therein through the entire inhale-exhale cycle from time zero (0) to time $t_D$.

The period of time from time zero (0) to time $t_D$ represents a single inhale-exhale cycle. A second inhale-exhale cycle occurs from time $t_D$ to time $t_H$.

While the inspiratory flows 830A-830E and the expiratory flows 835A-835E of FIGS. 8A-8E are illustrated as step functions that instantaneously step between continuous flow rate values, it should be understood that changes in flow rate in the inspiratory flows 830A-830E and the expiratory flows 835A-835E may occur more gradually. Furthermore, it should be understood that flow rates illustrated as continuous in the inspiratory flows 830A-830E and the expiratory flows 835A-835E of FIGS. 8A-8E may include fluctuations and curves not illustrated in FIGS. 8A-8E.

In some examples, the inspiratory flow 830A may be paired with any one of the expiratory flows 835A-835E, or a combination thereof. In some examples, the inspiratory flow 830B may be paired with any one of the expiratory flows 835A-835E, or a combination thereof. In some examples, the inspiratory flow 830C may be paired with any one of the expiratory flows 835A-835E, or a combination thereof. In some examples, the inspiratory flow 830D may be paired with any one of the expiratory flows 835A-835E, or a combination thereof. In some examples, the inspiratory flow 830E may be paired with any one of the expiratory flows 835A-835E, or a combination thereof.

In some examples, the expiratory flow 835A may be paired with any one of the inspiratory flows 830A-830E, or a combination thereof. In some examples, the expiratory flow 835B may be paired with any one of the inspiratory flows 830A-830E, or a combination thereof. In some examples, the expiratory flow 835C may be paired with any one of the inspiratory flows 830A-830E, or a combination thereof. In some examples, the expiratory flow 835D may be paired with any one of the inspiratory flows 830A-830E, or a combination thereof. In some examples, the expiratory flow 835E may be paired with any one of the inspiratory flows 830A-830E, or a combination thereof.

Figure 9A:
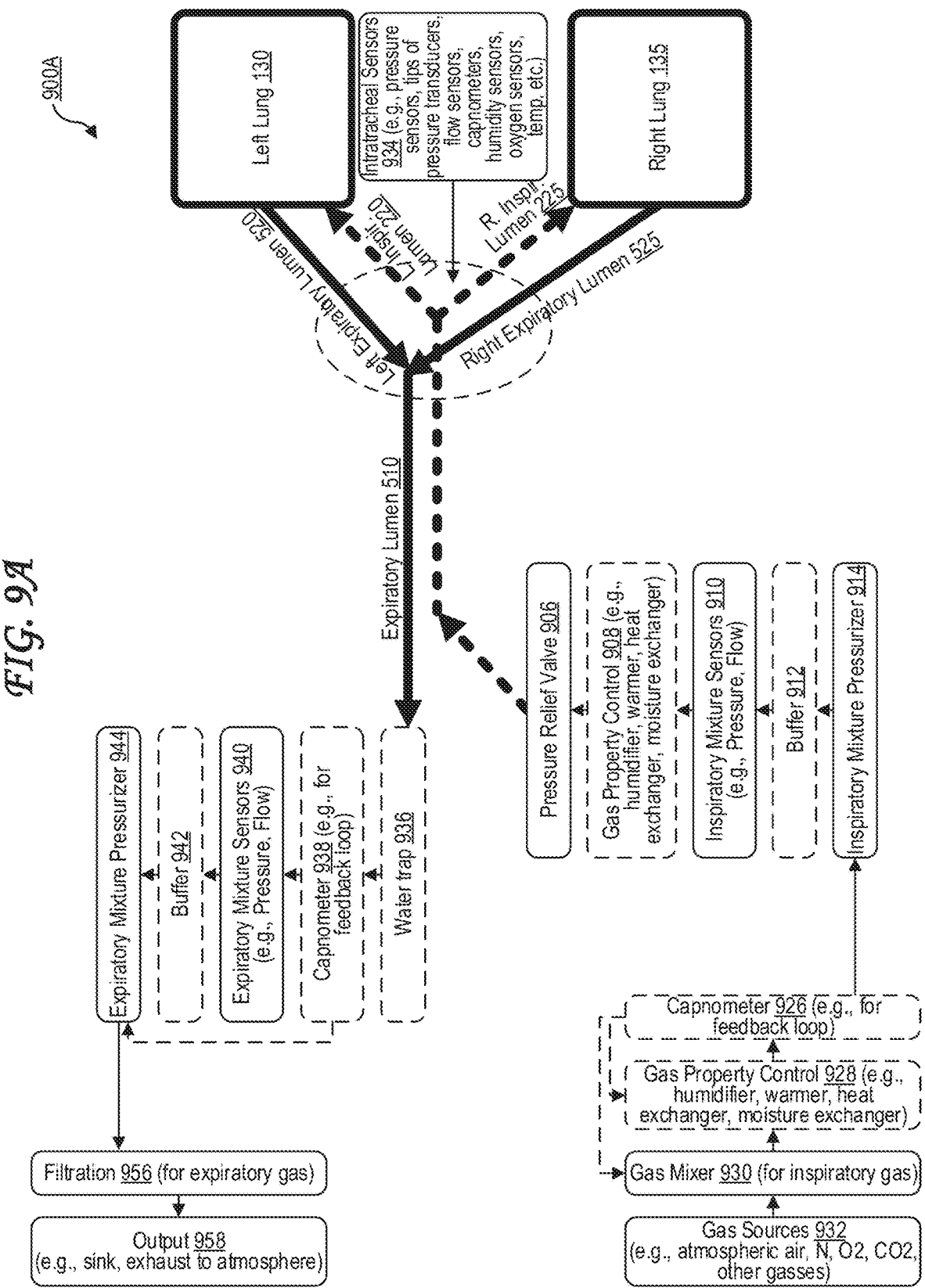
FIG. 9A is a block diagram illustrating an architecture of an exemplary ventilator system that includes an inspiratory control system that provides inspiratory gas to a left lung and a right lung through a left inspiratory lumen and a right inspiratory lumen, and an expiratory control system that evacuates expiratory gas from the left lung and the right lung through one or more expiratory lumens.

FIG. 9A is a block diagram 900A illustrating an architecture of an exemplary ventilator system that includes an inspiratory control system that provides inspiratory gas to a left lung 130 and a right lung 135 through a left inspiratory lumen 220 and a right inspiratory lumen 225, and an expiratory control system that evacuates expiratory gas from the left lung 130 and the right lung 135 through one or more expiratory lumens 510/520/525.

An inspiratory gas supply system of the ventilator system of FIG. 9A, illustrated in the lower-left corner of FIG. 9A, includes one or more gas sources 932. The one or more gas sources 932 may correspond to the inspiratory gas sources 160 of FIG. 1. For example, the one or more inspiratory gas sources 160 can include an oxygen ($O_2$) gas source, a nitrogen (N) gas source, a carbon dioxide ($CO_2$) gas source, an argon (Ar) gas source, one or more gas sources for one or more drugs (in gaseous and/or aerosolized form), one or more gas sources for one or more other elemental gases, one or more gas sources for one or more other molecular gases, an pre-mixed atmospheric gas source, or a combination thereof.

The pre-mixed atmospheric gas source can include, for example, filtered atmospheric air. In some examples, a pre-mixed atmospheric gas can be sufficient to use as an inspiratory gas mixture, or as a portion of the inspiratory gas mixture (e.g., with some nitrogen (N) and/or oxygen ($O_2$) added). In some examples, a pre-mixed atmospheric gas may include approximately 21% oxygen ($O_2$), 78% nitrogen (N), and less than 1% of carbon dioxide ($CO_2$). Filters by the inspiratory gas supply system may include n100, HEPA, or higher degree gas filtration filters, a IJV light for decontamination, and other filters and cleaners.

Gas sources for individual elements or molecules, such as oxygen ($O_2$), nitrogen (N), carbon dioxide ($CO_2$), argon (Ar), or other elements or molecules discussed herein, can be stored in the gas source at a defined concentration. The concentration can be 100%, or can be a value less than 100% (in which case the element or molecule may be mixed with atmospheric air, for example).

The inspiratory gas supply system may include a gas mixer 930 for mixing gases from the gas sources 932 to produce an inspiratory gas mixture, which may be known as an inspiratory gas, an inspiratory mixture, an inspiratory aerosol, or some combination thereof. The gas mixer 930 may include one or more gas equalizing systems, one or more proportional valves, one or more calibrated solenoid flow valves, or a combination thereof.

The gas mixer 930 may, for example, mix oxygen ($O_2$), nitrogen (N), carbon dioxide ($CO_2$), argon (Ar), one or more drugs (in gaseous and/or aerosolized form), one or more one or more other elemental gases, one or more other molecular gases, a pre-mixed atmospheric gas source, or a combination thereof. Even though it may seem counter-intuitive, it may be useful to include carbon dioxide ($CO_2$) in the inspiratory gas mixture when carbon dioxide ($CO_2$) is being evacuated at a high rate (due to continues or almost continues flow during the inhalation-exhalation cycle through both inspiratory and expiratory lumens) from the patient 105's airways, as lack of carbon dioxide ($CO_2$) can increase alkalinity, pushing pH too high, and can cause negative effects such as alkalosis.

In some examples, the gas mixer 930 can mix one or more liquids and/or one or more particulate solids into the one or more gases, for example in aerosolized and/or particularized and/or nebulized form. Sources for the liquids and/or solids can be stored along with the gas sources 932. The one or more liquids can include water ($H2O$), one or more drugs in liquid form, one or more other liquids, or a combination thereof. The one or more particulate solids can include one or more drugs in particulate solid form, one or more other particulate solids, or a combination thereof. The gas mixer 930 can include an aerosolizer and/or nebulizer and/or particulatizer to aerosolize and/or nebulize and/or particulatize the one or more liquids and/or the one or more solids. The gas mixer 930 can mix the one or more aerosolized and/or particulate liquids and/or solids into the one or more inspiratory gases.

The gas mixer 930 can mix gases and/or liquids and/or particulate solids from the one or gas sources 932 at one or more predetermined ratios and/or proportions. The gas mixer 930 can mix inspiratory gases and/or liquids and/or particulate solids from the one or more gas sources 930 at one or more predetermined ratios and/or proportions to simulate the natural ratios and/or proportions of these gases in Earth's atmosphere or other ratios and/or proportions that may be selected or recommended by an operator, by an artificial intelligence algorithm (e.g., one or more trained machine learning models, one or more trained neural networks, or a combination thereof), or a combination thereof. The gas mixer 930 can mix inspiratory gases and/or liquids and/or particulate solids from the gas sources 932 at one or more predetermined ratios and/or proportions that increase or decrease a relative quantity of one or more specific gases (e.g., increased oxygen, decreased carbon monoxide) relative to the natural ratios and/or proportions of these gases in Earth's atmosphere or other ratios and/or proportions that may be selected or recommended by an operator, by an artificial intelligence algorithm (e.g., one or more trained machine learning models, one or more trained neural networks, or a combination thereof), or a combination thereof. The mixture mixed by the gas mixer 903 can be referred to as the inspiratory mixture, the inspiratory gas, the inspiratory gas mixture, the inspiratory fluid mixture, the inspiratory fluid, the inspiratory substance, the inspiratory air, the inspiratory aerosol, or some combination thereof. The ratios at which the different gases are present in the inspiratory mixture may be set by a user 190 through an interface 175.

In some examples, the gas sources 932 can include stable and known pressures of each of the gases provided to the gas mixer 930. The gas mixer 930 can adjust flows of each gas by adjusting flow valves of for each of gases based on feedback loop based on sensor data from the capnometer 926 and/or other sensors (e.g., the inspiratory mixture sensors 910, the capnometer 938, the expiratory mixture sensors 940, and/or the intratracheal sensors 934).

The inspiratory gas supply system may include a gas property control 928. The gas property control 928 can include a humidifier and/or a moisture exchanger and/or a moisture trap to control (e.g., increase or decrease) the humidity of the inspiratory gas before the inspiratory mixture is provided to the patient 105's airways. The gas property control 928 can include warmer and/or a heat exchanger to control (e.g., increase or decrease) the temperature of the inspiratory gas before the inspiratory mixture is provided to the patient 105's airways.

The inspiratory gas supply system may include a capnometer 926, which may measure a concentration of carbon dioxide in the inspiratory mixture. Sensor data (e.g., readings/measurements) from the capnometer 926 may be provided to the gas mixer 930 as feedback. The gas mixer 930 may adjust the amount of carbon dioxide and/or other gases in the inspiratory mixture based on the sensor data from the capnometer 926.

An inspiratory gas delivery system of the ventilator system of FIG. 9A, illustrated in the lower-middle of FIG. 9A, includes an inspiratory mixture pressurizer 914. The inspiratory mixture pressurizer 914 can be electronically controlled, for example using the controller 170. The inspiratory mixture pressurizer 914 provides pressure to the inspiratory mixture. The amount of pressure provided by the inspiratory mixture pressurizer 914 to the inspiratory mixture can be programmable, for example based on inputs from the user 190 to the interface 175, based on automated pre-programmed reactions of the controller 170 to sensor data reaching/crossing thresholds or reaching/crossing into or out of a range, or a combination thereof. The amount of pressure provided by the inspiratory mixture pressurizer 914 to the inspiratory mixture can be based on sensor data from the capnometer 926, the inspiratory mixture sensors 910, the intratracheal sensors 934, the capnometer 938, and/or the expiratory mixture sensors 940. The pressure programmed for the inspiratory mixture pressurizer 914 to apply may be defined in terms of pressure/time (as in the pressure graphs 810 of FIGS. 8A-8E) and/or flow/time (as in the flow graphs 805A-805E of FIGS. 8A-8E). The inspiratory mixture pressurizer 914 can react to program, manual control by operator, alarms, thresholds, ranges, and safety settings including, but not limited to one or more maximum inspiratory mixture pressure thresholds, one or more minimum inspiratory mixture pressure thresholds, one or more safe inspiratory mixture pressure ranges, one or more unsafe inspiratory mixture pressure ranges, or a combination thereof. Multiple pre-set thresholds and ranges may exist because certain thresholds may differ based on whether a patient 105 has a healthy respiratory system or not, and what types of diseases or conditions a patient 105 may be suffering from. The thresholds may correspond to positive end expiratory pressure (PEEP). In some examples, a higher PEEP may be desirable. In some examples, a lower PEEP may be desirable.

The inspiratory gas delivery system may include one or more buffers 912. The buffers 912 may store the inspiratory mixture while the inspiratory mixture pressurizer 914 pressurizes the inspiratory mixture. The buffers 912 may store additional inspiratory mixture in case the inspiratory gas delivery system does not receive the inspiratory mixture or receives less than needed of the inspiratory mixture for a short period from the inspiratory gas supply system.

The inspiratory gas delivery system may include one or more inspiratory mixture sensors 910. The inspiratory mixture sensors 910 may include pressure sensors, pressure transducers, flow sensors, temperature sensors, humidity sensors, capnometers, oximeters, or combinations thereof.

The inspiratory gas delivery system may include a gas property control 908. The gas property control 908 can include a humidifier and/or a moisture exchanger and/or a moisture trap to control (e.g., increase or decrease) the humidity of the inspiratory gas before the inspiratory mixture is provided to the patient 105's airways. The gas property control 908 can include warmer and/or a heat exchanger to control (e.g., increase or decrease) the temperature of the inspiratory gas before the inspiratory mixture is provided to the patient 105's airways.

The inspiratory gas delivery system may include a pressure release valve 906. The pressure release valve 906 may release the inspiratory mixture into one or more inspiratory lumens. In the ventilator system of FIG. 9A, a single inspiratory tube or inspiratory lumen branches into a left inspiratory lumen 220, which provides the inspiratory mixture to the left lung 130, and a right inspiratory lumen 225, which provides the inspiratory mixture to the right lung 135. The inspiratory tube and/or inspiratory lumens are illustrated using thick dashed lines in FIGS. 9A-9B. The thick dashed lines include arrowheads pointing in the direction of inspiratory flow toward the lungs 130-135.

The ventilator system of FIGS. 9A-9B includes one or more intratracheal sensors 934 that monitor pressure, flow, $CO_2$ level, oxygen level, humidity, temperature, and/or other properties at the carina of the trachea 115 and/or one or more other portions of the trachea 115. The one or more intratracheal sensors 934 may be used to maintain desired positive end expiratory pressure (PEEP) where it is needed the most, still allowing the ventilator system of FIGS. 9A-9B to apply negative or reduced pressure. Another way to measure PEEP is to measure it by expiratory mixture sensors 940/950. Negative pressures may need to be applied to expiratory lumen(s) (e.g., expiratory lumen 510 of FIG. 9A and/or expiratory lumens 520 and 525 of FIG. 9B) by the expiratory mixture pressurizers 994/954 to overcome the flow resistance in expiratory lumen(s) 520-525 as the expiratory mixture(s) is/are leaving the lungs 130-135 via airways and via expiratory lumen(s) 520-525. Such negative, or lower than PEEP pressure, applied to expiratory lumens will allow for more efficient expiratory mixture(s) evacuation from lungs 130-135 via expiratory lumen(s) 520-525. This sometimes may be necessary to maintain required shorter length of the expiratory phase, to maintain pre-determined and/or recommended and/or preset by operator higher respiratory rate. The intratracheal sensors 934 can include pressure sensors and/or one or more tips of one or more pressure transducers. The intratracheal sensors 934 can include pressure sensors as well as other sensors (e.g., flow, temperature, humidity, capnometer, oxygen sensor, and/or other gas properties).

The ventilator system of FIGS. 9A-9B includes one or more expiratory lumens that evacuate and/or receive expiratory gas(es) from the left lung 130 and/or the right lung 135. The one or more expiratory lumens can include a single expiratory lumen 510 as in FIGS. 5A-5B. The a left expiratory lumen 520 and a right expiratory lumen 525 as in FIG. 5C. The one or more expiratory lumens are illustrated using thick solid lines in FIGS. 9A-9B. The thick solid lines include arrowheads pointing in the direction of expiratory flow away from the lungs 130-135.

An expiratory gas receipt system of the ventilator system of FIG. 9A, illustrated in the upper-middle of FIG. 9A, can include a water trap 936 or moisture trap that traps water, moisture, and/or other liquids (e.g., mucous) that the expiratory gas receipt system can separate from the expiratory gas. The expiratory gas receipt system can include a capnometer 938, which may measure carbon dioxide concentration in the expiratory gas(es). The sensor data from the capnometer 938 can be used for a feedback loop, for example to the expiratory mixture pressurizer 944.

The expiratory gas receipt system can include one or more expiratory mixture sensors 940 that can measure properties of the expiratory gas(es). The one or more expiratory mixture sensors 940 may include pressure sensors, pressure transducers. flow sensors, temperature sensors, humidity sensors, capnometers, oximeters, or combinations thereof.

The expiratory gas receipt system can include an expiratory mixture pressurizer 944. The expiratory mixture pressurizer 944 can provide pressure, for instance negative pressure (e.g., providing suction), to the one or more expiratory lumens 510/520/525. Negative pressure can allow for receipt and/or evacuation of more expiratory gas(es) from the left lung 130 and/or the right lung 135, and DCAs 425 included within. For example, negative pressure can allow for receipt and/or evacuation of more expiratory gas(es) from the dead spaces 410, and DCAs 425 included within. Negative pressure can allow for flow of expiratory gas(es) from the lungs 130-135 to occur at a faster rate. The expiratory mixture pressurizer 944 can be electronically controlled, for example via a controller 170. The expiratory mixture pressurizer 944 can include, for example, a rotary compressor, a turbine, a suction device, or a combination thereof. The expiratory gas receipt system can include a buffer 942, which may for example be used by the expiratory mixture pressurizer 944 for providing negative pressure on the one or more expiratory lumens.

The amount of expiratory pressure provided by the expiratory mixture pressurizer 944 can be programmable, for example based on inputs from the user 190 to the interface 175, based on automated pre-programmed reactions of the controller 170 to sensor data reaching/crossing thresholds or reaching/crossing into or out of a range, or a combination thereof. In some examples, the controller 170 that controls the expiratory mixture pressurizer 944 can adjust expiratory pressure based on sensor data from the capnometer 926, the inspiratory mixture sensors 910, the intratracheal sensors 934, the capnometer 938, the expiratory mixture sensors 940, or a combination thereof. The amount of expiratory pressure provided by the expiratory mixture pressurizer 944 can be programmable pressure/time (as in the pressure graphs 810 of FIGS. 8A-8E) and/or flow/time (as in the flow graphs 805A-805E of FIGS. 8A-8E). The expiratory mixture pressurizer 944 can react to alarms, thresholds, ranges, and safety settings including, but not limited to one or more maximum expiratory mixture pressure thresholds, one or more minimum expiratory mixture pressure thresholds, one or more safe expiratory mixture pressure ranges, one or more unsafe expiratory mixture pressure ranges, or a combination thereof. Multiple pre-set thresholds and ranges may exist because certain thresholds may differ based on whether a patient 105 has a healthy respiratory system or not, and what types of diseases or conditions a patient 105 may be suffering from. Expiratory pressure may be set to maintain a PEEP pressure above a threshold (e.g., a positive PEEP pressure) as measured at the intratracheal pressure sensors 934 or in any other way (for example as measured by expiratory mixture sensors 940/950). An example minimum expiratory pressure may be 5 $cmH_2O$, as less than that may be detrimental to pulmonary function or insufficient to maintain proper oxygenation in certain clinical scenarios. Specific expiratory pressures may be desirable to treat certain diseases. For example, to treat diseases such as ARDS, expiratory pressure of 12 $cmH_2O$ may be useful.

An expiratory gas removal system of the ventilator system of FIG. 9A, illustrated in the upper-left corner of FIG. 9A, can includes a filtration system 956 that filters the expiratory gases, for example to remove DCAs 425 and/or harmful contaminants. The expiratory gas removal system can include an output 958, which may include a gas sink/reservoir and/or an exhaust (e.g., to the atmosphere). In some examples, certain filtered and/or safe portions of the expiratory gases can be output using an exhaust, while dangerous portions of the expiratory gases (e.g., including DCAs 425 corresponding to highly infectious/contagious/deadly diseases) can be output to a sink or reservoir to prevent infecting or contaminating other individuals.

In some examples, the one or more expiratory lumens and/or one or more inspiratory lumens may include stiff walls to withstand positive pressure supplied by the inspiratory mixture pressurizer 914 and/or to withstand negative pressure supplied by the expiratory mixture pressurizer 944. In some examples, the one or more expiratory lumens and/or one or more inspiratory lumens may, at least in some areas, be surrounded by a tube, such as the ETT 120. The tube may include stiff walls to withstand positive pressure supplied by the inspiratory mixture pressurizer 914 and/or to withstand negative pressure supplied by the expiratory mixture pressurizer 944.

In some examples, the inspiratory flow control system 150 of FIG. 1 may include at least a subset of the inspiratory gas supply system and/or at least a subset of the inspiratory gas delivery system of FIG. 9A. In some examples, the inspiratory gas source(s) 160 of FIG. 1 may include at least a subset of the inspiratory gas supply system and/or at least a subset of the inspiratory gas delivery system of FIG. 9A. In some examples, the expiratory flow control system 155 of FIG. 1 may include at least a subset of the expiratory gas receipt system and/or at least a subset of the expiratory gas removal system of FIG. 9A. In some examples, the expiratory output(s) 165 of FIG. 1 may include at least a subset of the expiratory gas receipt system and/or at least a subset of the expiratory gas removal system of FIG. 9A.

FIG. 9B is a block diagram 900B illustrating an architecture of an exemplary ventilator system that includes a left inspiratory control system that provides inspiratory gas to a left lung 130 through a left inspiratory lumen 220, a right inspiratory control system that provides inspiratory gas to a right lung 135 through a right inspiratory lumen 225, a left expiratory control system that evacuates expiratory gas from a left lung 130 through a left expiratory lumen 520, and a right expiratory control system that evacuates expiratory gas from a right lung 135 through a right expiratory lumen 525. The ventilator system of FIG. 9B shares many components and traits with the ventilator system of FIG. 9A.

However, the ventilator system of FIG. 9B includes a left inspiratory lumen 220 with its own left inspiratory gas delivery system (with elements 916-924) and a right inspiratory lumen 225 with its own right inspiratory gas delivery system (with elements 906-914). The left inspiratory gas delivery system can include an inspiratory mixture pressurizer 924, buffer 922, inspiratory mixture sensors 920, gas property control 918, and pressure release valve 916. These elements can function similarly to corresponding elements in the right inspiratory gas delivery system (and of FIG. 9A), such as the inspiratory mixture pressurizer 914, the buffer 912, the inspiratory mixture sensors 910, gas property control 908, and pressure release valve 906.

While the ventilator system of FIG. 9B is illustrated with the left inspiratory gas delivery system and right inspiratory gas delivery system both supplied with inspiratory mixture by a shared inspiratory gas supply system (with elements 926-932), this need not be the case. In some examples, the left inspiratory gas delivery system may include its own left inspiratory gas supply system, and the right inspiratory gas delivery system may include its own right inspiratory gas supply system.

The ventilator system of FIG. 9B also includes a left expiratory lumen 520 with its own left expiratory gas receipt system (with elements 936-944) and a right inspiratory lumen 525 with its own inspiratory gas delivery system (with elements 946-954). The right inspiratory gas delivery system can include a water trap 946, capnometer 948, expiratory mixture sensors 950, buffer 952, and/or expiratory mixture pressurizer 954. These elements can function similarly to corresponding elements in the left expiratory gas delivery system (and of FIG. 9A), such as the water trap 936, capnometer 938, expiratory mixture sensors 940, buffer 942, and/or expiratory mixture pressurizer 944.

While the ventilator system of FIG. 9B is illustrated with the left expiratory gas receipt system and right expiratory gas receipt system both outputting expiratory mixture to a shared expiratory gas removal system (with elements 956-958), this need not be the case. In some examples, the left expiratory gas receipt system may include its own left expiratory gas removal system, and the right expiratory gas receipt system may include its own right expiratory gas removal system.

The expiratory Mixture collectively from all or some Expiratory Lumens, or separately from all or some Expiratory lumens, in all examples, can be analyzed, per clinical needs, for white cell count, epithelial cells count, red cell count, with culture, stains, microscopic examination, polymerase chain reaction, any other test, all quantitative and qualitative, in appropriate clinical scenarios, to diagnose, to follow up and compare disease activity and/or response to treatment in all, or some portions of the lungs.

The separate left inspiratory gas delivery system and right inspiratory gas delivery system separately supply pressurized inspiratory mixture to the left lung 130 and right lung 135, respectively, through the left inspiratory lumen 220 and the right inspiratory lumen 225, respectively. Because of the separate left inspiratory gas delivery system and right inspiratory gas delivery system, the left inspiratory mixture pressurizer 924 and the right inspiratory mixture pressurizer 914 can be set to provide different pressures for inspiratory gases to the left lung 130 and right lung 135, respectively, through the left inspiratory lumen 220 and the right inspiratory lumen 225, respectively. This may be helpful if one lung is in a different state than the other lung—for example, if one lung is more diseased or injured than the other lung, if one lung is smaller or larger than the other lung, if one lung is or more or less compliant or more or less capable than the other lung, or some combination thereof. Similarly, the left gas property control 918 and the right gas property control 908 can set higher or lower humidities, temperatures, or other gas properties for inspiratory mixture supplied to one lung than the other lung. In ventilator systems with a separate left inspiratory gas supply system and a separate right inspiratory gas supply system, the left lung 130 and the right lung 135 may even be provided with slightly different inspiratory mixtures (e.g., more oxygen to one lung than the other, more carbon dioxide to one lung than the other), based on different needs of the two lungs 130-135.

For example, it may be beneficial to deliver more oxygen to a lung involved in pneumothorax, or to lung involved directly in the pneumonia process, while maintaining lower oxygen concentration in a healthier lung, to not stimulate creation of free radicals and high oxygen concentration injury and optimize shunting. In another clinical example of the unilateral left or lung pulmonary emboli or lung hemorrhage it may be useful, desired by the operator, or indicated, to provide oxygen to one lung but not the other lung.

Similarly, the separate left expiratory gas receipt system and right expiratory gas receipt system separately receive expiratory mixture from the left lung 130 and right lung 135, respectively, through the left expiratory lumen 520 and the right expiratory lumen 525, respectively. Because of the separate left expiratory gas receipt system and right expiratory gas receipt system, the left expiratory mixture pressurizer 944 and the right expiratory mixture pressurizer 954 can be set to provide different expiratory pressures to apply to the expiratory gases through the left expiratory lumen 520 and the right expiratory lumen 525, respectively. This may be helpful if one lung is in a different state than the other lung—for example, if one lung is more diseased or injured than the other lung, if one lung is smaller or larger than the other lung, if one lung is or more or less compliant or more or less capable than the other lung, or some combination thereof. In ventilator systems with a separate left expiratory gas output system and a separate right expiratory gas output system, the expiratory gases received from the left lung 130 and the expiratory gases received from the right lung 135 may even be filtered differently and/or output to different types of outputs (e.g., exhaust, sink) based on the properties of the expiratory gases and/or lungs 130-135 (e.g., based on which of the lungs 130-135 is diseased and which of the lungs 130-135 is healthy). Different clinical testing can be applied to expiratory gas evacuated from different functional or structural portions of the lung, entire lung, or both lungs to allow for localization and identification of the problem, diseases, or clinical context. Different treatments can be applied to inspiratory gas inhaled into different portions of the lung to allow for directing the treatment to a given structural or functional portion of the lung, or the entire lung.

The amount of inspiratory pressure applied by the inspiratory mixture pressurizer 914 may be set based on sensor data from the capnometer 926, the inspiratory mixture sensors 910, the inspiratory mixture sensors 920, the intratracheal sensors 934, the capnometer 938, the capnometer 948, the expiratory mixture sensors 940, the expiratory mixture sensors 950, any other sensor or a combination thereof. The amount of inspiratory pressure applied by the inspiratory mixture pressurizer 924 may be set based on sensor data from the capnometer 926, the inspiratory mixture sensors 910, the inspiratory mixture sensors 920, the intratracheal sensors 934, the capnometer 938, the capnometer 948, the expiratory mixture sensors 940, the expiratory mixture sensors 950, any other sensor or a combination thereof. The amount of expiratory pressure applied by the expiratory mixture pressurizer 944 may be set based on sensor data from the capnometer 926, the inspiratory mixture sensors 910, the inspiratory mixture sensors 920, the intratracheal sensors 934, the capnometer 938, the capnometer 948, the expiratory mixture sensors 940, the expiratory mixture sensors 950, any other sensors or a combination thereof. The amount of expiratory pressure applied by the expiratory mixture pressurizer 954 may be set based on sensor data from the capnometer 926, the inspiratory mixture sensors 910, the inspiratory mixture sensors 920, the intratracheal sensors 934, the capnometer 938, the capnometer 948, the expiratory mixture sensors 940, the expiratory mixture sensors 950, any other sensors, or a combination thereof.

In some examples, the inspiratory pressures applied by the inspiratory mixture pressurizers 914 and 924, and the expiratory pressures applied by the expiratory mixture pressurizers 944 and 954, can be set based on certain criteria. These criteria can include, for example, to match as closely as possible, breath by breath, the amount of the expiratory mixture exiting the right lung 135 through the right expiratory lumen 525 with the amount of the inspiratory mixture entering the right lung 135 through the right inspiratory lumen 225. These may be determined by matching areas of inspiratory flow and expiratory flow curves (graphed as flow/time). These criteria can include, for example, to match as closely as possible, breath by breath, the amount of the expiratory mixture exiting the left lung 130 through the left expiratory lumen 520 with the amount of the inspiratory mixture entering the left lung 130 through the left inspiratory lumen 220. These may be determined by matching areas of inspiratory flow and expiratory flow curves (graphed as flow/time). These criteria can include #maintaining positive expiratory pressure at the position of intratracheal pressure sensors 934. This would functionally separate the left lung 130 from the right lung 135, by minimizing the left-to-right and right-to-left flow between the lungs.

In some examples, the ventilator system may output a warning (e.g., through interface 175), or may automatically adjust inspiratory pressures and/or expiratory pressures, when certain thresholds are reached and/or crossed. One threshold may be if (Expiratory Mixture volume from right lung 135/Inspiratory Mixture volume to right lung 135) approaches, reaches, or crosses a certain threshold $T_1$. Another threshold may be if (Expiratory Mixture volume from left lung 130/Inspiratory Mixture volume to left lung 130) approaches, reaches, or crosses the threshold $T_1$. Another threshold may be if (Expiratory Mixture volume from right lung 135/Inspiratory Mixture volume to right lung 135) approaches, reaches, or crosses the threshold $1/T_1$. Another threshold may be if (Expiratory Mixture volume from left lung 130/Inspiratory Mixture volume to left lung 130) approaches, reaches, or crosses the threshold $1/T_1$. The value of $T_1$ may be set automatically by the controller 170 and/or by the user 190 through the interface 175. These thresholds, warnings and automatic adjustments, or any combination of thereof, may warn operator of undesired poor functional separation between the left vs. right lung, may warn operator about presence of significant leak of left-to-right or right-to-left of inspiratory gasses, and may alleviate this leak.

Another threshold may be if (Expiratory Mixture volume from right lung 135—Inspiratory Mixture volume to right lung 135) approaches, reaches, or crosses a certain threshold $T_2$. Another threshold may be if (Expiratory Mixture volume from left lung 130—Inspiratory Mixture volume to left lung 130) approaches, reaches, or crosses the threshold $T_2$. Another threshold may be if (Expiratory Mixture volume from right lung 135—Inspiratory Mixture volume to right lung 135) approaches, reaches, or crosses the threshold $1/T_2$. Another threshold may be if (Expiratory Mixture volume from left lung 130—Inspiratory Mixture volume to left lung 130) approaches, reaches, or crosses the threshold $1/T_2$. The value of $T_2$ may be set automatically by the controller 170 and/or by the user 190 through the interface 175. These thresholds, and based on them warnings and automatic adjustments, or any combination of thereof, may warn operator of undesired poor functional separation between the left vs. right lung, may warn operator about presence of significant leak of left-to-right or right-to-left of inspiratory gasses, and may alleviate this leak.

Another threshold may be if (Expiratory Mixture volume from right lung 135) approaches, reaches, or crosses a certain threshold $T_3$. Another threshold may be if (Expiratory Mixture volume from right lung 135) approaches, reaches, or crosses the threshold $T_3$. Another threshold may be if (Expiratory Mixture volume from right lung 135) approaches, reaches, or crosses the threshold $1/T_3$. Another threshold may be if (Expiratory Mixture volume from left lung 130) approaches, reaches, or crosses the threshold $1/T_3$. Another threshold may be if (Inspiratory Mixture volume to right lung 135) approaches, reaches, or crosses the threshold $T_3$. Another threshold may be if (Inspiratory Mixture volume to right lung 135) approaches, reaches, or crosses the threshold $T_3$. Another threshold may be if (Inspiratory Mixture volume to right lung 135) approaches, reaches, or crosses the threshold $1/T_3$. Another threshold may be if (Inspiratory Mixture volume to left lung 130) approaches, reaches, or crosses the threshold $1/T_3$. The value of $T_3$ may be set automatically by the controller 170 and/or by the user 190 through the interface 175. # These thresholds, and based on them warnings and automatic adjustments, or any combination of thereof, may warn operator of undesired poor functional separation between the left vs. right lung, may warn operator about presence of significant leak of left-to-right or right-to-left of inspiratory gasses, and may alleviate this leak.

Detection that any of the thresholds above are approached, reached, or crossed may automatically cause, or may cause users 190 to perform, change to a different mode of ventilation, PEEP adjustments, use of different size(s) of endotracheal tube, use of different size(s) of inspiratory lumen(s), use of different size(s) of expiratory lumen(s), changes to the positioning of patient, or a combination thereof.

In an illustrative example, a patient 105's left lung 130 may be more diseased and have lower compliance than the patient 105's right lung 135. If inspiratory pressures and/or expiratory pressures are set identically for the left lung 130 and right lung 135, the controller 170 may detect that there is more Gas "Expired" by the "more compliant side" (in this case the right side) even though the same amount of Gas was "inspired" by both sides due to same applied pressure. The controller 170 can determine this mismatch as a sign of poor functional separation between the lungs and can first attempt to neutralize it by applying higher end expiratory pressure to the right expiratory lumen 525 and lower end expiratory pressure to the left expiratory lumen 520. This should decrease or eliminate the mismatch and improve functional separation between the left and right lung. The controller 170 can monitor the pressure at intratracheal pressure sensors 934 to make sure this matches an expected value (for example preset PEEP pressure) or range (e.g., at a preset programmed by the user 190). If the intratracheal pressure sensors 934 is lower than the expected value or range, the controller 170 can increase both pressures provided by right expiratory mixture pressurizer 954 for right lung 135 and left expiratory mixture pressurizer 944 for left lung 135, maintaining the earlier established pressure difference between pressures provided by right expiratory mixture pressurizer 954 (end expiratory pressure for the right expiratory mixture pressurizer 954) for right lung 135 and left expiratory mixture pressurizer 944 (end expiratory pressure for the right expiratory mixture pressurizer 944) for left lung to functionally separate left and right lung.

If the pressure detected the intratracheal sensors 934 is above the expected pressure (for example preset PEEP), the controller 170 can decrease both (for example end expiratory pressures) provided by right expiratory mixture pressurizer 954 for right lung 135 and left expiratory mixture pressurizer 944 for left lung 135, maintaining the earlier established pressure difference between pressures provided by right expiratory mixture pressurizer 954 for right lung 135 and left expiratory mixture pressurizer 944 for left lung to functionally separate left and right lung.

If the controller 170 cannot eliminate the mismatch as discussed above, and the criteria for an alarm or warning triggers, and the user 190 (e.g., a health care provider), may decide to change a position of the patient 105, for example by putting the patient 105 on his/her right side, to decrease compliance of the right lung 135.

In some examples, negative or lower than PEEP pressures may need to be applied to expiratory lumen(s) (e.g., expiratory lumen 510 of FIG. 9A, and/or expiratory lumens 520 and 525 of FIG. 9B) by the expiratory mixture pressurizer (994 and/or 954) to overcome the flow resistance in expiratory lumen(s) as the expiratory mixture(s) is/are leaving the lungs via airways and via expiratory lumen(s). Such negative or lower than PEEP pressure will allow for efficient expiratory mixture(s) evacuation from lungs 130-135 via the expiratory lumen(s). It may be useful to maintain required shorter length of the expiratory phase, as it may be useful to maintain higher respiratory rates that are pre-determined, recommended, and/or preset by an operator, and/or to prevent a phenomena referred to as "auto-PEEPing."

Pressure data from pressure sensors and/or transducer(s) (e.g., of the inspiratory mixture sensors 910, the inspiratory mixture sensors 920, the intratracheal sensors 934, the expiratory mixture sensors 940, and/or the expiratory mixture sensors 950) can be used to maintain a desired (e.g., selected by operator) level of PEEP. Similarly, pressure data can also be used to trigger alarms in case of high pressures (e.g., exceeding a threshold) or low pressures (e.g., less than a threshold). The readings from various sensors (e.g., capnometer 926, the inspiratory mixture sensors 910, the inspiratory mixture sensors 920, the intratracheal sensors 934, the capnometer 938, the capnometer 948, the expiratory mixture sensors 940, the expiratory mixture sensors 950, or a combination thereof), which may include pressure sensor(s), pressure transducer(s), temperature sensor(s), and/or capnometer(s), can be used to calculate the inspiratory mixture(s) flow rate(s) (which depend on pressures applied by inspiratory mixture pressurizer(s) 914/924) and expiratory mixture(s) flow rate(s) (which depend on pressures applied by expiratory mixture Pressurizer(s) 944/954) to maintain functional separation of the portions of the lungs.

Functional separation of the left lung 130 from the right lung 135 may be beneficial, in many clinical scenarios to prevent DCAs 425 from freely crossing between the left lung 130 from the right lung 135. For example, if patient has COVID-19 caused pneumonia in the left lung 130, it may be desired to functionally separate the left lung 130 from the right lung 135 to prevent DCAs 435 (e.g., COVID-19 virions) from moving from left lung 130 from the right lung 135.

The ventilator system pictured on FIG. 9B allows one or more operators (e.g., users 190) to functionally separate the left lung 130 from the right lung 135, by assuring that all (most) of the inspiratory mixture entering the left lung 130 via left inspiratory lumen 220 exits from the left lung 130 by the left expiratory lumen 520, and as little as possible of this inspiratory mixture exits through the right expiratory lumen 525 or enters right main bronchus 215 or right lung 135. Likewise, the ventilator system can assure that all (most) of the inspiratory mixture entering the right lung 135 via right inspiratory lumen 225 exits from the right lung 135 by the right expiratory lumen 525, and as little as possible of this inspiratory mixture exits through the left expiratory lumen 520 or enters the left main bronchus 210 or left lung 130. In many clinical scenarios, the compliance of left lung 130 and right lung 135 differ. Thus, it can be useful to provide different pressures for the left inspiratory mixture pressurizer 924 and the right inspiratory mixture pressurizer 914, it can be useful to provide different pressures for the left expiratory mixture pressurizer 944 and the right inspiratory mixture pressurizer 954, to strengthen and maintain the functional separation between the left lung 130 and the right lung 135.

In order to preserve functional separation between the left lung 130 and right lung 135, if indicated, the controller 170 can perform a real-time analysis of sensor data from various sensors (e.g., capnometer 926, the inspiratory mixture sensors 910, the inspiratory mixture sensors 920, the intratracheal sensors 934, the capnometer 938, the capnometer 948, the expiratory mixture sensors 940, the expiratory mixture sensors 950, or a combination thereof). The controller 170 can test the compliance of the left lung 130 and right lung 135 by applying various inspiratory pressures, expiratory pressures, $CO_2$ concentrations, temperatures, inspiratory mixture flow rates, and/or expiratory mixture flow rates.

In some examples, the controller 170 may detects that, even though same pressure is provided by the inspiratory pressurizers 914 and 924, different expiratory pressures may be used or detected. In an illustrative example, during each breath, 500 cc of inspiratory mixture is provided via right inspiratory lumen 225, 430 cc is received via right expiratory lumen 525, 530 cc of inspiratory mixture is provided via left inspiratory lumen 220, and 600 cc is received via left expiratory lumen 520. In this example, the controller 170 may determine that there is insufficient functional separation between the right lung 135 and the left lung 130, and will attempt to correct this in at least one of several ways. The controller 170 can increase the negative pressure (e.g., increase absolute value of the negative pressure) applied to the right expiratory lumen 525 to increase expiratory flow rate through it the right expiratory lumen 525, decrease the pressure applied to right inspiratory lumen 225 to increase inspiratory flow rate through the right inspiratory lumen 225, or a combination thereof.

If the controller 170 can't find a solution to resolve inadequate functional separation of the left lung 130 and the right lung 135 (or portions thereof) based on pressure, or if capnometer sensor data is more reliable or readily available, then the controller 170 can base its actions on capnometer data from capnometers (e.g., capnometers 926, 934, 938, and/or 948). The controller 170 can, increase, for a brief period, the $CO_2$ concentration of the inspiratory mixture to the right lung 135 and measure a time elapsed until a peak $CO_2$ concentration is detected corresponding to the $CO_2$ concentration increase. The intratracheal sensors 934 may include a capnometer, which may be useful for this purpose. If the time to detected $CO_2$ partial pressure peak is long (e.g., longer than a threshold) and peak is low (e.g., lower than a threshold), the controller 170 may determine that there is little (e.g., less than a threshold) inspiratory mixture crossing from the right lung 135 to the left lung 130. If the time to detected $CO_2$ partial pressure peak is short (e.g., shorter than a threshold), and peak is high (e.g., higher than a threshold), the controller 170 may determine that there is a lot of (e.g., more than a threshold) inspiratory mixture crossing from the right lung 135 to the left lung 130.

The controller 170 can then repeat by the attempt by increasing, for a brief period, the $CO_2$ concentration of the inspiratory mixture to the left lung 130 and measure the time elapsed until peak $CO_2$ is detected by the capnometers. If the time to detected $CO_2$ partial pressure peak is long (e.g., longer than a threshold) and peak is low (e.g., lower than a threshold), the controller 170 may determine that there is little (e.g., less than a threshold) inspiratory mixture crossing from the left lung 130 to the right lung 135. If the time to detected $CO_2$ partial pressure peak is short (e.g., shorter than a threshold), and peak is high (e.g., higher than a threshold), the controller 170 may determine that there is a lot of (e.g., more than a threshold) inspiratory mixture crossing from the left lung 130 to the right lung 135.

The controller 170 can further try to adjust the pressures of inspiratory pressurizers 914/924 and the expiratory pressurizers 944/954 to maintain minimal peak and longest possible time to peak.

Instead of increasing $CO_2$ in the inspiratory mixture(s) and detecting the peak in $CO_2$ at the capnometer(s) corresponding to the increase in $CO_2$, the controller 170 may instead decrease $CO_2$ in the inspiratory mixture(s) and detect a corresponding dip in the peak in $CO_2$ at the capnometer(s).

Instead of increasing $CO_2$ in the inspiratory mixture(s) and detecting the peak in $CO_2$ at the capnometer(s) corresponding to the increase in $CO_2$, the controller 170 may instead increase or decrease temperature of the inspiratory mixture(s) and detect a corresponding peak or dip in temperature at one or more thermometers, such as a thermometer of the intratracheal sensors 934.

The intratracheal pressure sensor 934, may be used to warn the operator of flow issues, within the inspiratory and expiratory lumen, for example due to mucus plugging. In such scenarios, the gradient of the pressure between the inspiratory or expiratory pressurizers vs. intratracheal sensors would be out of proportion higher than baseline gradient, recorded earlier during normal operation. This can be sensed by sensor and software and can trigger warning similarly to warning described earlier.

The intratracheal pressure sensor 934 can allow to accurate titration of PEEP exactly in position, where it really should be measured. This would provide most accurately PEEP, regardless of biases caused by example of flow and resistance via inspiratory or expiratory lumens.

In some examples, the inspiratory flow control system 150 of FIG. 1 may include at least a subset of the inspiratory gas supply system and/or at least a subset of the inspiratory gas delivery systems of FIG. 9A. In some examples, the inspiratory gas source(s) 160 of FIG. 1 may include at least a subset of the inspiratory gas supply system and/or at least a subset of the inspiratory gas delivery systems of FIG. 9A. In some examples, the expiratory flow control system 155 of FIG. 1 may include at least a subset of the expiratory gas receipt systems and/or at least a subset of the expiratory gas removal system of FIG. 9A. In some examples, the expiratory output(s) 165 of FIG. 1 may include at least a subset of the expiratory gas receipt systems and/or at least a subset of the expiratory gas removal system of FIG. 9A.

Figure 10:
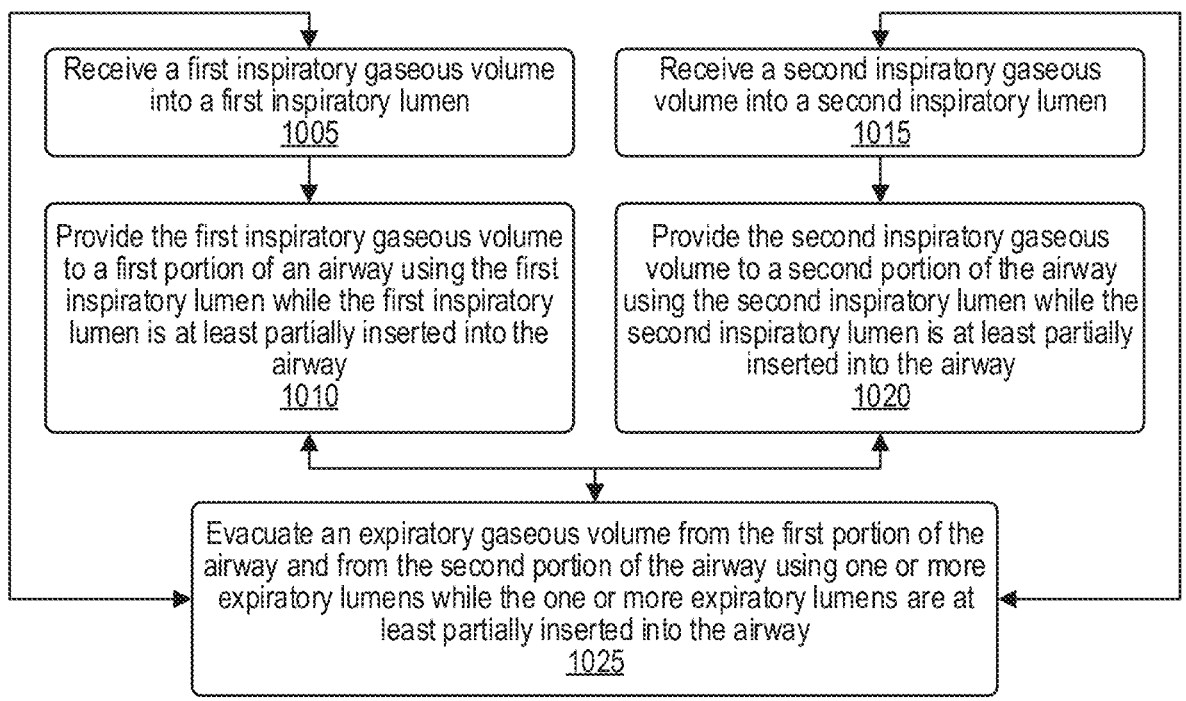
FIG. 10 is a flow diagram illustrating exemplary operations for airflow control.

FIG. 10 is a flow diagram illustrating exemplary operations 1000 for airflow control. The operations 1000 may be performed by a ventilator system. The ventilator system that performs the operations 1000 may include the ventilator systems of FIG. 1, the ventilator system of FIG. 2, the ventilator system of FIG. 4A, the ventilator system of FIG. 4B, the ventilator system of FIG. 4C, the ventilator system of FIG. 5A, the ventilator system of FIG. 5B, the ventilator system of FIG. 5C, the ventilator system of FIG. 6, the ETT 120 of FIG. 7A, a ventilator system providing pressure changes 850, a ventilator system providing inspiratory flow 830A, a ventilator system providing inspiratory flow 830B, a ventilator system providing inspiratory flow 830C, a ventilator system providing inspiratory flow 830D, a ventilator system providing inspiratory flow 830E, a ventilator system providing expiratory flow 835A, a ventilator system providing expiratory flow 835B, a ventilator system providing expiratory flow 835C, a ventilator system providing expiratory flow 835D, a ventilator system providing expiratory flow 835E, the ventilator system of FIG. 9A, the a ventilator system of FIG. 9B, one or more components of any of the previously-listed ventilator systems or elements, or a combination thereof.

At operation 1005, the ventilator system receives a first inspiratory gaseous volume into a first inspiratory lumen. At operation 1010, the ventilator system provides the first inspiratory gaseous volume to a first portion of an airway (e.g., of a patient 105) using the first inspiratory lumen while the first inspiratory lumen is at least partially inserted into the airway.

At operation 1015, the ventilator system receives a second inspiratory gaseous volume into a second inspiratory lumen. At operation 1020, the ventilator system provides the second inspiratory gaseous volume to a second portion of the airway using the second inspiratory lumen while the second inspiratory lumen is at least partially inserted into the airway. In some examples, the ventilator system can provide the first inspiratory gaseous volume to the first portion of the airway using the first inspiratory lumen (as in operation 1010) contemporaneously with providing the second inspiratory gaseous volume to the second portion of the airway using the second inspiratory lumen (as in operation 1020).

According to a first illustrative embodiment of operations 1005-1020, examples of the first inspiratory lumen of operations 1005 and 1010 may include the left inspiratory lumen 220 of FIGS. 5A-5C, 6, 7A, 9A, and 9B. According to the first illustrative embodiment of operations 1005-1020, examples of the first portion of the airway of operations 1005 and 1010 include the left lung 130, the left primary bronchus 210, one or more left secondary bronchi 310, one or more tertiary bronchi in the left lung 130, one or more 4th order bronchi in the left lung 130, one or more 5th order bronchi in the left lung 130, one or more 6th order bronchi in the left lung 130, one or more bronchioles 320 in the left lung 130, one or more alveoli 325 in the left lung 130, a left portion of the trachea 115, or a combination thereof.

According to the first illustrative embodiment of operations 1005-1020, examples of the second inspiratory lumen of operations 1015 and 1020 may include the right inspiratory lumen 225 of FIGS. 5A-5C, 6, 7A, 9A, and 9B. According to the first illustrative embodiment of operations 1005-1020, examples of the second portion of the airway of operations 1015 and 1020 include the right lung 135, the right primary bronchus 215, one or more right secondary bronchi 315, one or more tertiary bronchi in the right lung 135, one or more 4th order bronchi in the right lung 135, one or more 5th order bronchi in the right lung 135, one or more 6th order bronchi in the right lung 135, one or more bronchioles 320 in the right lung 135, one or more alveoli 325 in the right lung 135, a right portion of the trachea 115, or a combination thereof.

According to a second illustrative embodiment of operations 1005-1020, examples of the first inspiratory lumen of operations 1005 and 1010 may include the right inspiratory lumen 225 of FIGS. 5A-5C, 6, 7A, 9A, and 9B. According to the second illustrative embodiment of operations 1005-1020, examples of the second portion of the airway of operations 1005 and 1010 include the right lung 135, the right primary bronchus 215, one or more right secondary bronchi 315, one or more tertiary bronchi in the right lung 135, one or more 4th order bronchi in the right lung 135, one or more 5th order bronchi in the right lung 135, one or more 6th order bronchi in the right lung 135, one or more bronchioles 320 in the right lung 135, one or more alveoli 325 in the right lung 135, a right portion of the trachea 115, or a combination thereof.

According to the second illustrative embodiment of operations 1005-1020, examples of the second inspiratory lumen of operations 1015 and 1020 may include the left inspiratory lumen 220 of FIGS. 5A-5C, 6, 7A, 9A, and 9B. According to the second illustrative embodiment of operations 1005-1020, examples of the second portion of the airway of operations 1015 and 1020 include the left lung 130, the left primary bronchus 210, one or more left secondary bronchi 310, one or more tertiary bronchi in the left lung 130, one or more 4th order bronchi in the left lung 130, one or more 5th order bronchi in the left lung 130, one or more 6th order bronchi in the left lung 130, one or more bronchioles 320 in the left lung 130, one or more alveoli 325 in the left lung 130, a left portion of the trachea 115, or a combination thereof.

At operation 1025, the ventilator system evacuates an expiratory gaseous volume from the first portion of the airway and from the second portion of the airway using one or more expiratory lumens while the one or more expiratory lumens are at least partially inserted into the airway. In some examples, the ventilator system can evacuate the expiratory gaseous volume from the first portion of the airway and from the second portion of the airway using the one or more expiratory lumens (as in operation 1025) contemporaneously with providing the first inspiratory gaseous volume to the first portion of the airway using the first inspiratory lumen (as in operation 1010) and/or with providing the second inspiratory gaseous volume to the second portion of the airway using the second inspiratory lumen (as in operation 1020).

Examples of the one or more expiratory lumens of operation 1025 can include the expiratory lumen 510 of FIGS. 5A-5B, the expiratory lumen 510 of FIG. 6, the expiratory lumen 510 of FIG. 7A, the expiratory lumen 510 of FIG. 9A, the left expiratory lumen 520 of FIG. 5C, the left expiratory lumen 520 of FIG. 9A, the left expiratory lumen 520 of FIG. 9B, the right expiratory lumen 525 of FIG. 5C, the right expiratory lumen 525 of FIG. 9A, the right expiratory lumen 525 of FIG. 9B, or a combination thereof.

In some examples, the first portion of the airway includes a first lung, and the second portion of the airway includes a second lung distinct from the first lung. For instance, according to the first illustrative embodiment of operations 1005-1020, the first lung may be the left lung 130, and the second lung may be the right lung 135. According to the second illustrative embodiment of operations 1005-1020, the first lung may be the right lung 135, and the second lung may be the left lung 130.

In some examples, the first inspiratory lumen is configured to provide the first inspiratory gaseous volume to a first lobe of the first lung, and the one or more expiratory lumens are configured to evacuate the expiratory gaseous volume from a second lobe of the first lung. In some cases, the ventilator systems of FIGS. 5A-5D may be used to provide this difference in lobe for inspiratory air provision versus expiratory air evacuation. The first lobe is different than the second lobe. For instance, if the first lobe is a superior lobe, then the second lobe can be a middle lobe or an inferior lobe, and vice versa. If the first lobe is a middle lobe, then the second lobe can be a superior lobe or an inferior lobe, or vice versa. If the first lobe is an inferior lobe, then the second lobe can be a superior lobe or a middle lobe, or vice versa.

In some examples, the second inspiratory lumen is configured to provide the second inspiratory gaseous volume to a first lobe of the second lung, and the one or more expiratory lumens are configured to evacuate the expiratory gaseous volume from a second lobe of the second lung. In some cases, the ventilator systems of FIGS. 5A-5D may be used to provide this difference in lobe for inspiratory air provision versus expiratory air evacuation. The first lobe is different than the second lobe. For instance, if the first lobe is a superior lobe, then the second lobe can be a middle lobe or an inferior lobe, and vice versa. If the first lobe is a middle lobe, then the second lobe can be a superior lobe or an inferior lobe, or vice versa. If the first lobe is an inferior lobe, then the second lobe can be a superior lobe or a middle lobe, or vice versa.

In some examples, the first portion of the airway includes a first lobe of the first lung, and the second portion of the airway includes a second lobe of the second lung. The first lobe can be different than the second lobe. For instance, if the first lobe is a superior lobe, then the second lobe can be a middle lobe or an inferior lobe, and vice versa. If the first lobe is a middle lobe, then the second lobe can be a superior lobe or an inferior lobe, or vice versa. If the first lobe is an inferior lobe, then the second lobe can be a superior lobe or a middle lobe, or vice versa. In some cases, the ventilator systems of FIGS. 5A-5D may be used to provide this difference in lobe based on lung.

In some examples, the first portion of the airway includes a first bronchus, and the second portion of the airway includes a second bronchus distinct from the first bronchus. The first and second bronchi may each (or both) be primary, secondary, tertiary, 4th order, 5th order, or 6th order bronchi. For instance, according to the first illustrative embodiment of operations 1005-1020, the first bronchus may be a bronchus in the left lung 130, and the second bronchus may be a bronchus in the right lung 135. According to the second illustrative embodiment of operations 1005-1020, the first bronchus may be a bronchus in the right lung 135, and the second bronchus may be a bronchus in the left lung 130.

In some examples, the first inspiratory lumen receives the first inspiratory gaseous volume from a first gas source, and second inspiratory lumen receives the second inspiratory gaseous volume from the first gas source. In some examples, the first inspiratory lumen receives the first inspiratory gaseous volume from a first gas source, and wherein second inspiratory lumen receives the second inspiratory gaseous volume from a second gas source. The first gas source can include, for example, the inspiratory gas source(s) 160 of FIG. 1, the inspiratory flow control system(s) 150 of FIG. 1, the inspiratory tube(s) 152 of FIG. 1, the inspiratory gas supply system of FIG. 9A, the inspiratory gas supply system(s) of FIG. 9B, the inspiratory gas delivery system of FIG. 9A, the inspiratory gas delivery system(s) of FIG. 9B, one or more components of one of the previously listed elements, or a combination thereof. The second gas source can include, for example, the inspiratory gas source(s) 160 of FIG. 1, the inspiratory flow control system(s) 150 of FIG. 1, the inspiratory tube(s) 152 of FIG. 1, the inspiratory gas supply system of FIG. 9A, the inspiratory gas supply system(s) of FIG. 9B, the inspiratory gas delivery system of FIG. 9A, the inspiratory gas delivery system(s) of FIG. 9B, one or more components of one of the previously listed elements, or a combination thereof.

In some examples, the first inspiratory gaseous volume and the second inspiratory gaseous volume both include an inspiratory mixture of a plurality of gases that are mixed according to one or more predetermined ratios. The plurality of gases may be stored and provided for mixing by the inspiratory gas source(s) 160 and/or the gas sources 932. The plurality of gases may be mixed to form the inspiratory mixture by the inspiratory flow control system(s) 150 and/or the gas mixer 930. In some examples, the inspiratory mixture may include at least one of oxygen ($O_2$), carbon dioxide ($CO_2$), nitrogen (N), argon (Ar), one or more drugs (in gaseous and/or aerosolized form), one or more one or more other elemental gases, one or more other molecular gases, a pre-mixed atmospheric gas source, or a combination thereof.

In some examples, the ventilator system can include an endotracheal tube 120. The endotracheal tube can include at least the first inspiratory lumen, the second inspiratory lumen, and the expiratory lumen. Examples of arrangements of the first inspiratory lumen, the second inspiratory lumen, and the expiratory lumen in the ETT 120 are illustrated in FIGS. 5A, 5B, 5C, 6, 7A, and 7B.

In some examples, the first inspiratory lumen passes through the endotracheal tube and extends beyond a tip of the endotracheal tube toward the first portion of the airway, wherein the second inspiratory lumen passes through the endotracheal tube and extends beyond the tip of the endotracheal tube toward the second portion of the airway.

In some examples, the tip 125 of the endotracheal tube 120 includes the tip of the expiratory lumen of operation 1025. For example, the expiratory lumen 510 of FIGS. 5A, 5B, and/or 6 may be examples of the expiratory lumen of operation 1025 where the tip of the expiratory lumen is the tip 125 of the endotracheal tube 120.

In some examples, the ventilator system includes one or more inspiratory flow control mechanisms that control flow of the first inspiratory gaseous volume to the first portion of the airway through the first inspiratory lumen and that control flow of second inspiratory gaseous volume to the second portion of the airway through the second inspiratory lumen. Examples of the one or more inspiratory flow control mechanisms can include, for instance, the inspiratory gas source(s) 160 of FIG. 1, the inspiratory flow control system(s) 150 of FIG. 1, the inspiratory tube(s) 152 of FIG. 1, the inspiratory gas supply system of FIG. 9A, the inspiratory gas supply system(s) of FIG. 9B, the inspiratory gas delivery system of FIG. 9A, the inspiratory gas delivery system(s) of FIG. 9B, the pressurizer(s) 145, the controllers 170, one or more components of one of the previously listed elements, or a combination thereof.

In some examples, the one or more expiratory lumens include a first expiratory lumen configured to evacuate a first expiratory gaseous volume from the first portion of the airway and a second expiratory lumen configured to evacuate a second expiratory gaseous volume from the second portion of the airway. In some examples, the first expiratory lumen passes through the endotracheal tube and extends beyond a tip of the endotracheal tube toward the first portion of the airway. In some examples, the second expiratory lumen passes through the endotracheal tube and extends beyond the tip of the endotracheal tube toward the second portion of the airway. Examples of the first expiratory lumen include the left expiratory lumen 520 and the right expiratory lumen 525. Examples of the second expiratory lumen include the left expiratory lumen 520 and the right expiratory lumen 525.

In some examples, a first expiratory mixture pressurizer provides suction to evacuate the first expiratory gaseous volume from the first portion of the airway through the first expiratory lumen. In some examples, a second expiratory mixture pressurizer that provides suction to evacuate the second expiratory gaseous volume from the second portion of the airway through the second expiratory lumen. Examples of the first expiratory mixture pressurizer include the expiratory mixture pressurizer 944 and the expiratory mixture pressurizer 954. Examples of the second expiratory mixture pressurizer include the expiratory mixture pressurizer 944 and the expiratory mixture pressurizer 954.

In some examples, the one or more expiratory lumens of the ventilator system also include a third expiratory lumen configured to evacuate a third expiratory gaseous volume from a third portion of the airway. In some examples, the third expiratory lumen may branch off of the first expiratory lumen or the second expiratory lumen. In some examples, the third portion of the airway may include, for example, one or more bronchi that the third expiratory lumen evacuates more expiratory gas from than the first expiratory lumen and/or the second expiratory lumen do.

In some examples, the ventilator system includes one or more expiratory flow control mechanisms that control flow of the expiratory gaseous volume from the first portion of the airway and from the second portion of the airway to an expiratory air output through the one or more expiratory lumens. Examples of the one or more expiratory flow control mechanisms can include, for instance, the expiratory gas output(s) 165 of FIG. 1, the expiratory flow control system(s) 155 of FIG. 1, the expiratory tube(s) 157 of FIG. 1, the expiratory gas receipt system of FIG. 9A, the expiratory gas receipt system(s) of FIG. 9B, the expiratory gas removal system of FIG. 9A, the expiratory gas removal system(s) of FIG. 9B, the pressurizer(s) 145, the controllers 170, one or more components of one of the previously listed elements, or a combination thereof. #

In some examples, the ventilator system includes one or more inspiratory flow control mechanisms that provide the first inspiratory gaseous volume to the first inspiratory lumen and that provide the second inspiratory gaseous volume to the second inspiratory lumen. Examples of the one or more inspiratory flow control mechanisms can include, for instance, the inspiratory flow control system(s) 150, the inspiratory gas source(s) 160, the inspiratory gas provision system 490, the gas sources 932, the gas mixer(s) 930, the gas property control(s) 928, the capnometer(s) 926, the inspiratory mixture pressurizer 914, the buffer 912, the inspiratory mixture sensors 910, the gas property control 908, the pressure release valve 906, the inspiratory mixture pressurizer 924, the buffer 922, the inspiratory mixture sensors 920, the gas property control 918, the pressure release valve 916, or a combination thereof.

In some examples, the ventilator system includes a controller. The controller can include, for example, a memory storing instructions, and a processor that executes the instructions. Examples of the controller include the controller 170 and/or the controller 480. Execution of the instructions can cause the processor to maintain net inspiratory flow at a first level during a first portion of each of a plurality of respiratory cycles. Net inspiratory flow corresponds to provision of both the first inspiratory gaseous volume and the second inspiratory gaseous volume. Examples of net inspiratory flow include inspiratory flows 830A-830E. Execution of the instructions can cause the processor to maintain net expiratory flow at a second level during the first portion of each of the plurality of respiratory cycles, wherein net expiratory flow corresponds to provision of pressurized suction to control flow of the expiratory gaseous volume. Examples of net expiratory flow include expiratory flows 835A-835E.

In some examples, the first portion of each of the plurality of respiratory cycles is an inspiration (e.g., time zero (0) to time $t_A$ or time $t_D$ to time $t_E$), and an absolute value of the net inspiratory flow is greater than an absolute value of the net expiratory flow. In some examples, the first portion of each of the plurality of respiratory cycles is an expiration (e.g., time $t_B$ to time $t_D$ or time $t_F$ to time $t_H$), and an absolute value of the net inspiratory flow is less than an absolute value of the net expiratory flow. In some examples, the first portion of each of the plurality of respiratory cycles is an hold (e.g., inspiratory hold, expiratory hold, or pause) (e.g., time $t_A$ to time $t_B$ or time $t_E$ to time $t_F$), and wherein an absolute value of the net inspiratory flow is equal to an absolute value of the net expiratory flow.

In some examples, the ventilator system includes an intratracheal sensor that measures an intratracheal pressure in a trachea of the patient. An example of the intratracheal sensor includes the intratracheal sensors 934. In some examples, the ventilator system includes one or more pressurizers. The one or more pressurizers are configured to provide airflow pressure based on the intratracheal pressure measured by the intratracheal sensor. The airflow pressure includes at least one of a first inspiratory pressure to provide the first inspiratory gaseous volume to the first portion of the airway via the first inspiratory lumen, a second inspiratory pressure to provide the second inspiratory gaseous volume to the second portion of the airway via the second inspiratory lumen, an expiratory pressure to evacuate the expiratory gaseous volume from at least one of the first portion of the airway and the second portion of the airway via the one or more expiratory lumens, or a combination thereof. The one or more pressurizers may include, for example, the pressurizers 145, the inspiratory mixture pressurizer 914, the inspiratory mixture pressurizer 924, the expiratory mixture pressurizer 944, the expiratory mixture pressurizer 954, or a combination thereof.

In some examples, the ventilator system includes one or more markers along at least one of the first inspiratory lumen, the second inspiratory lumen, the one or more expiratory lumens, or a combination thereof. The one or more markers can be radiopaque, radioactive, emissive of a magnetic field, emissive of one or more electromagnetic signals, or some combination thereof. The one or more markers can thus be used to locate the first inspiratory lumen, the second inspiratory lumen, and/or the one or more expiratory lumens within the patient 105's body, for example via a scan and/or via triangulation, to determine whether the lumens are positioned correctly in the patient 105's body (e.g., in the first portion of the airway, in the second portion of the airway, etc.).

In some examples, the ventilator system includes a third inspiratory lumen that is configured to receive a third inspiratory gaseous volume and to provide the third inspiratory gaseous volume to a third portion of the airway while the third inspiratory lumen is at least partially inserted into the airway. In some examples, the third inspiratory lumen may branch off of the first inspiratory lumen or the second inspiratory lumen. In some examples, the third portion of the airway may include, for example, one or more bronchi that the third inspiratory lumen provides more inspiratory gas to than the first inspiratory lumen and/or the second inspiratory lumen do.

In some examples, the ventilator system includes a microfilter adapter that includes a microfilter medium and one or more one-way airflow valves. The microfilter adapter passes airflow through the one or more one-way airflow valves and filters the airflow through the microfilter medium. The airflow includes at least one of the first inspiratory gaseous volume, the second inspiratory gaseous volume, and the expiratory gaseous volume. Examples of the microfilter adapter include the microfilter adapter 460. Examples of the microfilter medium include the microfilter medium 465. The microfilter adapter can be positioned in the ventilator system similarly to the adapter 450 and/or the adapter 455. In some examples, the ventilator system includes another type of adapter in addition to or instead of the microfilter adapter, such as the connector 610, which may provide the first inspiratory lumen and the second inspiratory lumen. In some examples, the ventilator system includes another type of adapter in addition to or instead of the microfilter adapter, such as the airflow rerouting adapter 470.

Figure 11:
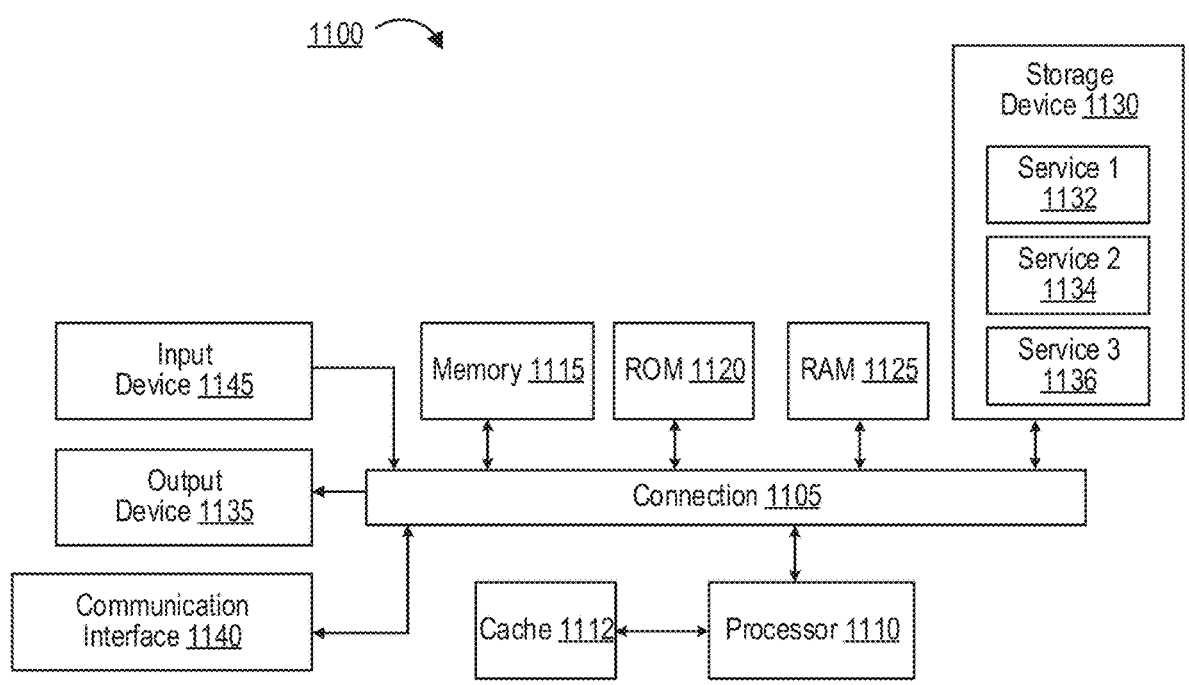
FIG. 11 is a block diagram of an exemplary computing device that may be used to implement some aspects of the technology.

FIG. 11 illustrates an exemplary computing system 1100 that may be used to implement some aspects of the technology. For example, any of the computing devices, computing systems, network devices, network systems, servers, and/or arrangements of circuitry described herein may include at least one computing system 1100, or may include at least one component of the computer system 1100 identified in FIG. 11. The computing system 1100 of FIG. 11 includes one or more processors 1110 and memory units 1120. Each of the processor(s) 1110 may refer to one or more processors, controllers, microcontrollers, central processing units (CPUs), graphics processing units (GPUs), arithmetic logic units (ALUs), accelerated processing units (APUs), digital signal processors (DSPs), application specific integrated circuits (ASICs), field-programmable gate arrays (FPGAs), or combinations thereof. Each of the processor(s) 1110 may include one or more cores, either integrated onto a single chip or spread across multiple chips connected or coupled together. Memory 1120 stores, in part, instructions and data for execution by processor 1110. Memory 1120 can store the executable code when in operation. The system 1100 of FIG. 11 further includes a mass storage device 1130, portable storage medium drive(s) 1140, output devices 1150, user input devices 1160, a graphics display 1170, and peripheral devices 1180.

The components shown in FIG. 11 are depicted as being connected via a single bus 1190. However, the components may be connected through one or more data transport means. For example, processor unit 1110 and memory 1120 may be connected via a local microprocessor bus, and the mass storage device 1130, peripheral device(s) 1180, portable storage device 1140, and display system 1170 may be connected via one or more input/output (I/O) buses.

Mass storage device 1130, which may be implemented with a magnetic disk drive or an optical disk drive, is a non-volatile storage device for storing data and instructions for use by processor unit 1110. Mass storage device 1130 can store the system software for implementing some aspects of the subject technology for purposes of loading that software into memory 1120.

Portable storage device 1140 operates in conjunction with a portable non-volatile storage medium, such as a floppy disk, compact disk or Digital video disc, to input and output data and code to and from the computer system 1100 of FIG. 11. The system software for implementing aspects of the subject technology may be stored on such a portable medium and input to the computer system 1100 via the portable storage device 1140.

The memory 1120, mass storage device 1130, or portable storage 1140 may in some cases store sensitive information, such as transaction information, health information, or cryptographic keys, and may in some cases encrypt or decrypt such information with the aid of the processor 1110. The memory 1120, mass storage device 1130, or portable storage 1140 may in some cases store, at least in part, instructions, executable code, or other data for execution or processing by the processor 1110.

Output devices 1150 may include, for example, communication circuitry for outputting data through wired or wireless means, display circuitry for displaying data via a display screen, audio circuitry for outputting audio via headphones or a speaker, printer circuitry for printing data via a printer, or some combination thereof. The display screen may be any type of display discussed with respect to the display system 1170. The printer may be inkjet, laserjet, thermal, or some combination thereof. In some cases, the output device circuitry 1150 may allow for transmission of data over an audio jack/plug, a microphone jack/plug, a universal serial bus (USB) port/plug, an Apple® Lightning® port/plug, an Ethernet port/plug, a fiber optic port/plug, a proprietary wired port/plug, a BLUETOOTH® wireless signal transfer, a BLUETOOTH® low energy (BLE) wireless signal transfer, an IBEACON® wireless signal transfer, a radio-frequency identification (RFID) wireless signal transfer, near-field communications (NFC) wireless signal transfer, dedicated short range communication (DSRC) wireless signal transfer, 802.11 Wi-Fi wireless signal transfer, wireless local area network (WLAN) signal transfer, Visible Light Communication (VLC), Worldwide Interoperability for Microwave Access (WiMAX), Infrared (IR) communication wireless signal transfer, Public Switched Telephone Network (PSTN) signal transfer, Integrated Services Digital Network (ISDN) signal transfer, 3G/4G/5G/LTE cellular data network wireless signal transfer, ad-hoc network signal transfer, radio wave signal transfer, microwave signal transfer, infrared signal transfer, visible light signal transfer, ultraviolet light signal transfer, wireless signal transfer along the electromagnetic spectrum, or some combination thereof. Output devices 1150 may include any ports, plugs, antennae, wired or wireless transmitters, wired or wireless transceivers, or any other components necessary for or usable to implement the communication types listed above, such as cellular Subscriber Identity Module (SIM) cards.

Input devices 1160 may include circuitry providing a portion of a user interface. Input devices 1160 may include an alpha-numeric keypad, such as a keyboard, for inputting alpha-numeric and other information, or a pointing device, such as a mouse, a trackball, stylus, or cursor direction keys. Input devices 1160 may include touch-sensitive surfaces as well, either integrated with a display as in a touchscreen, or separate from a display as in a trackpad. Touch-sensitive surfaces may in some cases detect localized variable pressure or force detection. In some cases, the input device circuitry may allow for receipt of data over an audio jack, a microphone jack, a universal serial bus (USB) port/plug, an Apple® Lightning® port/plug, an Ethernet port/plug, a fiber optic port/plug, a proprietary wired port/plug, a wired local area network (LAN) port/plug, a BLUETOOTH® wireless signal transfer, a BLUETOOTH® low energy (BLE) wireless signal transfer, an IBEACON® wireless signal transfer, a radio-frequency identification (RFID) wireless signal transfer, near-field communications (NFC) wireless signal transfer, dedicated short range communication (DSRC) wireless signal transfer, 802.11 Wi-Fi wireless signal transfer, wireless local area network (WLAN) signal transfer, Visible Light Communication (VLC), Worldwide Interoperability for Microwave Access (WiMAX), Infrared (IR) communication wireless signal transfer, Public Switched Telephone Network (PSTN) signal transfer, Integrated Services Digital Network (ISDN) signal transfer, 3G/4G/5G/LTE cellular data network wireless signal transfer, personal area network (PAN) signal transfer, wide area network (WAN) signal transfer, ad-hoc network signal transfer, radio wave signal transfer, microwave signal transfer, infrared signal transfer, visible light signal transfer, ultraviolet light signal transfer, wireless signal transfer along the electromagnetic spectrum, or some combination thereof. Input devices 1160 may include any ports, plugs, antennae, wired or wireless receivers, wired or wireless transceivers, or any other components necessary for or usable to implement the communication types listed above, such as cellular SIM cards.

Input devices 1160 may include receivers or transceivers used for positioning of the computing system 1100 as well. These may include any of the wired or wireless signal receivers or transceivers. For example, a location of the computing system 1100 can be determined based on signal strength of signals as received at the computing system 1100 from three cellular network towers, a process known as cellular triangulation. Fewer than three cellular network towers can also be used—even one can be used—though the location determined from such data will be less precise (e.g., somewhere within a particular circle for one tower, somewhere along a line or within a relatively small area for two towers) than via triangulation. More than three cellular network towers can also be used, further enhancing the location's accuracy. Similar positioning operations can be performed using proximity beacons, which might use short-range wireless signals such as BLUETOOTH® wireless signals, BLUETOOTH® low energy (BLE) wireless signals, IBEACON® wireless signals, personal area network (PAN) signals, microwave signals, radio wave signals, or other signals discussed above. Similar positioning operations can be performed using wired local area networks (LAN) or wireless local area networks (WLAN) where locations are known of one or more network devices in communication with the computing system 1100 such as a router, modem, switch, hub, bridge, gateway, or repeater.

These may also include Global Navigation Satellite System (GNSS) receivers or transceivers that are used to determine a location of the computing system 1100 based on receipt of one or more signals from one or more satellites associated with one or more GNSS systems. GNSS systems include, but are not limited to, the US-based Global Positioning System (GPS), the Russia-based Global Navigation Satellite System (GLONASS), the China-based BeiDou Navigation Satellite System (BDS), and the Europe-based Galileo GNSS. Input devices 1160 may include receivers or transceivers corresponding to one or more of these GNSS systems.

Display system 1170 may include a liquid crystal display (LCD), a plasma display, an organic light-emitting diode (OLED) display, a low-temperature poly-silicon (LTPO) display, an electronic ink or "e-paper" display, a projector-based display, a holographic display, or another suitable display device. Display system 1170 receives textual and graphical information, and processes the information for output to the display device. The display system 1170 may include multiple-touch touchscreen input capabilities, such as capacitive touch detection, resistive touch detection, surface acoustic wave touch detection, or infrared touch detection. Such touchscreen input capabilities may or may not allow for variable pressure or force detection.

Peripherals 1180 may include any type of computer support device to add additional functionality to the computer system. For example, peripheral device(s) 1180 may include one or more additional output devices of any of the types discussed with respect to output device 1150, one or more additional input devices of any of the types discussed with respect to input device 1160, one or more additional display systems of any of the types discussed with respect to display system 1170, one or more memories or mass storage devices or portable storage devices of any of the types discussed with respect to memory 1120 or mass storage 1130 or portable storage 1140, a modem, a router, an antenna, a wired or wireless transceiver, a printer, a bar code scanner, a quick-response ("QR") code scanner, a magnetic stripe card reader, a integrated circuit chip (ICC) card reader such as a smartcard reader or a EUROPAY®-MASTERCARD®-VISA® (EMV) chip card reader, a near field communication (NFC) reader, a document/image scanner, a visible light camera, a thermal/infrared camera, an ultraviolet-sensitive camera, a night vision camera, a light sensor, a phototransistor, a photoresistor, a thermometer, a thermistor, a battery, a power source, a proximity sensor, a laser rangefinder, a sonar transceiver, a radar transceiver, a lidar transceiver, a network device, a motor, an actuator, a pump, a conveyer belt, a robotic arm, a rotor, a drill, a chemical assay device, or some combination thereof.

The components contained in the computer system 1100 of FIG. 11 can include those typically found in computer systems that may be suitable for use with some aspects of the subject technology and represent a broad category of such computer components that are well known in the art. That said, the computer system 1100 of FIG. 11 can be customized and specialized for the purposes discussed herein and to carry out the various operations discussed herein, with specialized hardware components, specialized arrangements of hardware components, and/or specialized software. Thus, the computer system 1100 of FIG. 11 can be a personal computer, a hand held computing device, a telephone ("smartphone" or otherwise), a mobile computing device, a workstation, a server (on a server rack or otherwise), a minicomputer, a mainframe computer, a tablet computing device, a wearable device (such as a watch, a ring, a pair of glasses, or another type of jewelry or clothing or accessory), a video game console (portable or otherwise), an e-book reader, a media player device (portable or otherwise), a vehicle-based computer, another type of computing device, or some combination thereof. The computer system 1100 may in some cases be a virtual computer system executed by another computer system. The computer can also include different bus configurations, networked platforms, multi-processor platforms, etc. Various operating systems can be used including Unix®, Linux®, FreeBSD®, FreeNAS®, pfSense®, Windows®, Apple® Macintosh OS® ("MacOS®"), Palm OS®, Google® Android®, Google® Chrome OS®, Chromium® OS®, OPENSTEP®, XNU®, Darwin®, Apple® iOS®, Apple® tvOS®, Apple® watchOS®, Apple® audioOS®, Amazon® Fire OS®, Amazon® Kindle OS®, variants of any of these, other suitable operating systems, or combinations thereof. The computer system 1100 may also use a Basic Input/Output System (BIOS) or Unified Extensible Firmware Interface (UEFI) as a layer upon which the operating system(s) are run.

In some cases, the computer system 1100 may be part of a multi-computer system that uses multiple computer systems 1100, each for one or more specific tasks or purposes. For example, the multi-computer system may include multiple computer systems 1100 communicatively coupled together via at least one of a personal area network (PAN), a local area network (LAN), a wireless local area network (WLAN), a municipal area network (MAN), a wide area network (WAN), or some combination thereof. The multi-computer system may further include multiple computer systems 1100 from different networks communicatively coupled together via the internet (also known as a "distributed" system).

Some aspects of the subject technology may be implemented in an application that may be operable using a variety of devices. Non-transitory computer-readable storage media refer to any medium or media that participate in providing instructions to a central processing unit (CPU) for execution and that may be used in the memory 1120, the mass storage 1130, the portable storage 1140, or some combination thereof. Such media can take many forms, including, but not limited to, non-volatile and volatile media such as optical or magnetic disks and dynamic memory, respectively. Some forms of non-transitory computer-readable media include, for example, a floppy disk, a flexible disk, a hard disk, magnetic tape, a magnetic strip/stripe, any other magnetic storage medium, flash memory, memristor memory, any other solid-state memory, a compact disc read only memory (CD-ROM) optical disc, a rewritable compact disc (CD) optical disc, digital video disk (DVD) optical disc, a blu-ray disc (BDD) optical disc, a holographic optical disk, another optical medium, a secure digital (SD) card, a micro secure digital (microSD) card, a Memory Stick® card, a smartcard chip, a EMV chip, a subscriber identity module (SIM) card, a mini/micro/nano/pico SIM card, another integrated circuit (IC) chip/card, random access memory (RAM), static RAM (SRAM), dynamic RAM (DRAM), read-only memory (ROM), programmable read-only memory (PROM), erasable programmable read-only memory (EPROM), electrically erasable programmable read-only memory (EEPROM), flash EPROM (FLASHEPROM), cache memory (L1/L2/L3/L4/L5/L15), resistive random-access memory (RRAM/ReRAM), phase change memory (PCM), spin transfer torque RAM (STT-RAM), another memory chip or cartridge, or a combination thereof.

Various forms of transmission media may be involved in carrying one or more sequences of one or more instructions to a processor 1110 for execution. A bus 1190 carries the data to system RAM or another memory 1120, from which a processor 1110 retrieves and executes the instructions. The instructions received by system RAM or another memory 1120 can optionally be stored on a fixed disk (mass storage device 1130/portable storage 1140) either before or after execution by processor 1110. Various forms of storage may likewise be implemented as well as the necessary network interfaces and network topologies to implement the same.

While various flow diagrams provided and described above may show a particular order of operations performed by some embodiments of the subject technology, it should be understood that such order is exemplary. Alternative embodiments may perform the operations in a different order, combine certain operations, overlap certain operations, or some combination thereof. It should be understood that unless disclosed otherwise, any process illustrated in any flow diagram herein or otherwise illustrated or described herein may be performed by a machine, mechanism, and/or computing system 1100 discussed herein, and may be performed automatically (e.g., in response to one or more triggers/conditions described herein), autonomously, semi-autonomously (e.g., based on received instructions), or a combination thereof. Furthermore, any action described herein as occurring in response to one or more particular triggers/conditions should be understood to optionally occur automatically response to the one or more particular triggers/conditions.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claims.

Illustrative aspects of the disclosure include:

Aspect 1. An apparatus for airflow control, the apparatus comprising: a first inspiratory lumen that is configured to receive a first inspiratory gaseous volume and to provide the first inspiratory gaseous volume to a first portion of an airway of a patient while the first inspiratory lumen is at least partially inserted into the airway; a second inspiratory lumen that is configured to receive a second inspiratory gaseous volume and to provide the second inspiratory gaseous volume to a second portion of the airway while the second inspiratory lumen is at least partially inserted into the airway; and one or more expiratory lumens that are configured to evacuate an expiratory gaseous volume from at least one of the first portion of the airway and the second portion of the airway while the one or more expiratory lumens are at least partially inserted into the airway.

Aspect 2. The apparatus of Aspect 1, wherein the first portion of the airway includes a first lung, wherein the second portion of the airway includes a second lung distinct from the first lung.

Aspect 3. The apparatus of Aspect 2, wherein the first inspiratory lumen is configured to provide the first inspiratory gaseous volume to a first lobe of the first lung, wherein the one or more expiratory lumens are configured to evacuate the expiratory gaseous volume from a second lobe of the first lung, wherein the first lobe is different than the second lobe.

Aspect 4. The apparatus of any of Aspects 1 to 3, wherein the first portion of the airway includes a first bronchus, wherein the second portion of the airway includes a second bronchus distinct from the first bronchus.

Aspect 5. The apparatus of any of Aspects 1 to 4, wherein the first inspiratory lumen receives the first inspiratory gaseous volume from a first gas source, and wherein second inspiratory lumen receives the second inspiratory gaseous volume from the first gas source.

Aspect 6. The apparatus of any of Aspects 1 to 5, wherein the first inspiratory lumen receives the first inspiratory gaseous volume from a first gas source, and wherein second inspiratory lumen receives the second inspiratory gaseous volume from a second gas source.

Aspect 7. The apparatus of any of Aspects 1 to 6, wherein the first inspiratory gaseous volume and the second inspiratory gaseous volume both include an inspiratory mixture of a plurality of gases that are mixed according to one or more predetermined ratios.

Aspect 8. The apparatus of Aspect 7, wherein the inspiratory mixture includes carbon dioxide.

Aspect 9. The apparatus of any of Aspects 1 to 8, further comprising an endotracheal tube, wherein the endotracheal tube includes at least the first inspiratory lumen, the second inspiratory lumen, and the one or more expiratory lumens.

Aspect 10. The apparatus of Aspect 9, wherein the first inspiratory lumen passes through the endotracheal tube and extends beyond a tip of the endotracheal tube toward the first portion of the airway, wherein the second inspiratory lumen passes through the endotracheal tube and extends beyond the tip of the endotracheal tube toward the second portion of the airway.

Aspect 11. The apparatus of Aspect 10, wherein the tip of the endotracheal tube includes the tip of the one or more expiratory lumens.

Aspect 12. The apparatus of any of Aspects 1 to 11, wherein the one or more expiratory lumens include a first expiratory lumen configured to evacuate a first expiratory gaseous volume from the first portion of the airway and a second expiratory lumen configured to evacuate a second expiratory gaseous volume from the second portion of the airway.

Aspect 13. The apparatus of Aspect 12, wherein the first expiratory lumen passes through an endotracheal tube and extends beyond a tip of the endotracheal tube toward the first portion of the airway, wherein the second expiratory lumen passes through the endotracheal tube and extends beyond the tip of the endotracheal tube toward the second portion of the airway.

Aspect 14. The apparatus of any of Aspects 12 to 13, further comprising: a first expiratory mixture pressurizer that provides suction to evacuate the first expiratory gaseous volume from the first portion of the airway through the first expiratory lumen and a second expiratory mixture pressurizer that provides suction to evacuate the second expiratory gaseous volume from the second portion of the airway through the second expiratory lumen.

Aspect 15. The apparatus of any of Aspects 12 to 14, wherein the one or more expiratory lumens also include a third expiratory lumen configured to evacuate a third expiratory gaseous volume from a third portion of the airway.

Aspect 16. The apparatus of any of Aspects 1 to 15, further comprising: one or more inspiratory flow control mechanisms that control flow of the first inspiratory gaseous volume to the first portion of the airway through the first inspiratory lumen and that control flow of second inspiratory gaseous volume to the second portion of the airway through the second inspiratory lumen.

Aspect 17. The apparatus of any of Aspects 1 to 16, further comprising: one or more expiratory flow control mechanisms that provide pressurized suction to control flow of the expiratory gaseous volume from at least one of the first portion of the airway and the second portion of the airway to an expiratory air output through the one or more expiratory lumens.

Aspect 18. The apparatus of Aspect 17, further comprising: one or more inspiratory flow control mechanisms that provide the first inspiratory gaseous volume to the first inspiratory lumen and that provide the second inspiratory gaseous volume to the second inspiratory lumen; a memory storing instructions; and a processor that executes the instructions, wherein execution of the instructions by the processor causes the processor to: maintain net inspiratory flow at a first level during a first portion of each of a plurality of respiratory cycles, wherein the net inspiratory flow corresponds to provision of both the first inspiratory gaseous volume and the second inspiratory gaseous volume, and maintain net expiratory flow at a second level during the first portion of each of the plurality of respiratory cycles, wherein the net expiratory flow corresponds to provision of pressurized suction to control flow of the expiratory gaseous volume.

Aspect 19. The apparatus of Aspect 18, wherein the first portion of each of the plurality of respiratory cycles is an inspiration, and wherein an absolute value of the net inspiratory flow is greater than an absolute value of the net expiratory flow.

Aspect 20. The apparatus of Aspect 18, wherein the first portion of each of the plurality of respiratory cycles is an expiration, and wherein an absolute value of the net inspiratory flow is less than an absolute value of the net expiratory flow.

Aspect 21. The apparatus of Aspect 18, wherein the first portion of each of the plurality of respiratory cycles is a hold, and wherein an absolute value of the net inspiratory flow is equal to an absolute value of the net expiratory flow.

Aspect 22. The apparatus of any of Aspects 1 to 21, further comprising: an intratracheal sensor that measures an intratracheal pressure in a trachea of the patient; and one or more pressurizers, wherein the one or more pressurizers are configured to provide airflow pressure based on the intratracheal pressure, wherein the airflow pressure includes at least one of a first inspiratory pressure to provide the first inspiratory gaseous volume to the first portion of the airway via the first inspiratory lumen, a second inspiratory pressure to provide the second inspiratory gaseous volume to the second portion of the airway via the second inspiratory lumen, and an expiratory pressure to evacuate the expiratory gaseous volume from at least one of the first portion of the airway and the second portion of the airway via the one or more expiratory lumens.

Aspect 23. The apparatus of any of Aspects 1 to 22, further comprising: one or more markers along at least one of the first inspiratory lumen, the second inspiratory lumen, and the one or more expiratory lumens, wherein the one or more markers are at least one of radiopaque, radioactive, emissive of a magnetic field, and emissive of one or more electromagnetic signals.

Aspect 24. The apparatus of any of Aspects 1 to 23, further comprising: a third inspiratory lumen that is configured to receive a third inspiratory gaseous volume and to provide the third inspiratory gaseous volume to a third portion of the airway while the third inspiratory lumen is at least partially inserted into the airway.

Aspect 25. The apparatus of any of Aspects 1 to 24, further comprising: a microfilter adapter that includes a microfilter medium and one or more one-way airflow valves, wherein the microfilter adapter passes airflow through the one or more one-way airflow valves and filters the airflow through the microfilter medium, wherein the airflow includes at least one of the first inspiratory gaseous volume, the second inspiratory gaseous volume, and the expiratory gaseous volume.

Aspect 26. A method for airflow control, the method comprising: receiving a first inspiratory gaseous volume into a first inspiratory lumen; providing the first inspiratory gaseous volume to a first portion of an airway using the first inspiratory lumen while the first inspiratory lumen is at least partially inserted into the airway of a patient; receiving a second inspiratory gaseous volume into a second inspiratory lumen; providing the second inspiratory gaseous volume to a second portion of the airway using the second inspiratory lumen while the second inspiratory lumen is at least partially inserted into the airway; and evacuating an expiratory gaseous volume from the first portion of the airway and from the second portion of the airway using one or more expiratory lumens while the one or more expiratory lumens are at least partially inserted into the airway.

Aspect 27. The method of Aspect 26, wherein the first portion of the airway includes a first lung, wherein the second portion of the airway includes a second lung distinct from the first lung.

Aspect 28. The method of Aspect 27, wherein providing the first inspiratory gaseous volume using the first inspiratory lumen includes providing the first inspiratory gaseous volume to the a first lobe of the first lung using the first inspiratory lumen, wherein evacuating the expiratory gaseous volume using one or more expiratory lumens includes evacuating the expiratory gaseous volume from a second lobe of the first lung using one or more expiratory lumens, wherein the first lobe is different than the second lobe.

Aspect 29. The method of any of Aspects 26 to 28, wherein the first portion of the airway includes a first bronchus, wherein the second portion of the airway includes a second bronchus distinct or from the first bronchus.

Aspect 30. The method of any of Aspects 26 to 29, wherein receiving the first inspiratory gaseous volume into the first inspiratory lumen includes receiving the first inspiratory gaseous volume into the first inspiratory lumen from a first gas source, wherein receiving the second inspiratory gaseous volume into the second inspiratory lumen includes receiving the second inspiratory gaseous volume into the second inspiratory lumen from the first gas source.

Aspect 31. The method of any of Aspects 26 to 30, wherein receiving the first inspiratory gaseous volume into the first inspiratory lumen includes receiving the first inspiratory gaseous volume into the first inspiratory lumen from a first gas source, wherein receiving the second inspiratory gaseous volume into the second inspiratory lumen includes receiving the second inspiratory gaseous volume into the second inspiratory lumen from a second gas source.

Aspect 32. The method of any of Aspects 26 to 31, further comprising: mixing a plurality of gases into an inspiratory mixture according to one or more predetermined ratios, wherein the first inspiratory gaseous volume and the second inspiratory gaseous volume both include the inspiratory mixture.

Aspect 33. The method of Aspect 32, wherein the inspiratory mixture includes carbon dioxide.

Aspect 34. The method of any of Aspects 26 to 33, wherein an endotracheal tube includes at least the first inspiratory lumen, the second inspiratory lumen, and the one or more expiratory lumens.

Aspect 35. The method of Aspect 34, wherein the first inspiratory lumen passes through the endotracheal tube and extends beyond a tip of the endotracheal tube toward the first portion of the airway, wherein the second inspiratory lumen passes through the endotracheal tube and extends beyond the tip of the endotracheal tube toward the second portion of the airway.

Aspect 36. The method of Aspect 35, wherein the tip of the endotracheal tube includes the tip of the one or more expiratory lumens.

Aspect 37. The method of any of Aspects 26 to 36, wherein the one or more expiratory lumens include a first expiratory lumen and a second expiratory lumen, wherein evacuating the expiratory gaseous volume from the first portion of the airway and from the second portion of the airway using one or more expiratory lumens includes evacuating a first portion of the expiratory gaseous volume from the first portion of the airway using the first expiratory lumen and evacuating a second portion of the expiratory gaseous volume from the second portion of the airway using the second expiratory lumen.

Aspect 38. The method of Aspect 37, wherein the first expiratory lumen passes through an endotracheal tube and extends beyond a tip of the endotracheal tube toward the first portion of the airway, wherein the second expiratory lumen passes through the endotracheal tube and extends beyond the tip of the endotracheal tube toward the second portion of the airway.

Aspect 39. The method of any of Aspects 37 to 38, further comprising: providing primary suction, using a first expiratory mixture pressurizer, to evacuate the first expiratory gaseous volume from the first portion of the airway through the first expiratory lumen; and providing secondary suction, using a second expiratory mixture pressurizer, to evacuate the second expiratory gaseous volume from the second portion of the airway through the second expiratory lumen.

Aspect 40. The method of any of Aspects 37 to 39, further comprising: evacuating a third expiratory gaseous volume from a third portion of the airway using a third expiratory lumens while the third expiratory lumen is at least partially inserted into the airway, wherein the one or more expiratory lumens also include the third expiratory lumen.

Aspect 41. The method of any of Aspects 26 to 40, further comprising: controlling flow, of the first inspiratory gaseous volume to the first portion of the airway through the first inspiratory lumen and of the second inspiratory gaseous volume to the second portion of the airway through the second inspiratory lumen.

Aspect 42. The method of any of Aspects 26 to 41, further comprising: providing pressurized suction, using one or more expiratory flow control mechanisms, to control flow of the expiratory gaseous volume from at least one of the first portion of the airway and the second portion of the airway to an expiratory air output through the one or more expiratory lumens.

Aspect 43. The method of Aspect 42, further comprising: maintaining net inspiratory flow at a first level during a first portion of each of a plurality of respiratory cycles, wherein the net inspiratory flow corresponds to provision of both the first inspiratory gaseous volume and the second inspiratory gaseous volume using one or more inspiratory flow control mechanisms, and maintaining net expiratory flow at a second level during the first portion of each of the plurality of respiratory cycles, wherein the net expiratory flow corresponds to provision of the pressurized suction to control the flow of the expiratory gaseous volume using the one or more expiratory flow control mechanisms.

Aspect 44. The method of Aspect 43, wherein the first portion of each of the plurality of respiratory cycles is an inspiration, and wherein an absolute value of the net inspiratory flow is greater than an absolute value of the net expiratory flow.

Aspect 45. The method of Aspect 43, wherein the first portion of each of the plurality of respiratory cycles is an expiration, and wherein an absolute value of the net inspiratory flow is less than an absolute value of the net expiratory flow.

Aspect 46. The method of Aspect 43, wherein the first portion of each of the plurality of respiratory cycles is a hold, and wherein an absolute value of the net inspiratory flow is equal to an absolute value of the net expiratory flow.

Aspect 47. The method of any of Aspects 26 to 46, further comprising: measuring an intratracheal pressure in a trachea of the patient using an intratracheal sensor; and provide airflow pressure using one or more pressurizers based on the intratracheal pressure, wherein the airflow pressure includes at least one of a first inspiratory pressure to provide the first inspiratory gaseous volume to the first portion of the airway via the first inspiratory lumen, a second inspiratory pressure to provide the second inspiratory gaseous volume to the second portion of the airway via the second inspiratory lumen, and an expiratory pressure to evacuate the expiratory gaseous volume from at least one of the first portion of the airway and the second portion of the airway via the one or more expiratory lumens.

Aspect 48. The method of any of Aspects 26 to 47, wherein one or more markers are included along at least one of the first inspiratory lumen, the second inspiratory lumen, and the one or more expiratory lumens, wherein the one or more markers are at least one of radiopaque, radioactive, emissive of a magnetic field, and emissive of one or more electromagnetic signals.

Aspect 49. The method of any of Aspects 26 to 48, further comprising: receiving a third inspiratory gaseous volume into a third inspiratory lumen; providing the third inspiratory gaseous volume to a third portion of an airway using the third inspiratory lumen while the third inspiratory lumen is at least partially inserted into the airway.

Aspect 50. The method of any of Aspects 26 to 49, further comprising: filtering airflow at least in part by passing airflow through one or more one-way airflow valves of a microfilter adapter and through a microfilter medium of the microfilter adapter, wherein the airflow includes at least one of the first inspiratory gaseous volume, the second inspiratory gaseous volume, and the expiratory gaseous volume.

Aspect 51: A non-transitory computer-readable medium having stored thereon instructions that, when executed by one or more processors, cause the one or more processors to: # receive a first inspiratory gaseous volume into a first inspiratory lumen; provide the first inspiratory gaseous volume to a first portion of an airway of a patient using the first inspiratory lumen while the first inspiratory lumen is at least partially inserted into the airway; receive a second inspiratory gaseous volume into a second inspiratory lumen; provide the second inspiratory gaseous volume to a second portion of the airway use the second inspiratory lumen while the second inspiratory lumen is at least partially inserted into the airway; and evacuate an expiratory gaseous volume from the first portion of the airway and from the second portion of the airway using one or more expiratory lumens while the one or more expiratory lumens are at least partially inserted into the airway.

Aspect 52: The non-transitory computer-readable medium of Aspect 51, further comprising any of Aspects 26 to 50.

Aspect 53: An apparatus for airflow control, the apparatus comprising: means for receiving a first inspiratory gaseous volume into a first inspiratory lumen; means for providing the first inspiratory gaseous volume to a first portion of an airway using the first inspiratory lumen while the first inspiratory lumen is at least partially inserted into the airway of a patient; means for receiving a second inspiratory gaseous volume into a second inspiratory lumen; means for providing the second inspiratory gaseous volume to a second portion of the airway using the second inspiratory lumen while the second inspiratory lumen is at least partially inserted into the airway; and means for evacuating an expiratory gaseous volume from the first portion of the airway and from the second portion of the airway using one or more expiratory lumens while the one or more expiratory lumens are at least partially inserted into the airway.

Aspect 54: The apparatus of Aspect 54, further comprising means for performing any of the operations of any of Aspects 26 to 50.

What is claimed is:

1. An apparatus for flow control, the apparatus comprising:
    an inspiratory lumen, wherein an inspiratory gas pressure controller is configured to control provision of an inspiratory gaseous flow through the inspiratory lumen to a first portion of an airway of a patient while the inspiratory lumen is at least partially inserted into the airway;
    an expiratory lumen, wherein an expiratory gas pressure controller is configured to control evacuation of an expiratory gaseous flow through the expiratory lumen from a second portion of the airway of the patient while the expiratory lumen is at least partially inserted into the airway, wherein the expiratory gas pressure controller is configured to vary an application of expiratory pressure to the expiratory lumen over time; and
    a processor that is configured to control at least the inspiratory gas pressure controller and the expiratory gas pressure controller based on respective properties of the inspiratory gaseous flow and the expiratory gaseous flow.

2. The apparatus of claim 1, further comprising:
    a second inspiratory lumen, wherein a second inspiratory gas pressure controller is configured to control provision of a second inspiratory gaseous flow through the second inspiratory lumen to a third portion of the airway of the patient while the second inspiratory lumen is at least partially inserted into the airway.

3. The apparatus of claim 2, wherein the inspiratory lumen is configured to be directed toward a first direction while the inspiratory lumen is at least partially inserted into the airway, and wherein the second inspiratory lumen is configured to be directed toward a second direction while the second inspiratory lumen is at least partially inserted into the airway, wherein the second direction is distinct from the first direction.

4. The apparatus of claim 2, wherein the second inspiratory lumen is configured to be threaded through the inspiratory lumen.

5. The apparatus of claim 1, further comprising:
    a second expiratory lumen, wherein a second expiratory gas pressure controller is configured to control evacuation of a second expiratory gaseous flow through the second expiratory lumen from a third portion of the airway of the patient while the second expiratory lumen is at least partially inserted into the airway.

6. The apparatus of claim 5, wherein the expiratory lumen is configured to be directed toward a first direction while the expiratory lumen is at least partially inserted into the airway, and wherein the second expiratory lumen is configured to be directed toward a second direction while the second expiratory lumen is at least partially inserted into the airway, wherein the second direction is distinct from the first direction.

7. The apparatus of claim 5, wherein the second expiratory lumen is configured to be threaded through the expiratory lumen.

8. The apparatus of claim 1, wherein at least one of the inspiratory lumen or the expiratory lumen is curved.

9. The apparatus of claim 1, further comprising:
    an additional lumen that is curved, wherein the additional lumen is at least one of an additional inspiratory lumen or an additional expiratory lumen.

10. The apparatus of claim 1, wherein the inspiratory lumen is configured to be threaded through the expiratory lumen.

11. The apparatus of claim 1, wherein the expiratory lumen is configured to be threaded through the inspiratory lumen.

12. The apparatus of claim 1, wherein a lumen portion is at least partially pliable, wherein the lumen portion is a portion of at least one of the inspiratory lumen or the expiratory lumen.

13. The apparatus of claim 1, wherein a lumen portion is at least partially rigid, wherein the lumen portion is a portion of at least one of the inspiratory lumen or the expiratory lumen.

14. The apparatus of claim 1, further comprising:
    a marker along at least a portion of at least one of the inspiratory lumen or the expiratory lumen, wherein the marker includes at least one of a solenoid, a magnetic field emitter, a electromagnetic field emitter, a wireless signal transmitter, a radioactive material, a radiopaque material, or a radiolucent material.

15. The apparatus of claim 1, wherein the processor is configured to control the inspiratory gas pressure controller and the expiratory gas pressure controller to cause the inspiratory gaseous flow and the expiratory gaseous flow to be related based on a function.

16. The apparatus of claim 1, further comprising:
    an adapter configured to be coupled to an endotracheal tube, wherein the adapter is configured to segregate a gaseous flow within the endotracheal tube into a plurality of separate flows, wherein the plurality of separate flows include at least the inspiratory gaseous flow through the inspiratory lumen and the expiratory gaseous flow through the expiratory lumen.

17. The apparatus of claim 1, further comprising:
    a filter in the inspiratory lumen, wherein the filter is configured to filter at least a portion of the inspiratory gaseous flow as the inspiratory gaseous flow passes through the inspiratory lumen; and
    a one-way flow valve configured to restrict the expiratory gaseous flow from reaching the filter.

18. The apparatus of claim 1, wherein the inspiratory lumen is configured to reach a first depth corresponding to the first portion of the airway of the patient, wherein the expiratory lumen is configured to reach a second depth corresponding to the second portion of the airway of the patient, wherein the first depth is distinct from the second depth.

19. The apparatus of claim 1, wherein at least one of a first position of the inspiratory lumen in the airway or a second position of the expiratory lumen in the airway is changeable.

20. The apparatus of claim 1, further comprising:
a first flow pressure sensor along the inspiratory lumen; and
a second flow pressure sensor along the expiratory lumen, wherein the processor is configured to control the inspiratory gas pressure controller and the expiratory gas pressure controller based on respective pressure measurements from the first flow pressure sensor and the second flow pressure sensor.

21. The apparatus of claim 1, further comprising:
a pressure sensor configured to be located at a trachea of the patient, wherein the pressure sensor measures a pressure associated with a gas flow within the trachea of the patient, wherein the processor is configured to control at least one of the inspiratory gas pressure controller or the expiratory gas pressure controller based on a pressure measurement from the pressure sensor.

22. The apparatus of claim 1, wherein the processor is configured to, based on at least one measurement of a concentration of a specified gas in a mixture of gases in the expiratory gaseous flow, perform at least one of:
cause the inspiratory gas pressure controller to modify an inspiratory pressure of the inspiratory gaseous flow, or
cause the expiratory gas pressure controller to modify an expiratory pressure of the expiratory gaseous flow;
wherein the at least one measurement is received from at least one sensor.

23. The apparatus of claim 22, wherein the specified gas is carbon dioxide.

24. The apparatus of claim 1, wherein a diameter of a lumen is based on a diameter of a bronchus in the airway of the patient, wherein the lumen is at least one of the inspiratory lumen or the expiratory lumen, wherein the bronchus is in at least one of the first portion of the airway of the patient or the second portion of the airway of the patient.

25. The apparatus of claim 1, further comprising:
an extraction tube configured to be coupled to a suction system, the extraction tube configured to extract non-gaseous matter from the expiratory gaseous flow.

26. The apparatus of claim 25, wherein the suction system is configured to synchronize flow at the extraction tube during suctioning with at least one of the inspiratory gaseous flow or the expiratory gaseous flow to minimize net gas volume loss from the airway of the patient.

27. The apparatus of claim 1, wherein the processor is configured to cause the expiratory gas pressure controller to apply a first pressure to the expiratory lumen, wherein the first pressure is less than a second pressure in the second portion of the airway of the patient.

28. The apparatus of claim 1, wherein the processor is configured to cause the inspiratory gas pressure controller to apply a first pressure to the inspiratory lumen, wherein the first pressure is greater than a second pressure in the second portion of the airway of the patient.

29. The apparatus of claim 1, wherein the 7 processor is configured to delay initiation of the inspiratory gaseous flow to allow for a full expiration from the airway of the patient to calibrate the 7 processor, wherein the full expiration is an expiration from a peak airway pressure associated with an inspiration to a trough airway pressure associated with a positive end-expiratory pressure (PEEP).

30. The apparatus of claim 1, wherein the expiratory gas pressure controller is configured to control the evacuation of the expiratory gaseous flow to assist with a full expiration, wherein the full expiration is an expiration from a peak airway pressure associated with an inspiration to a trough airway pressure associated with a positive end-expiratory pressure (PEEP), wherein the processor is configured to identify a threshold volume corresponding to the PEEP.

31. The apparatus of claim 30, wherein the processor is configured to add one or more inspiratory gas volumes and subtract one or more expiratory gas volumes to track a volume in at least a portion of the airway of the patient relative to the threshold volume, wherein the processor is configured to control at least one of the inspiratory gas pressure controller or the expiratory gas pressure controller based on the tracked volume, the one or more inspiratory gas volumes passing through the inspiratory lumen, the one or more expiratory gas volumes passing through at least one of the expiratory lumen or a suction system.

32. The apparatus of claim 30, wherein the processor is configured to prevent at least one of the expiratory gas pressure controller or a suction system from reducing a volume in at least a portion of the airway to be below a threshold volume when evacuating the expiratory gaseous flow, wherein the threshold volume is associated with a positive end-expiratory pressure (PEEP), and wherein the suction system is coupled to an extraction tube.

33. A method for flow control, the method comprising:
controlling, using an inspiratory gas pressure controller, provision of an inspiratory gaseous flow through an inspiratory lumen to a first portion of an airway of a patient while the inspiratory lumen is at least partially inserted into the airway;
controlling, using an expiratory gas pressure controller, evacuation of an expiratory gaseous flow through an expiratory lumen from a second portion of the airway of the patient while the expiratory lumen is at least partially inserted into the airway, wherein the expiratory gas pressure controller is configured to vary expiratory pressure over time; and
controlling, by a controller, the inspiratory gas pressure controller and the expiratory gas pressure controller based on respective properties of the inspiratory gaseous flow and the expiratory gaseous flow.

34. The apparatus of claim 1, wherein a distal end of the inspiratory lumen is configured to extend further into the airway than the distal end of the expiratory lumen during both inspiration and expiration.

35. The apparatus of claim 2, wherein the second inspiratory gas pressure controller is the inspiratory gas pressure controller.

36. The apparatus of claim 5, wherein the second expiratory gas pressure controller is the expiratory gas pressure controller.

37. The apparatus of claim 1, wherein the inspiratory gas pressure controller includes at least one of a valve, a pump, a compressor, a decompressor, a gas buffer, a pressurizer, a depressurizer, a turbine, an actuator, or a suction device.

38. The apparatus of claim 1, wherein the expiratory gas pressure controller includes at least one of a valve, a pump, a compressor, a decompressor, a gas buffer, a pressurizer, a depressurizer, a turbine, an actuator, or a suction device.

39. An apparatus for flow control, the apparatus comprising:
- an inspiratory lumen, wherein an inspiratory gas pressure controller is configured to control provision of an inspiratory gaseous flow through the inspiratory lumen to a first portion of an airway of a patient while the inspiratory lumen is at least partially inserted into the airway;
- a filter in the inspiratory lumen, wherein the filter is configured to filter at least a portion of the inspiratory gaseous flow as the inspiratory gaseous flow passes through the inspiratory lumen;
- an expiratory lumen, wherein an expiratory gas pressure controller is configured to control evacuation of an expiratory gaseous flow through the expiratory lumen from a second portion of the airway of the patient while the expiratory lumen is at least partially inserted into the airway;
- a one-way flow valve configured to restrict the expiratory gaseous flow from reaching the filter; and
- a processor that is configured to control at least the inspiratory gas pressure controller and the expiratory gas pressure controller based on respective properties of the inspiratory gaseous flow and the expiratory gaseous flow.

40. The apparatus of claim 39, further comprising:
- a second inspiratory lumen, wherein a second inspiratory gas pressure controller is configured to control provision of a second inspiratory gaseous flow through the second inspiratory lumen to a third portion of the airway of the patient while the second inspiratory lumen is at least partially inserted into the airway.

41. The apparatus of claim 40, wherein the inspiratory lumen is configured to be directed toward a first direction while the inspiratory lumen is at least partially inserted into the airway, and wherein the second inspiratory lumen is configured to be directed toward a second direction while the second inspiratory lumen is at least partially inserted into the airway, wherein the second direction is distinct from the first direction.

42. The apparatus of claim 40, wherein the second inspiratory lumen is configured to be threaded through the inspiratory lumen.

43. The apparatus of claim 39, further comprising:
- a second expiratory lumen, wherein a second expiratory gas pressure controller is configured to control evacuation of a second expiratory gaseous flow through the second expiratory lumen from a third portion of the airway of the patient while the second expiratory lumen is at least partially inserted into the airway.

44. The apparatus of claim 43, wherein the expiratory lumen is configured to be directed toward a first direction while the expiratory lumen is at least partially inserted into the airway, and wherein the second expiratory lumen is configured to be directed toward a second direction while the second expiratory lumen is at least partially inserted into the airway, wherein the second direction is distinct from the first direction.

45. The apparatus of claim 43, wherein the second expiratory lumen is configured to be threaded through the expiratory lumen.

46. The apparatus of claim 39, wherein at least one of the inspiratory lumen or the expiratory lumen is curved.

47. The apparatus of claim 39, further comprising:
- an additional lumen that is curved, wherein the additional lumen is at least one of an additional inspiratory lumen or an additional expiratory lumen.

48. The apparatus of claim 39, wherein the inspiratory lumen is configured to be threaded through the expiratory lumen.

49. The apparatus of claim 39, wherein the expiratory lumen is configured to be threaded through the inspiratory lumen.

50. The apparatus of claim 39, wherein a lumen portion is at least partially pliable, wherein the lumen portion is a portion of at least one of the inspiratory lumen or the expiratory lumen.

51. The apparatus of claim 39, wherein a lumen portion is at least partially rigid, wherein the lumen portion is a portion of at least one of the inspiratory lumen or the expiratory lumen.

52. The apparatus of claim 39, further comprising:
- a marker along at least a portion of at least one of the inspiratory lumen or the expiratory lumen, wherein the marker includes at least one of a solenoid, a magnetic field emitter, a electromagnetic field emitter, a wireless signal transmitter, a radioactive material, a radiopaque material, or a radiolucent material.

53. The apparatus of claim 39, wherein the processor is configured to control the inspiratory gas pressure controller and the expiratory gas pressure controller to cause the inspiratory gaseous flow and the expiratory gaseous flow to be related based on a function.

54. The apparatus of claim 39, further comprising:
- an adapter configured to be coupled to an endotracheal tube, wherein the adapter is configured to segregate a gaseous flow within the endotracheal tube into a plurality of separate flows, wherein the plurality of separate flows include at least the inspiratory gaseous flow through the inspiratory lumen and the expiratory gaseous flow through the expiratory lumen.

55. The apparatus of claim 39, wherein the inspiratory lumen is configured to reach a first depth corresponding to the first portion of the airway of the patient, wherein the expiratory lumen is configured to reach a second depth corresponding to the second portion of the airway of the patient, wherein the first depth is distinct from the second depth.

56. The apparatus of claim 39, wherein at least one of a first position of the inspiratory lumen in the airway or a second position of the expiratory lumen in the airway is changeable.

57. The apparatus of claim 39, further comprising:
- a first flow pressure sensor along the inspiratory lumen; and
- a second flow pressure sensor along the expiratory lumen, wherein the processor is configured to control the inspiratory gas pressure controller and the expiratory gas pressure controller based on respective pressure measurements from the first flow pressure sensor and the second flow pressure sensor.

58. The apparatus of claim 39, further comprising:
- a pressure sensor configured to be located at a trachea of the patient, wherein the pressure sensor measures a pressure associated with a gas flow within the trachea of the patient, wherein the processor is configured to control at least one of the inspiratory gas pressure controller or the expiratory gas pressure controller based on a pressure measurement from the pressure sensor.

59. The apparatus of claim 39, wherein the processor is configured to, based on at least one measurement of a concentration of a specified gas in a mixture of gases in the expiratory gaseous flow, perform at least one of:

cause the inspiratory gas pressure controller to modify an inspiratory pressure of the inspiratory gaseous flow, or cause the expiratory gas pressure controller to modify an expiratory pressure of the expiratory gaseous flow;

wherein the at least one measurement is received from at least one sensor.

60. The apparatus of claim 59, wherein the specified gas is carbon dioxide.

61. The apparatus of claim 39, wherein a diameter of a lumen is based on a diameter of a bronchus in the airway of the patient, wherein the lumen is at least one of the inspiratory lumen or the expiratory lumen, wherein the bronchus is in at least one of the first portion of the airway of the patient or the second portion of the airway of the patient.

62. The apparatus of claim 39, further comprising:
an extraction tube configured to be coupled to a suction system, the extraction tube configured to extract non-gaseous matter from the expiratory gaseous flow.

63. The apparatus of claim 62, wherein the suction system is configured to synchronize flow at the extraction tube during suctioning with at least one of the inspiratory gaseous flow or the expiratory gaseous flow to minimize net gas volume loss from the airway of the patient.

64. The apparatus of claim 39, wherein the processor is configured to cause the expiratory gas pressure controller to apply a first pressure to the expiratory lumen, wherein the first pressure is less than a second pressure in the second portion of the airway of the patient.

65. The apparatus of claim 39, wherein the processor is configured to cause the inspiratory gas pressure controller to apply a first pressure to the inspiratory lumen, wherein the first pressure is greater than a second pressure in the second portion of the airway of the patient.

66. The apparatus of claim 39, wherein the processor is configured to delay initiation of the inspiratory gaseous flow to allow for a full expiration from the airway of the patient to calibrate the processor, wherein the full expiration is an expiration from a peak airway pressure associated with an inspiration to a trough airway pressure associated with a positive end-expiratory pressure (PEEP).

67. The apparatus of claim 39, wherein the expiratory gas pressure controller is configured to control the evacuation of the expiratory gaseous flow to assist with a full expiration, wherein the full expiration is an expiration from a peak airway pressure associated with an inspiration to a trough airway pressure associated with a positive end-expiratory pressure (PEEP), wherein the processor is configured to identify a threshold volume corresponding to the PEEP.

68. The apparatus of claim 67, wherein the processor is configured to add one or more inspiratory gas volumes and subtract one or more expiratory gas volumes to track a volume in at least a portion of the airway of the patient relative to the threshold volume wherein the processor is configured to control at least one of the inspiratory gas pressure controller or the expiratory gas pressure controller based on the tracked volume, the one or more inspiratory gas volumes passing through the inspiratory lumen, the one or more expiratory gas volumes passing through at least one of the expiratory lumen or a suction system.

69. The apparatus of claim 39, wherein the processor is configured to prevent at least one of the expiratory gas pressure controller or a suction system from reducing a volume in at least a portion of the airway to be below a threshold volume when evacuating the expiratory gaseous flow, wherein the threshold volume is associated with a positive end-expiratory pressure (PEEP), and wherein the suction system is coupled to an extraction tube.

70. The apparatus of claim 39, wherein a distal end of the inspiratory lumen is configured to extend further into the airway than the distal end of the expiratory lumen during both inspiration and expiration.

71. The apparatus of claim 40, wherein the second inspiratory gas pressure controller is the inspiratory gas pressure controller.

72. The apparatus of claim 43, wherein the second expiratory gas pressure controller is the expiratory gas pressure controller.

73. The apparatus of claim 39, wherein the inspiratory gas pressure controller includes at least one of a valve, a pump, a compressor, a decompressor, a gas buffer, a pressurizer, a depressurizer, a turbine, an actuator, or a suction device.

74. The apparatus of claim 39, wherein the expiratory gas pressure controller includes at least one of a valve, a pump, a compressor, a decompressor, a gas buffer, a pressurizer, a depressurizer, a turbine, an actuator, or a suction device.

75. An apparatus for flow control, the apparatus comprising:
an inspiratory lumen, wherein an inspiratory gas pressure controller is configured to control provision of an inspiratory gaseous flow through the inspiratory lumen to a first portion of an airway of a patient while the inspiratory lumen is at least partially inserted into the airway;
an expiratory lumen, wherein an expiratory gas pressure controller is configured to control evacuation of an expiratory gaseous flow through the expiratory lumen from a second portion of the airway of the patient while the expiratory lumen is at least partially inserted into the airway;
a pressure sensor configured to be located at a trachea of the patient, wherein the pressure sensor measures a pressure associated with a gas flow within the trachea of the patient; and
a processor that is configured to control at least the inspiratory gas pressure controller and the expiratory gas pressure controller based on respective properties of the inspiratory gaseous flow and the expiratory gaseous flow and based on a pressure measurement from the pressure sensor.

76. The apparatus of claim 75, further comprising:
a second inspiratory lumen, wherein a second inspiratory gas pressure controller is configured to control provision of a second inspiratory gaseous flow through the second inspiratory lumen to a third portion of the airway of the patient while the second inspiratory lumen is at least partially inserted into the airway.

77. The apparatus of claim 76, wherein the inspiratory lumen is configured to be directed toward a first direction while the inspiratory lumen is at least partially inserted into the airway, and wherein the second inspiratory lumen is configured to be directed toward a second direction while the second inspiratory lumen is at least partially inserted into the airway, wherein the second direction is distinct from the first direction.

78. The apparatus of claim 76, wherein the second inspiratory lumen is configured to be threaded through the inspiratory lumen.

79. The apparatus of claim 75, further comprising:
a second expiratory lumen, wherein a second expiratory gas pressure controller is configured to control evacuation of a second expiratory gaseous flow through the second expiratory lumen from a third portion of the airway of the patient while the second expiratory lumen is at least partially inserted into the airway.

80. The apparatus of claim 79, wherein the expiratory lumen is configured to be directed toward a first direction while the expiratory lumen is at least partially inserted into the airway, and wherein the second expiratory lumen is configured to be directed toward a second direction while the second expiratory lumen is at least partially inserted into the airway, wherein the second direction is distinct from the first direction.

81. The apparatus of claim 79, wherein the second expiratory lumen is configured to be threaded through the expiratory lumen.

82. The apparatus of claim 75, wherein at least one of the inspiratory lumen or the expiratory lumen is curved.

83. The apparatus of claim 75, further comprising:
an additional lumen that is curved, wherein the additional lumen is at least one of an additional inspiratory lumen or an additional expiratory lumen.

84. The apparatus of claim 75, wherein the inspiratory lumen is configured to be threaded through the expiratory lumen.

85. The apparatus of claim 75, wherein the expiratory lumen is configured to be threaded through the inspiratory lumen.

86. The apparatus of claim 75, wherein a lumen portion is at least partially pliable, wherein the lumen portion is a portion of at least one of the inspiratory lumen or the expiratory lumen.

87. The apparatus of claim 75, wherein a lumen portion is at least partially rigid, wherein the lumen portion is a portion of at least one of the inspiratory lumen or the expiratory lumen.

88. The apparatus of claim 75, further comprising:
a marker along at least a portion of at least one of the inspiratory lumen or the expiratory lumen, wherein the marker includes at least one of a solenoid, a magnetic field emitter, a electromagnetic field emitter, a wireless signal transmitter, a radioactive material, a radiopaque material, or a radiolucent material.

89. The apparatus of claim 75, wherein the processor is configured to control the inspiratory gas pressure controller and the expiratory gas pressure controller to cause the inspiratory gaseous flow and the expiratory gaseous flow to be related based on a function.

90. The apparatus of claim 75, further comprising:
an adapter configured to be coupled to an endotracheal tube, wherein the adapter is configured to segregate a gaseous flow within the endotracheal tube into a plurality of separate flows, wherein the plurality of separate flows include at least the inspiratory gaseous flow through the inspiratory lumen and the expiratory gaseous flow through the expiratory lumen.

91. The apparatus of claim 75, further comprising:
a filter in the inspiratory lumen, wherein the filter is configured to filter at least a portion of the inspiratory gaseous flow as the inspiratory gaseous flow passes through the inspiratory lumen; and
a one-way flow valve configured to restrict the expiratory gaseous flow from reaching the filter.

92. The apparatus of claim 75, wherein the inspiratory lumen is configured to reach a first depth corresponding to the first portion of the airway of the patient, wherein the expiratory lumen is configured to reach a second depth corresponding to the second portion of the airway of the patient, wherein the first depth is distinct from the second depth.

93. The apparatus of claim 75, wherein at least one of a first position of the inspiratory lumen in the airway or a second position of the expiratory lumen in the airway is changeable.

94. The apparatus of claim 75, further comprising:
a first flow pressure sensor along the inspiratory lumen; and
a second flow pressure sensor along the expiratory lumen, wherein the processor is configured to control the inspiratory gas pressure controller and the expiratory gas pressure controller based on respective pressure measurements from the first flow pressure sensor and the second flow pressure sensor.

95. The apparatus of claim 75, wherein the processor is configured to, based on at least one measurement of a concentration of a specified gas in a mixture of gases in the expiratory gaseous flow, perform at least one of:
cause the inspiratory gas pressure controller to modify an inspiratory pressure of the inspiratory gaseous flow, or
cause the expiratory gas pressure controller to modify an expiratory pressure of the expiratory gaseous flow;
wherein the at least one measurement is received from at least one sensor.

96. The apparatus of claim 95, wherein the specified gas is carbon dioxide.

97. The apparatus of claim 75, wherein a diameter of a lumen is based on a diameter of a bronchus in the airway of the patient, wherein the lumen is at least one of the inspiratory lumen or the expiratory lumen, wherein the bronchus is in at least one of the first portion of the airway of the patient or the second portion of the airway of the patient.

98. The apparatus of claim 75, further comprising:
an extraction tube configured to be coupled to a suction system, the extraction tube configured to extract non-gaseous matter from the expiratory gaseous flow.

99. The apparatus of claim 98, wherein the suction system is configured to synchronize suction at the extraction tube with at least one of the inspiratory gaseous flow or the expiratory gaseous flow to minimize net gas volume loss from the airway of the patient.

100. The apparatus of claim 75, wherein the processor is configured to cause the expiratory gas pressure controller to apply a first pressure to the expiratory lumen, wherein the first pressure is less than a second pressure in the second portion of the airway of the patient.

101. The apparatus of claim 75, wherein the processor is configured to cause the inspiratory gas pressure controller to apply a first pressure to the inspiratory lumen, wherein the first pressure is greater than a second pressure in the second portion of the airway of the patient.

102. The apparatus of claim 75, wherein the processor is configured to delay initiation of the inspiratory gaseous flow to allow for a full expiration from the airway of the patient to calibrate the processor, wherein the full expiration is an expiration from a peak airway pressure associated with an inspiration to a trough airway pressure associated with a positive end-expiratory pressure (PEEP).

103. The apparatus of claim 75, wherein the expiratory gas pressure controller is configured to control the evacuation of the expiratory gaseous flow to assist with a full expiration, wherein the full expiration is an expiration from a peak airway pressure associated with an inspiration to a trough airway pressure associated with a positive end-expiratory pressure (PEEP), wherein the processor is configured to identify a threshold volume corresponding to the PEEP.

104. The apparatus of claim 103, wherein the processor is configured to add one or more inspiratory gas volumes and subtract one or more expiratory gas volumes to track a volume in at least a portion of the airway of the patient relative to the threshold volume wherein the processor is configured to control at least one of the inspiratory gas pressure controller or the expiratory gas pressure controller based on the tracked volume, the one or more inspiratory gas volumes passing through the inspiratory lumen, the one or more expiratory gas volumes passing through at least one of the expiratory lumen or a suction system.

105. The apparatus of claim 75, wherein the processor is configured to prevent at least one of the expiratory gas pressure controller or a suction system from reducing a volume in at least a portion of the airway to be below a threshold volume when evacuating the expiratory gaseous flow, wherein the threshold volume is associated with a positive end-expiratory pressure (PEEP), and wherein the suction system is coupled to an extraction tube.

106. The apparatus of claim 75, wherein a distal end of the inspiratory lumen is configured to extend further into the airway than the distal end of the expiratory lumen during both inspiration and expiration.

107. The apparatus of claim 76, wherein the second inspiratory gas pressure controller is the inspiratory gas pressure controller.

108. The apparatus of claim 79, wherein the second expiratory gas pressure controller is the expiratory gas pressure controller.

109. The apparatus of claim 75, wherein the inspiratory gas pressure controller includes at least one of a valve, a pump, a compressor, a decompressor, a gas buffer, a pressurizer, a depressurizer, a turbine, an actuator, or a suction device.

110. The apparatus of claim 75, wherein the expiratory gas pressure controller includes at least one of a valve, a pump, a compressor, a decompressor, a gas buffer, a pressurizer, a depressurizer, a turbine, an actuator, or a suction device.

* * * * *